(12) United States Patent
Vournakis et al.

(10) Patent No.: US 7,041,657 B2
(45) Date of Patent: May 9, 2006

(54) COMPOSITIONS AND METHODS FOR MODULATION OF VASCULAR STRUCTURE AND/OR FUNCTION

(75) Inventors: John N Vournakis, Charleston, SC (US); Sergio Finkielsztein, Chestnut Hill, MA (US)

(73) Assignee: Marine Polymer Technologies Inc., Danvers, MA (US)

( * ) Notice: Subject to any disclaimer, the term of this patent is extended or adjusted under 35 U.S.C. 154(b) by 350 days.

(21) Appl. No.: 09/781,182

(22) Filed: Feb. 12, 2001

(65) Prior Publication Data

US 2002/0019367 A1    Feb. 14, 2002

(51) Int. Cl.
*A01N 43/04* (2006.01)
*A61K 31/715* (2006.01)

(52) U.S. Cl. .................. 514/62; 514/54; 514/930; 536/18.7; 536/55.2; 536/123.1

(58) Field of Classification Search ............... 514/54, 514/62, 930; 536/18.7, 55.2, 123.1
See application file for complete search history.

(56) References Cited

U.S. PATENT DOCUMENTS

| | | | |
|---|---|---|---|
| 5,219,749 A | 6/1993 | Bouriotis et al. | |
| 5,622,834 A | 4/1997 | Vournakis et al. | |
| 5,623,064 A | 4/1997 | Vournakis et al. | |
| 5,624,679 A | 4/1997 | Vournakis et al. | |
| 5,635,493 A * | 6/1997 | Vournakis et al. | 514/55 |
| 5,686,115 A | 11/1997 | Vournakis et al. | |
| 5,846,952 A | 12/1998 | Vournakis et al. | |
| 5,858,350 A | 1/1999 | Vournakis et al. | |
| 6,063,911 A | 5/2000 | Vournakis et al. | |

OTHER PUBLICATIONS

Barton et al. "Endothelin antagonists for hypertension and renal diseases" Curr. Opin. Nephrol. Hypertens. (1999), vol. 8, pp. 549-556.*
Pearson "Normal endothelial cell function" Lupus (2000), vol. 9, pp. 183-188.*
Webster's II: New Riverside university Dictionary, The Riverside Publishing Company (1994), p. 155.*
Alsip et al., 1996, "A new technique for studying the uterine microvasculature in the rat", Am. J. Obstet. Gynecol. 175: 388-395.
Austin and Sennett, 1986, "Dry chitosan salts and complexes of aliphatic carboxylic acids", in: *Chitin in Nature and Technology*, Muzzarelli et al., eds., Plenum Press, New York, pp. 279-286.
Barton and Luscher, 1999, "Endothelin antagonists for hypertension and renal disease", Curr. Opin. Nephrol. Hypertens. 8:549-556.
Becker et al., 2000, "Endothelial function and hemostasis", Z. Kardiol. 89:160-167.

Brooks et al., 1991, "Effect of nifedipine on cyclosporine A-induced nephrotoxicity, urinary endothelin excretion and renal endothelin receptor number". Eur. J. Pharmacol. 194: 115-117.
Caron et al., 1998, "Proposition of a technique to assess the vasoactive effects of hemoglobin-based oxygen carrying solutions in vivo: preliminary results in the rabbit aorta", Artif. Cells Blood Substit. Immobil. Biotechnol. 26:293-308.
Davidson et al., 2000, "Experimental study of a novel fibrin sealant for achieving haemostasis following partial hepatectomy", Br. J. Surg. 87:790-795.
Davis and Preston, 1981, "A simple modified carbodiimide method for conjugation of small-molecular-weight compounds to immunoglobulin G with minimal protein crosslinking", Anal. Biochem. 116:402-407.
Domard, 1986, "Circular dichroism study on N-acetylglucosamine oligomers", Int. J. Biol. Macromol. 8: 243-246.
Dupuis, 2000, "Endothelin receptor antagonists and their developing role in cardiovascular therapeutics", Can. J. Cardiol. 16:903-910.
Emerson et al., 1999, "Endogenous nitric oxide acts as a natural antithrombotic agent *in vivo* by inhibiting platelet aggregation in the pulmonary vasculature", Thromb. Haemost. 81:961-966.
Goldie, 1999, "Endothelins in health and disease: an overview", Clin. Exp. Pharmacol. Physiol. 26:145-148.
Guo et al., 1994, "Endothelial preserving actions of a nitric oxide donor in carotid arterial intimal injury", Methods Find. Exp. Clin. Pharmacol. 15:347-354.
Hirano, 1989, "Production and application of chitin and chitosan in Japan", in: *Chitin and Chitosan*, Skjak-Brack et al., eds., Elsevier Science Publishing Co., pp. 37-43.
Hirano et al., 1981, "SEM ultrastructure studies of N-acyl- and N-benzylidene-chitosan and chitosan membranes", J. Biomed. Mater. Res. 15:903-911.

(Continued)

*Primary Examiner*—Patrick Lewis
(74) *Attorney, Agent, or Firm*—Jones Day

(57) ABSTRACT

The present invention relates to compositions comprising semi-crystalline β-1-4-N-acetylglucosamine polymers (p-GlcNac) and methods utilizing such polymers modulation of vascular structure and/or function. The compositions and methods disclosed are useful for stimulating, in a p-GlcNac concentration-dependent manner, endothelin-1 release, vasoconstriction, and/or reduction in blood flow out of a breached vessel, as well as for contributing to or effecting cessation of bleeding. The methods of the present invention comprise topical administration of materials comprising semi-crystalline p-GlcNac polymers that are free of proteins, and substantially free of single amino acids as well as other organic and inorganic contaminants, and whose constituent monosaccharide sugars are attached in a β-1-4 conformation.

27 Claims, 39 Drawing Sheets

OTHER PUBLICATIONS

Figure 1:
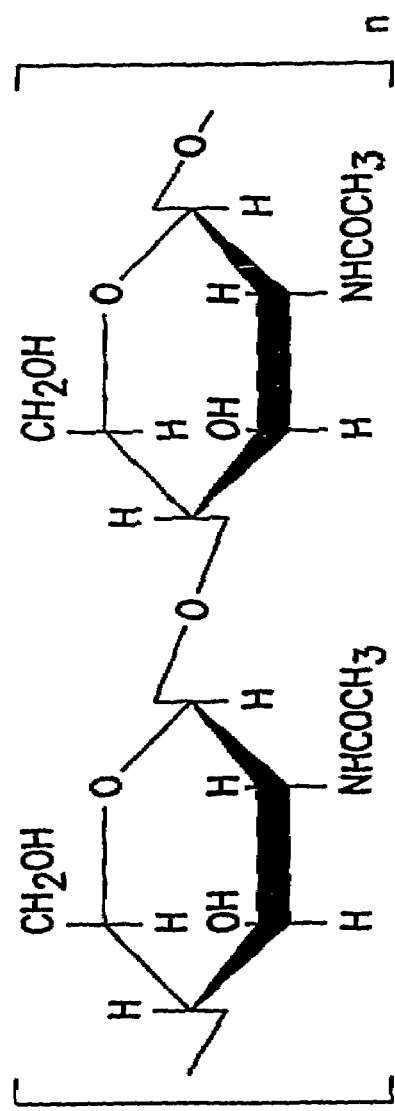

Hirano et al., 1976, "Selective *N*-acylation of chitosan", Carbohydrate Res. 47:315-320.

Hocher et al., 1997, "The paracrine endothelin system: pathophysiology and implications in clinical medicine", Eur. J. Clin. Chem. Clin. Biochem. 35:175-189.

Inoue et al., 1989, "The human endothelin family: three structurally and pharmacologically distinct isopepides predicted by three separate genes", Proc. Natl. Acad. Sci. USA 86:2863-2867.

Ishida et al., 1989, "Differential activities of two distinct endothelin family peptides on ileum and coronary artery", FEBS Lett. 247:337-340.

Kashiwabara et al., 1989, "Putative precursosrs of endothelin have less vasoconstrictor activity in vitro but a potent pressor effect in vivo", FEBS Lett. 247:73-76.

Kim and Greenburg, 2000, "Pharmacodynamic characterization of hemoglobin-induced vasoactivity in isolated rat thoracic aorta", J. Lab. Clin. Med. 135:180-187.

Komai et al., 1986, "Biomedical evaluation of acylated chitins as coating materials", in: *Chitin in Nature and Technology*, Muzzarelli et al., eds., Plenum Press, New York, pp. 497-506.

Kurita et al., 1990, "Preparations of soluble chitin derivatives and the modifications to branched chitins", Polymer Prep. 31:624-625.

Kurita and Inoue, 1989, "Preparation of indo-chitins and graft copolymerization onto the derivatives", in: *Chitin and Chitosan*, Skjak-Brack et al., eds., Elsevier Science Publishing Co., p. 365.

Lüscher and Wenzel, 1995, "Endothelin and endothelin antagonists: pharmacology and clinical implications", Agents Actions Suppl. 45:237-253.

Maresh et al., 1989, "Hydroxypropylation of chitosan", in: *Chitin and Chitosan*, Skjak-Brack et al., eds., Elsevier Science Publishing Co., pp. 389-395.

Mireles et al., 1992, " Complex formation of chitosan and naturally occurring polyanion", in: *Advances in Chitin and Chitosan*, Brine et al., eds., Elsevier Publishers, Ltd. , pp. 506-515.

Nishi et al., 1986, "Preparation and characterization of phosphorylated chitin and chitosan", in: *Chitin in Nature and Technology*, Muzzarelli et al., eds., Plenum Press, New York, pp. 297-299.

Noguchi et al., 1969, "Chitosan epichlorohydrin anion exchange resin with primary amine as absorption site", Kogyo Kagaku Zasshi 72:796-799 (in Japanese with English abstract).

Ortega Mateo and de Artinano, 1997, "Highlights on endothelins: a review", Pharmacological Res. 36:339-351.

Pasricha et al., 1999, "Endoscopic cryotherapy: experimental results and first clinical use", Gastrointest. Endosc. 49:627-631.

Pearson, 2000, "Normal endothelial cell function", Lupus 9:183-188.

Rosendorff, 1996, "Endothelin, vascular hypertrophy, and hypertension", Cardiovasc. Drugs Ther. 10:795-802.

Saida et al., 1989, "A novel peptide, vasoactive intestinal contractor, of a new (endothelin) peptide family. Molecular cloning, expression, and biological activity", J. Biol. Chem. 264:14613-14616.

Salamonsen et al., 1999, "Current concepts of the mechanisms of menstruation", Ballière's Best Pract. Res. Clinical Obstetrics and Gynaecology 13:161-179.

Salamonsen et al., 1999, "Endometrial endothelin: regulator of uterine bleeeding and endometrial repair", Clin. Exp. Pharmacol. Physiol. 26:154-157.

Schiffrin et al., 1995, "Antihypertensive effect of an endothelin receptor antagonist in DOCA-salt spontaneously hypertensive rats", Br. J. Pharmacol. 115:1377-1381.

Schini-Kerth, 1999, "Vascular biosynthesis of nitric oxide: effect on hemostasis and fibrinolysis.", Transfus. Clin. Biol. 6:355-363.

Schorigin and Halt, 1934, "Über die nitriering von chitin", Chem. Ber. 67:1712-1714 (in German).

Schweiger, 1972, "Polysaccharide sulfates. I. Cellulose sulfate with a high degree of substitution", Carbohydrate Res. 21:219-228.

Shichiri et al., 1991, "Endothelin-1 as an autocrine/paracrine factor for human tumor cell lines", J. Cardiovasc. Pharmacol. 17 (suppl. 7):S76-S78.

Sirieix et al., 1998, "Comparative study of different biological glues in an experimental model of surgical bleeding in anesthetized rats: platelet-rich and -poor plasma-based glue with and without aprotinin versus commercial fibrinogen-based glue", Ann. Vasc. Surg. 12:311-316.

Staros et al., 1986, "Enhancement by *N*-hydroxysulfosuccinimide of water-soluble carbodiimide-mediated coupling reactions", Anal. Biochem. 156:220-222.

Tokura et al., 1983, "Studies on chitin. VIII. SOme properties of water soluble chitin derivatives", Polymer J. 15:485-489.

U.S. Pharmacopeia XXII, 1991, Supplement 5, pp. 2702-2703.

U.S. Pharmacopeia XXII, 1990, pp. 1495-1497.

Warner, 1999, "Relationships between the endothelin and nitric oxode pathways", Clin. Exp. Pharmacol. Physiol. 26:247-252.

Webb and Meek, 1997, "Inhibitors of endothelin", Med. Res. Rev. 17:17-67.

Yanagisawa et al., 1988, "A novel potent vasoconstrictor peptide produced by vascular endothelial cells", Nature 332:411-415.

Yang et al., 1994, "Thrombin-induced endothelium-dependent inhibition and direct activation of platelet-vessel wall interaction. Role of prostacyclin, nitric oxide, and thromboxane A2", Circulation 89:2666-2672.

Yao et al., 1992, "Endogenous nitric oxide protects against platelet aggregation and cyclic flow variations in stenosed and endothelium-injured arteries", Circulation 86:1302-1309.

* cited by examiner

| PEAK | %RF | | AMPLITUDE | %SIGMA | AREA | %TOTAL | | RATIO | | RATIO |
|---|---|---|---|---|---|---|---|---|---|---|
| 1 | 5 | C=0 | 0.087 | 0.29 | 1.304 | 1.674 | | | | 5.609 |
| 2 | 6 | C=0 | 0.146 | 0.38 | 2.855 | 3.664 | 4.159 | 1.759 | | 2.562 |
| 3 | 47 | C1 | 0.563 | 0.38 | 11.153 | 14.314 | 11.153 | 0.656 | | 0.656 |
| 4 | 59 | C4 | 0.452 | 0.32 | 7.41 | 9.51 | 7.410 | 0.987 | | 0.987 |
| 5 | 63 | C5 | 0.311 | 0.49 | 7.906 | 10.147 | 7.906 | 0.925 | | 0.925 |
| 6 | 64 | C3 | 1.195 | 0.16 | 9.816 | 12.598 | | | | 0.745 |
| 7 | 65 | C3 | 0.533 | 0.4 | 11.11 | 14.259 | 20.926 | 0.350 | | 0.658 |
| 8 | 72 | C6 | 0.148 | 1.1 | 8.419 | 10.805 | | | | 0.869 |
| 9 | 73 | C6 | 0.21 | 0.18 | 1.98 | 2.541 | 10.399 | 0.703 | | 3.694 |
| 10 | 74 | C2 | 0.026 | 0.2 | 0.27 | 0.346 | | | | 27.089 |
| 11 | 75 | C2 | 0.227 | 0.72 | 8.38 | 10.755 | 8.650 | 0.846 | | 0.873 |
| 12 | 94 | CH3 | 0.377 | 0.38 | 7.314 | 9.387 | | | | 1.000 |

FIG.5A

| PEAK | %RF |     | AMPLITUDE | %SIGMA | AREA   | %TOTAL |        | RATIO  | RATIO |
|------|-----|-----|-----------|--------|--------|--------|--------|--------|-------|
| 1    | 4   | C=O | 0.803     | 0.42   | 18.08  | 14.5   | 18.080 | 0.8308 | 0.831 |
| 2    | 27  | C1  | 0.594     | 0.53   | 16.959 | 13.6   | 16.959 | 0.8857 | 0.886 |
| 3    | 37  | C4  | 2.073     | 0.28   | 30.787 | 24.68  | 30.787 | 0.4879 | 0.488 |
| 4    | 39  | C5  | 0.581     | 0.48   | 14.915 | 11.96  | 14.915 | 1.007  | 1.007 |
| 5    | 51  | C6  | 0.096     | 1.06   | 5.504  | 4.413  |        |        | 2.729 |
| 6    | 54  | C6  | 0.324     | 0.56   | 9.767  | 7.831  | 15.271 | 0.9836 | 1.538 |
| 7    | 57  | C2  | 0.197     | 0.55   | 5.848  | 4.689  |        |        | 2.568 |
| 8    | 59  | C2  | 0.226     | 0.64   | 7.843  | 6.289  | 13.691 | 1.0971 | 1.915 |
| 9    | 95  | CH3 | 0.363     | 0.77   | 15.02  | 12.04  | 15.020 |        | 1.000 |

200μm

200μm

200μm

200μm

200μm

200μm

PROTOTYPE 1: DAY 0

PROTOTYPE 1: DAY 14

PROTOTYPE 1: DAY 21

PROTOTYPE 3A: DAY 0

PROTOTYPE 3A: DAY 14

COMPOSITIONS AND METHODS FOR MODULATION OF VASCULAR STRUCTURE AND/OR FUNCTION

1 INTRODUCTION

The present invention relates to compositions comprising semi-crystalline poly-β-1→4-N-acetylglucosamine (p-GlcNac) polysaccharide polymers and methods utilizing such polymers for stimulating, in a p-GlcNac concentration-dependent manner, transient, localized stimulation of endothelin-1 release, vasoconstriction, and/or reduction in blood flow out of a breached vessel. These effects, individually and/or collectively, contribute or lead to cessation of bleeding. More specifically, the methods of the present invention comprise topical administration of compositions and materials comprising semi-crystalline polymers of N-acetylglucosamine that are free of proteins and substantially free of single amino acids and other organic and inorganic contaminants, and whose constituent monosaccharide sugars are attached in a β-1→4 conformation.

2 BACKGROUND

Vascular homeostasis depends, in part, upon the regulated secretion of biochemical modulators by endothelial cells. Under normal physiological conditions, endothelial cells synthesize and secrete nitric oxide, prostacyclin, PG12, adenosine, hyperpolarizing factor, tissue factor pathway inhibitor, and scuplasminogen activator. Endothelial cells also activate antithrombin III and protein C, which, collectively, mediate vascular dilation, inhibit platelet adhesion, platelet activation, thrombin formation and fibrin deposition. Nitric oxide, in particular, plays a critical role in vascular homeostasis (Pearson, J. D. (2000) *Lupus* 9 (3): 183–88; Becker et al. (2000) *Z Kardiol* 89 (3): 160–7; Schinin-Kerth, V. B. (1999) *Transfus Clin Biol* 6 (6): 355–63).

Production of nitric oxide and prostacyclin, which are powerful vasodilators and inhibitors of platelet aggregation and activation, underlies the antithrombotic activity of the endothelium (Yang et al. (1994) *Circulation* 89 (5): 2666–72). Nitric oxide is synthesized at a constitutive, basal level from arginine by nitric oxide synthase, and this synthesis is stimulated by the vaso-active agents acetylcholine and bradykinin. It has been shown that inhibition of nitric oxide synthase by the arginine analogues monomethyl-L-arginine (L-NMMA) and nitro-L-arginine methyl ester (L-NAME) reduces nitric oxide levels and leads not only to vasoconstriction, as measured by intravascular ultrasound imaging, but also to an increase in platelet aggregation (Yao et al. (1992) *Circulation* 86 (4): 1302–9; Emerson et al. (1999) *Thromb Haemost* 81 (6): 961–66).

Perturbation of the endothelium as the result of atherosclerosis, diabetes, postischemic reperfusion, inflammation or hypertension for example, leads to a prothrombotic state in which the endothelium elaborates a further set of biochemical modulators including TNF-α, IL-8, von Willebrand factor, platelet activating factor, tissue plasminogen activator, and type 1 plasminogen activator inhibitor. (Pearson, J. D. (2000) *Lupus* 9 (3): 183–88; Becker et al. (2000) *Z Kardiol* 89 (3): 160–7; Schinin-Kerth, V. B. (1999) *Transfus Clin Biol* 6 (6): 355–63). In addition, the vascular endothelium synthesizes and elaborates the endothelins, which are the most potent vasoconstrictor peptides known.

The endothelins are a family of 21-amino acid peptides, i.e., endothelin-1, endothelin-2, and endothelin-3, originally characterized by their potent vasoconstricting and angiogenic properties (see, e.g., Luscher et al. (1995), *Agents Actions Suppl.* (Switzerland) 45: 237–253; Yanagisawa et al. (1988) *Nature* 332: 411–415). The three isopeptides of the endothelin family, endothelin-1, endothelin-2, and endothelin-3, possess highly conserved amino acid sequences that are encoded by three separate genes (see, e.g., Inoue et al. (1989) *Proc Natl Acad Sci USA* 86: 2863–67; Saida et al. (1989) *J Biol Chem* 264:14613–16). Although the endothelins are synthesized in several tissues including smooth muscle cells, endothelin-1 is exclusively synthesized by the vascular endothelium (Rosendorff, C. (1997) *Cardiovasc Drugs* 10 (6): 795–802). The endothelins are synthesized as preproendothelins of two hundred and three amino acids. The endothelin signal sequence is cleaved and the protein is then further proteolytically processed to yield the mature, biologically active 21 amino acid form (see, e.g., Kashiwabara et al. (1989) *FEBS Lett* 247: 337–40). Endothelin synthesis is regulated via autocrine mechanisms including endothelin and non-endothelin converting enzymes as well as by chymases (Baton et al. (1999) *Curr Opin Nephrol Hypertens* 8 (5): 549–56). Elaboration of endothelin-1 from the endothelium is stimulated by angiotensin II, vasopressin, endotoxin, and cyclosporin inter alia (see e.g. Brooks et al. (1991) *Eur J Pharm* 194: 115–17) and is inhibited by nitric oxide.

Endothelin activity is mediated via binding with preferential affinities to two distinct G protein-coupled receptors, $ET_A$ and $ET_B$, in an autocrine/paracrine manner (see, e.g., Hocher et al. (1997) *Eur. J Clin. Chem. Clin. Biochem.* 35 (3): 175–189; Shichiri et al. (1991) *J. Cardiovascular Pharmacol.* 17: S76–S78). $ET_A$ receptors are found on vascular smooth muscle linked to vasoconstriction and have been associated with cardiovascular, renal, and central nervous system diseases. $ET_B$ receptors are more complex and display antagonistic actions. $ET_B$ receptors in the endothelium have the dual roles of clearance and vasodilation, while $ET_B$ receptors on smooth muscle cells also mediate vasoconstriction (Dupuis, J. (2000) *Can J Cardiol* 16 (1): 903–10). The $ET_B$ receptors on the endothelium are linked to the release of nitric oxide and prostacycline (Rosendorff, C. (1997) *Cardiovasc Drugs* 10 (6): 795–802). There are a variety of agonists and antagonists of endothelin receptors (Webb et al. (1997) *Medicinal Research Reviews* 17 (1): 17–67), which have been used to study the mechanism of action of the endothelins. Because endothelin is known to have powerful vasoconstrictive activity, endothelin antagonists in particular (also termed "endothelin receptor antagonists" in the art) have been studied with regard to their possible role in treating human disease, most notably, cardiovascular diseases such as hypertension, congestive heart failure, atherosclerosis, restenosis, and myocardial infarction (Mateo et al. (1997) *Pharmacological Res.* 36 (5): 339–351).

Moreover, endothelin-1 has been shown to be involved in the normal functioning of the menstrual cycle. Menstruation represents a remarkable example of tissue repair and replacement, involving the regulated remodeling and regeneration of a new layer of endometrial tissue lining the uterus. This repair and remodeling process is remarkable in that it is accomplished without scarring, a phenomenon generally not seen in other organs of the body. Defects in that repair process are believed to be the basis of excessive or abnormal endometrial bleeding in women with documented menorrhagia as well as in women carrying subcutaneous levonorgestrel implants (NORPLANT) for contraceptive purposes. In both of these groups of patients, only very low levels of endometrial endothelin-1 have been detected as compared with control populations. Moreover, it has been indicated that endothelin-1 not only may play a role in effecting cessation of menstrual bleeding but endothelin-1 may also have a mitogenic activity required for regenerating and remodeling of endometrial tissue after menstruation (see Salamonsen et al. 1999, Balliere's Clinical Obstetrics and Gynaecology 13 (2): 161–79; Goldie 1999, Clinical and Experimental Pharmacology and Physiology 26: 145–48; Salamonsen et al. 1999, Clin. Exp. Phamaol. Physiol. 26 (2): 154–57).

In summary, vascular homeostasis reflects a dynamic balance between two physiological states mediated by the vascular endothelium. The first, which has been termed antithrombotic, is characterized inter alia by the production of nitric oxide, vasodilation, inhibition of platelet attachment and activation, and by repression of endothelin-1 synthesis. The second or prothrombotic physiological state is characterized inter alia by the production of endothelin-1, vasoconstriction, platelet activation, and hemostasis (Warner (1999), *Clinical and Experimental Physiology* 26: 347–52; Pearson, (2000), *Lupus* 9(3): 183–88).

In light of the physiological importance of vascular homeostasis, there is a need for methods and compositions that are capable of modulating one or more aspects of the above processes. More specifically, there is a need for compositions and methods for the modulation of endothelin release, vasoconstriction, and blood flow out of a breached vessel and which would therefore be useful for effecting cessation of bleeding. That is, although such compositions and methods would act in a manner that is not dependent upon physical barrier formation, coagulation, or blood clot formation, such compositions and methods would nevertheless contribute, inter alia, to the achievement of hemostasis. Accordingly, such methods and compositions would be expected to have therapeutic applications for the treatment of diseases or conditions arising as a consequence of the perturbation of vascular homeostasis. Moreover, in view of the systemic effects resulting, e.g., from administration to patients of endothelin-1 antagonists as described supra, there is an even greater need for compositions and methods that produce localized and transient physiological responses, including, but not limited to, stimulation of endothelin-1 release, in such patients.

3 SUMMARY OF THE INVENTION

The present invention relates to methods and compositions for the treatment or amelioration of vascular disorders including bleeding disorders. More specifically, the invention relates to compositions comprising semi-crystalline poly-β-1→4-N-acetylglucosamine (p-GlcNac) polysaccharide polymers, and use of such polymers in methods to effect transient localized, modulation of vascular structure and/or function by, e.g., stimulation of endothelin-1 release, vasoconstriction, and/or reduction in blood flow out of a breached vessel, thereby contributing to or effecting cessation of bleeding.

The present invention is based in part on the Applicants' discovery that topical application of semi-crystalline poly-β-1→4-N-acetylglucosamine (p-GlcNac) polysaccharide polymers to a vascular surface induces not only contraction of that vessel, thereby decreasing the lumen of that vessel, but also induction of a transient, localized stimulation of endothelin-1 release in those tissues contiguous with the applied compositions and materials disclosed herein.

The present invention relates, in one aspect, to a method for achieving transient, localized, modulation of vascular structure and/or function in a patient, comprising topical administration of a material comprising semi-crystalline poly-β-1→4 N-acetylglucosamine polymers, which are free of protein, substantially free of other organic contaminants, and substantially free of inorganic contaminants. Administration of these materials induces transient, localized physiological responses including, but not limited to, stimulation of endothelin-1 release, vasoconstriction, and reduction in blood flow out of a breached vessel.

In one embodiment of the present invention, endothelin-1 is released from vascular endothelial cells. In other aspects of this embodiment, endothelin-1 release is stimulated from other endothelial tissues or from platelets.

In one embodiment, the poly-β-1→4 N-acetylglucosamine polymer comprises about 50 to about 4,000 N-acetylglucosamine monosaccharides covalently attached in a β-1→4 conformation, and has a molecular weight of about 10,000 daltons to about 800,000 daltons. In another embodiment, the poly-β-1→4 N-acetylglucosamine polymer comprises about 50 to about 10,000 N-acetylglucosamine monosaccharides covalently attached in a β-1→4 conformation, and has a molecular weight of about 10,000 daltons to about 2 million daltons. In yet another embodiment, the poly-β-1→4 N-acetylglucosamine polymer comprises about 50 to about 50,000 N-acetylglucosamine monosaccharides covalently attached in a β-1→4 conformation, and has a molecular weight of about 10,000 daltons to about 10 million daltons. In another embodiment, the poly-β-1→4 N-acetylglucosamine polymer comprises about 50 to about 150,000 N-acetylglucosamine monosaccharides covalently attached in a β-1→4 conformation, and has a molecular weight of about 10,000 daltons to about 30 million daltons.

In preferred embodiments of the invention, the disclosed method is used for the treatment of a mammalian patient, and in more preferred embodiments, for the treatment of a human in need of such treatment. More specifically, modulation of vascular structure and/or function is used to effect cessation of bleeding, particularly in a patient afflicted with a coagulopathy. Such a disorder can be the result of a genetic defect, such as hemophilia, or a medical treatment, including for example, administration of systemic anticoagulants, e.g. coumadin, to a dialysis patient, cardiac patient, or other patient with an increased risk of vessel blockage. Similarly, the present method is used to effect a temporary, localized, reduction in blood flow out of a breached vessel during surgical repair of an aneurysm or excision of a tumor or polyp, particularly in a patient having a coagulopahtic condition, thereby minimizing blood loss during such a procedure. In other embodiments, the method of the present invention is used for the treatment of bleeding ulcers or varices, particularly esophageal varices. While not wishing to be bound by a particular theory or mechanism, it is believed that such cessation of bleeding by the methods disclosed herein occurs in a coagulation-independent manner.

In other embodiments of the method of the invention, the p-GlcNac-containing material is topically administered to the skin of the patient or to the surface of another organ, or the material may be applied directly to a vascular structure to be modulated, which may be a capillary, vein, or artery.

In yet another embodiment of the method of the invention, where the vascular structure is a breached blood vessel, topical application of the p-GlcNac-containing materials of the invention is used to achieve cessation of bleeding.

In a further embodiment of the invention, the extent of the transient, localized modulation of vascular structure and/or function is substantially proportional to the amount of semi-crystalline poly-β-1→4 N-acetylglucosamine applied.

The invention is also directed toward a biodegradable material comprising semi-crystalline poly-β-1→4 N-acetylglucosamine polymers which are free of protein, substantially free of other organic contaminants, and are substantially free of inorganic contaminants. In one embodiment, the semi-crystalline poly-β-1→4 N-acetylglucosamine polymers comprise about 50 to about 4,000 N-acetylglucosamine monosaccharides covalently attached in a β-1→4 conformation and have a molecular weight of about 10,000 daltons to about 800,000 daltons. In another embodiment, the semi-crystalline poly-β-1→4 N-acetylglucosamine polymer comprises about 50 to about 10,000 N-acetylglucosamine monosaccharides covalently attached in a β-1→4 conformation, and has a molecular weight of about 10,000 daltons to about 2 million daltons. In yet another embodiment, the poly-β-1→4 N-acetylglucosamine polymer comprises about 50 to about 50,000 N-acetylglucosamine monosaccharides covalently attached in a β-1→4 conformation, and has a molecular weight of about 10,000 daltons to about 10 million daltons. In another embodiment, the poly-β-1→4 N-acetylglucosamine polymer comprises about 50 to about 150,000 N-acetylglucosamine monosaccharides covalently attached in a β-1→4 conformation, and has a molecular weight of about 10,000 daltons to about 30 million daltons.

In another embodiment, the biodegradable material comprising semi-crystalline poly-β-1→4 N-acetylglucosamine polymers is a non-barrier-forming material.

In still another embodiment, the semi-crystalline poly-β-1→4 N-acetylglucosamine polymer comprises at least one N-acetylglucosamine monosaccharide that is deacetylated. In other aspects of this embodiment the poly-β-1→4 N-acetylglucosamine polymer may comprise about 10%, 20%, 30%, 40%, 50% or 60% deacetylated residues, provided the partially-deacetylated poly-β-1→4 N-acetylglucosamine polymer retains its semi-crystalline structure as demonstrated by sharp, discrete peaks when the polymer is analyzed by IR absorption spectroscopy, as described in Example 6, below.

4 BRIEF DESCRIPTION OF THE FIGURES

FIG. 1. Chemical structure of 100% p-GlcNAc. "n" refers to an integer ranging up to about 150,000.

Figure 2:
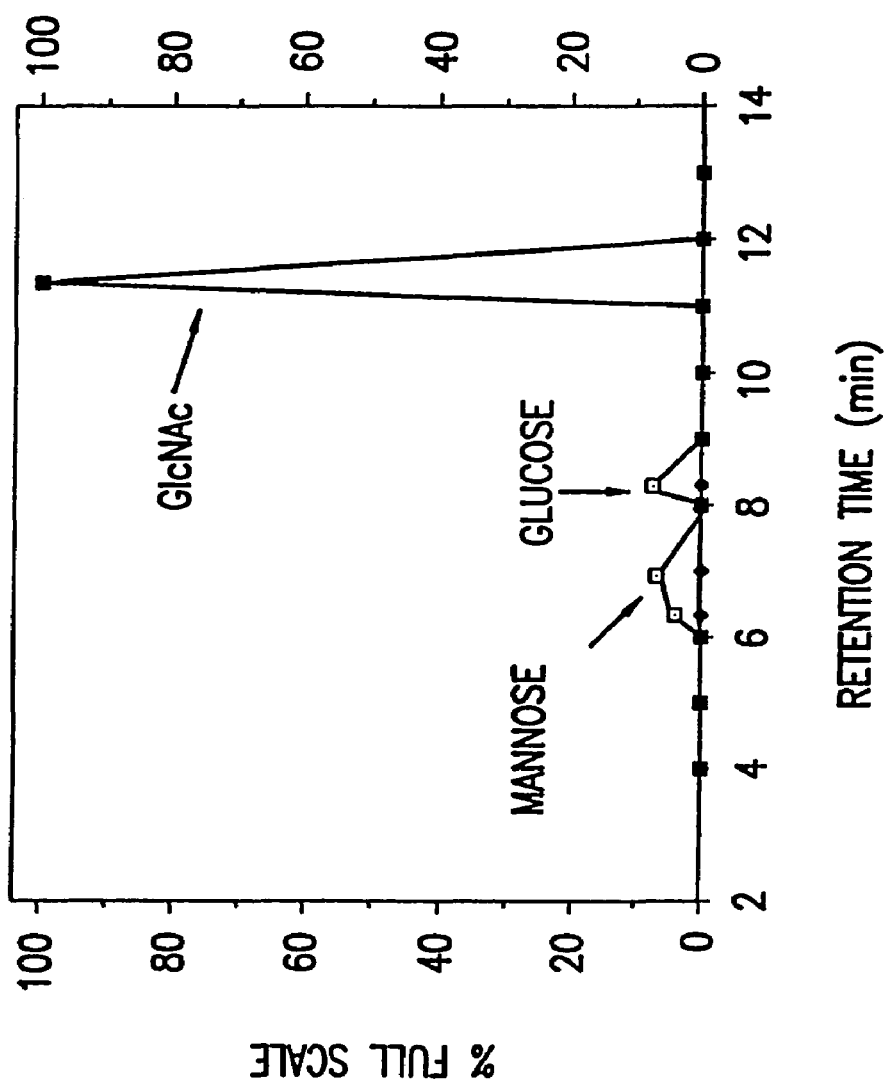

FIG. 2. Carbohydrate analysis of p-GlcNAc, Gas Chromatography-Mass Spectroscopy data. Solid squares represent p-GlcNAc purified using the acid treatment/neutralization variation of the Chemical/Biological method, as described in Section 5.3.2, below.

Figure 3A:
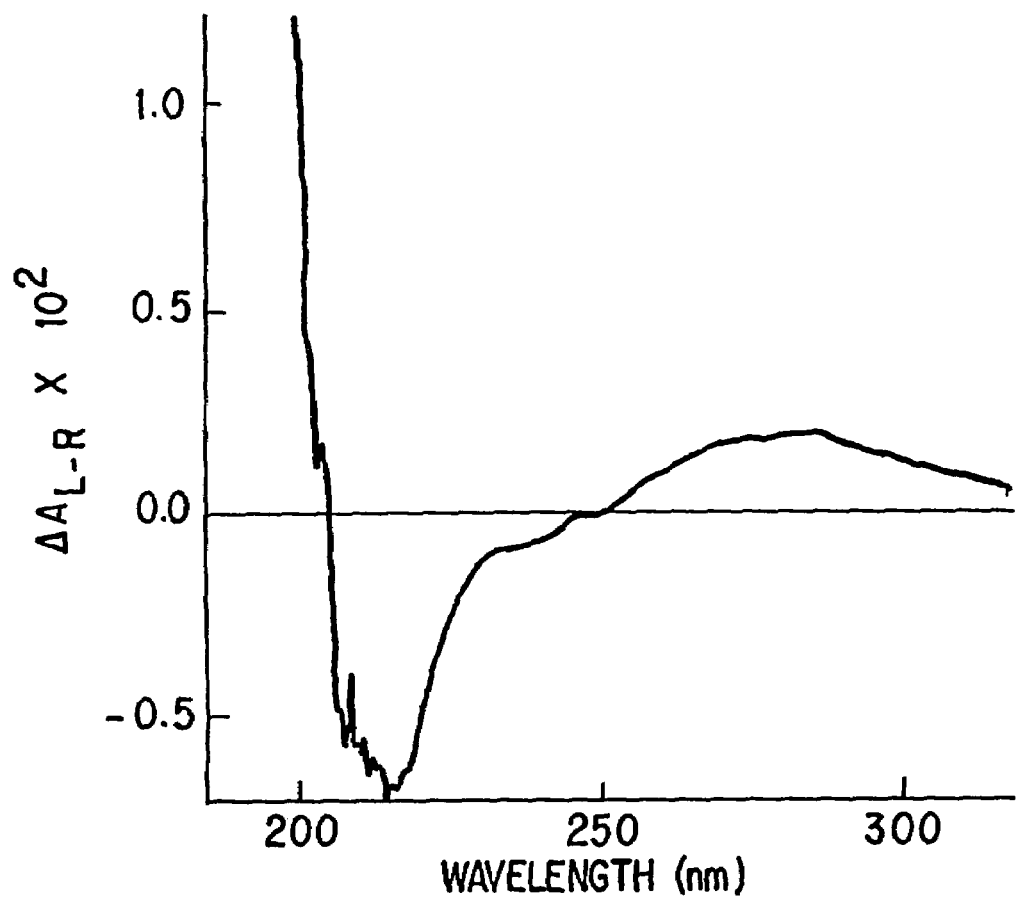

FIG. 3A. Circular dichroism spectra of solid membranes of pure p-GlcNAc.

Figure 3B:
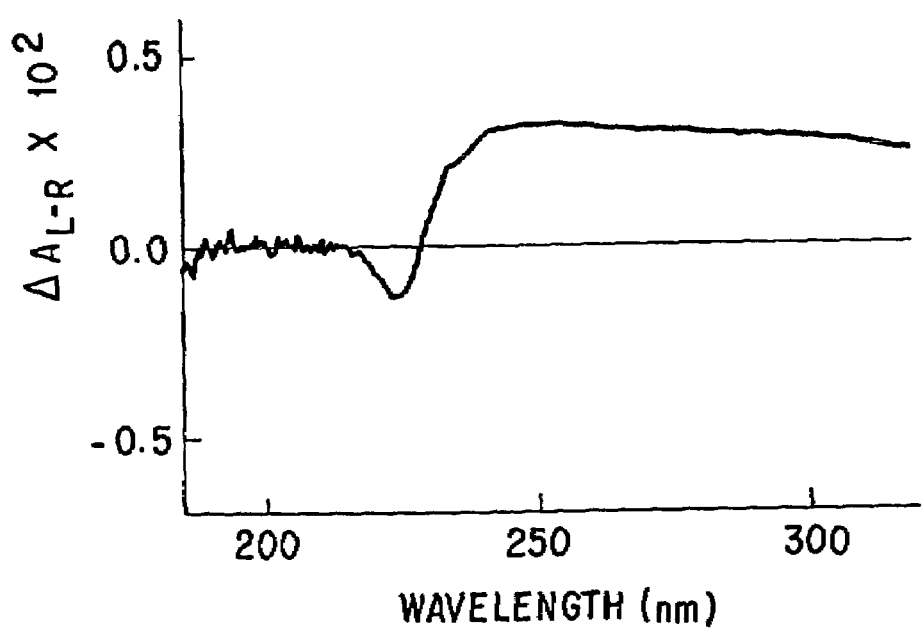

FIG. 3B. Circular dichroism spectra of solid membranes of Deacetylated p-GlcNAc. The disappearance of the 211 nm minimum and 195 nm maximum observed in pure p-GlcNAc (FIG. 3A) indicates complete deacetylation under the conditions used, as described in Section 5.4 below.

Figure 4A:
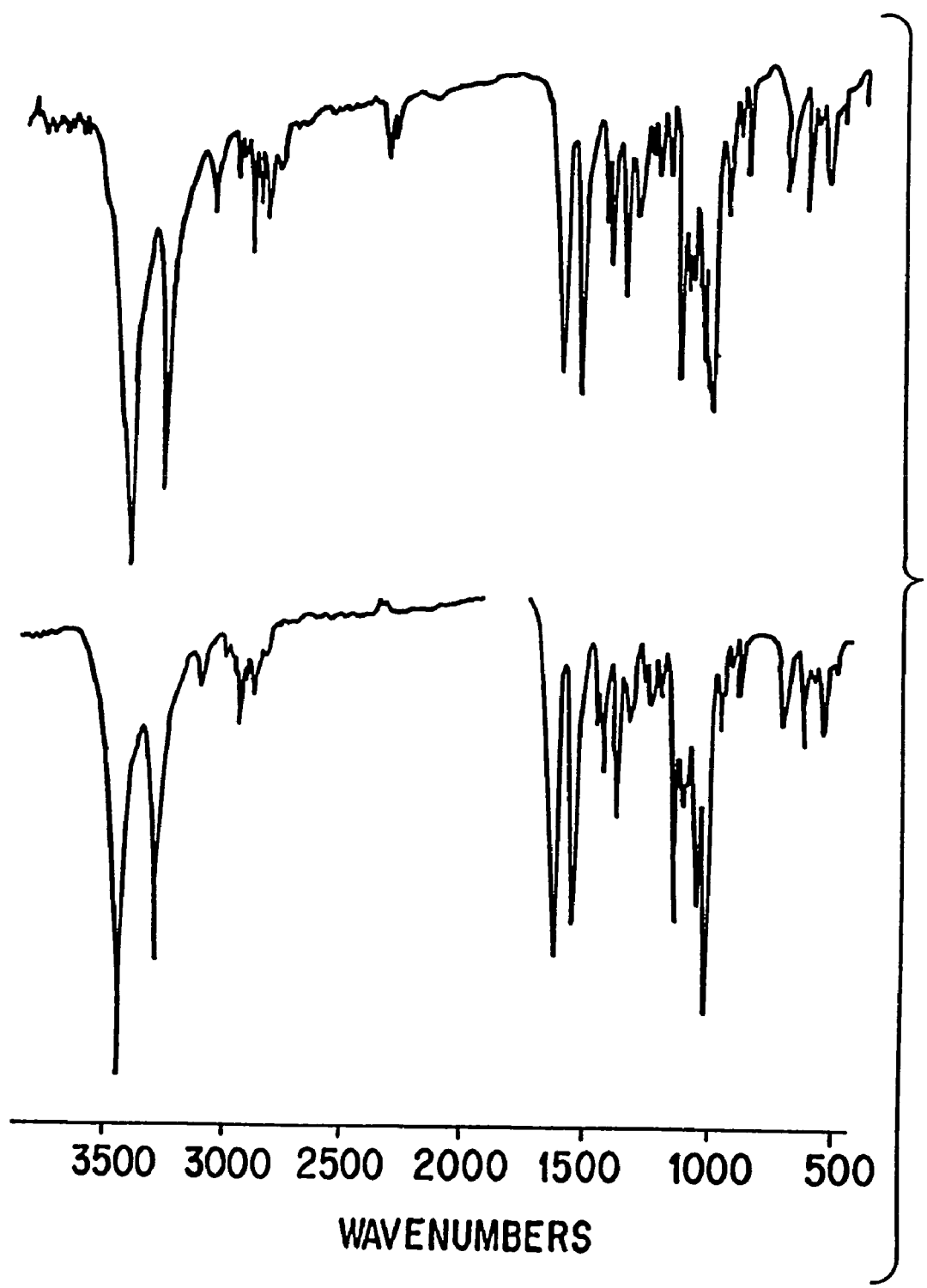

FIG. 4A. Infra-red spectra analyses of thin membranes of pure diatom p-GlcNAc prepared by the mechanical force purification method, top, and the chemical/biological purification method, bottom.

Figure 4B:
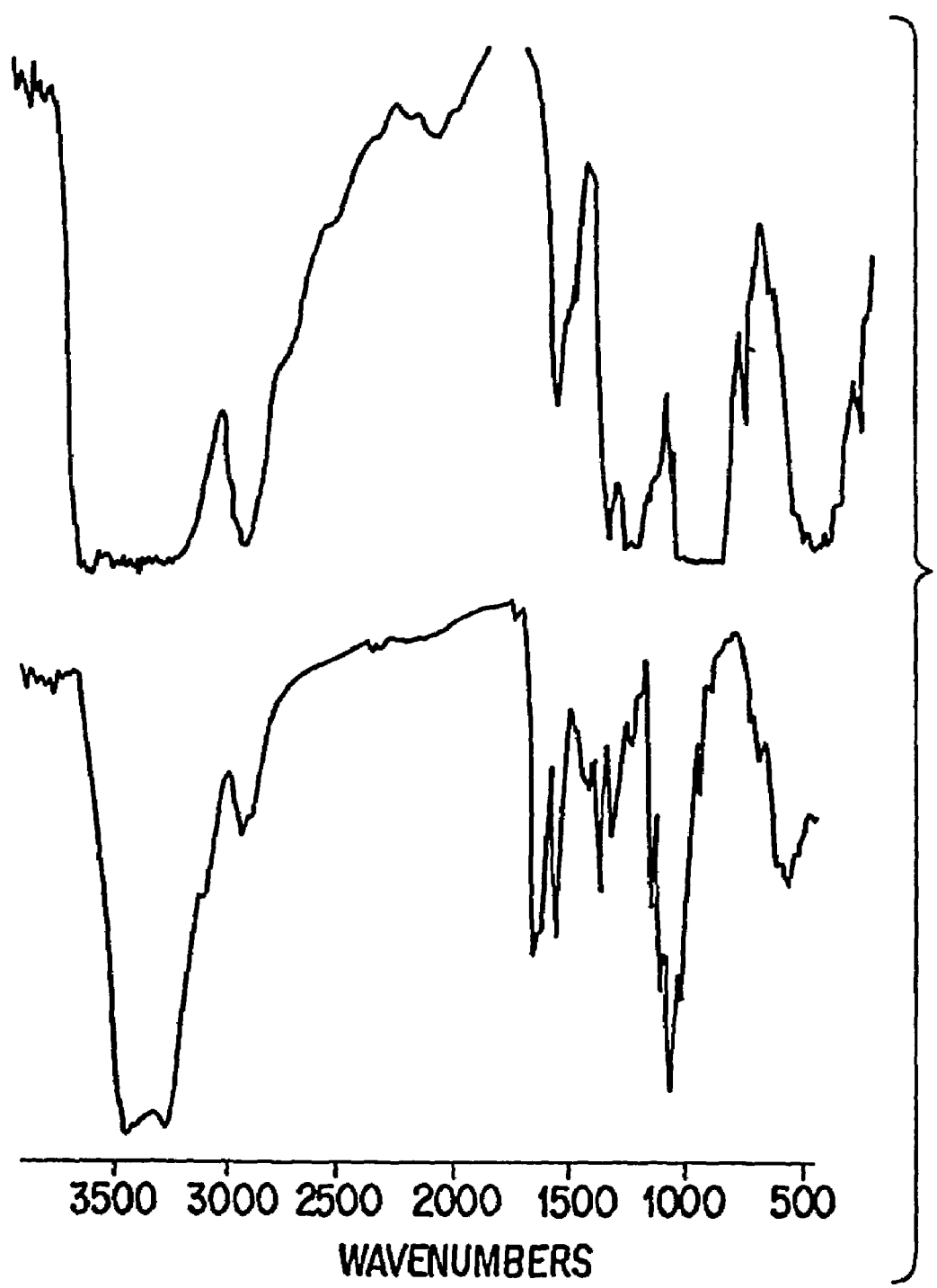

FIG. 4B. Infra-red spectra analyses of two preparations of commercial "chitin" cast into membranes according to the methods detailed in Section 5.5, below.

Figure 4C:
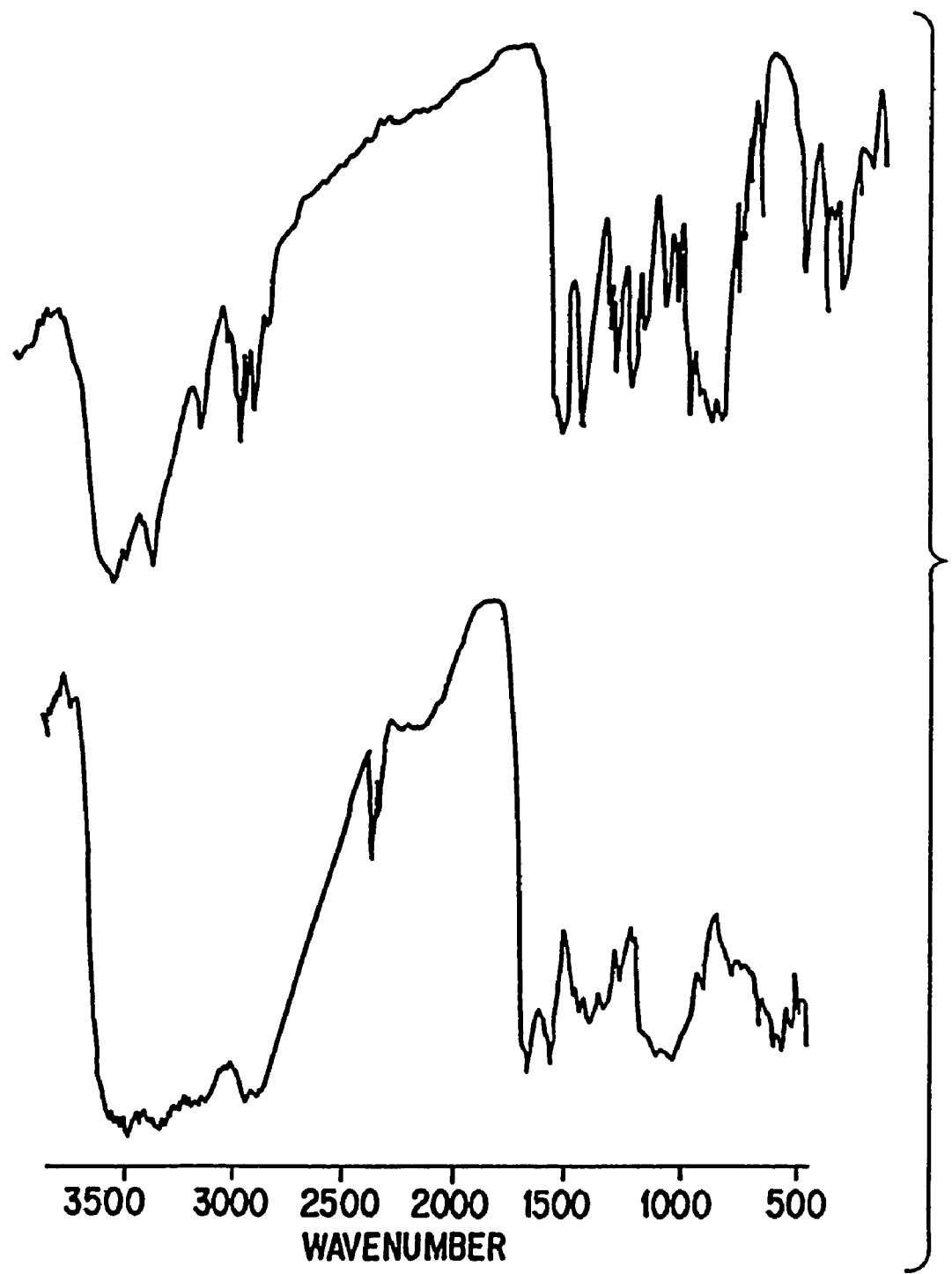

FIG. 4C. Infra-red spectra analyses of pure p-GlcNAc which was modified by heat denaturation (top) and by chemical deacetylation (bottom), according to the methods detailed in Section 5.4, below.

Figure 4D:
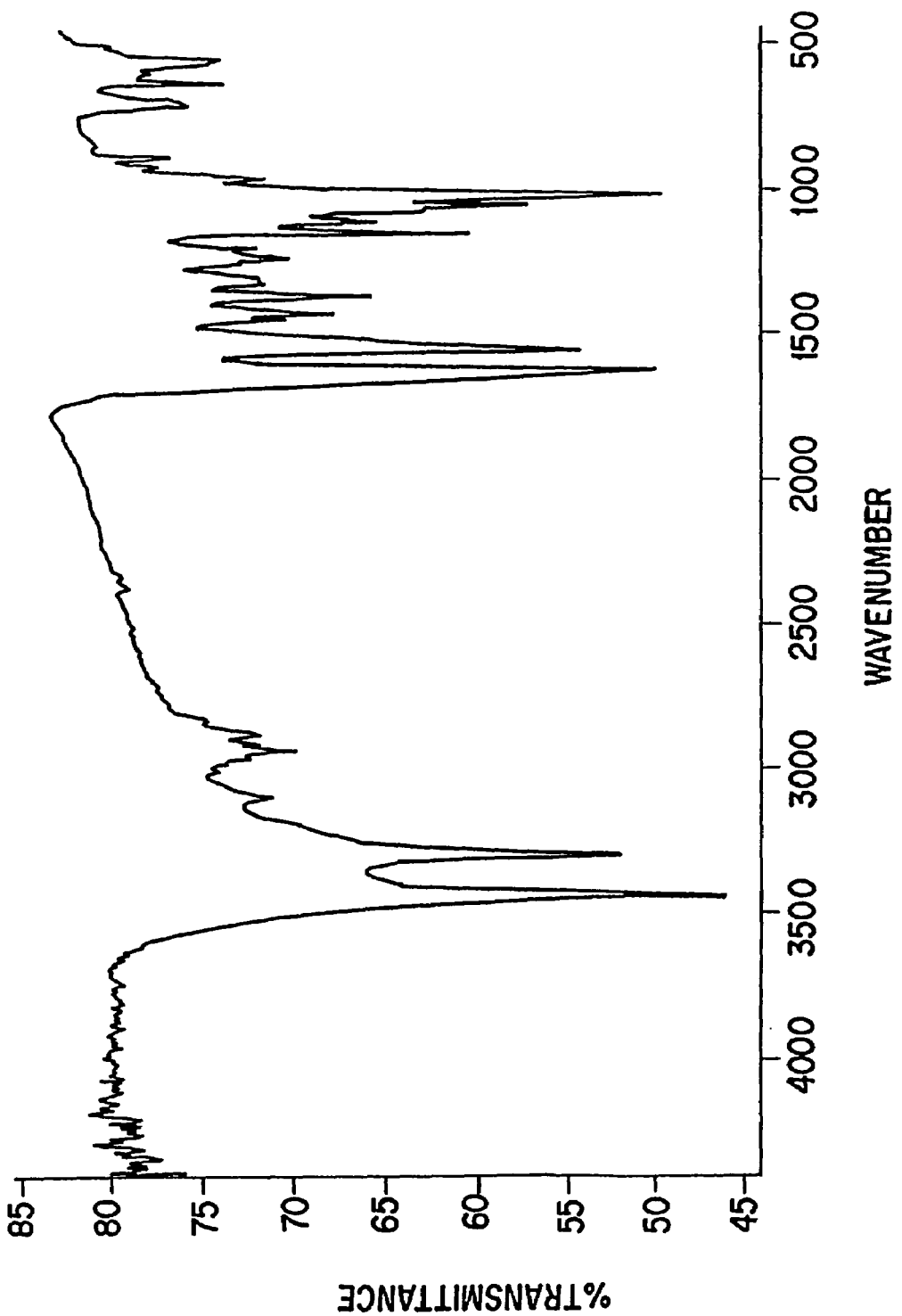

FIG. 4D. Infra-red spectrum analysis of a p-GlcNAc membrane derived from the diatom *Thalassiosira fluviatilis*, using the chemical/biological purification method, as detailed in Section 5.3.2, below.

Figure 4E:
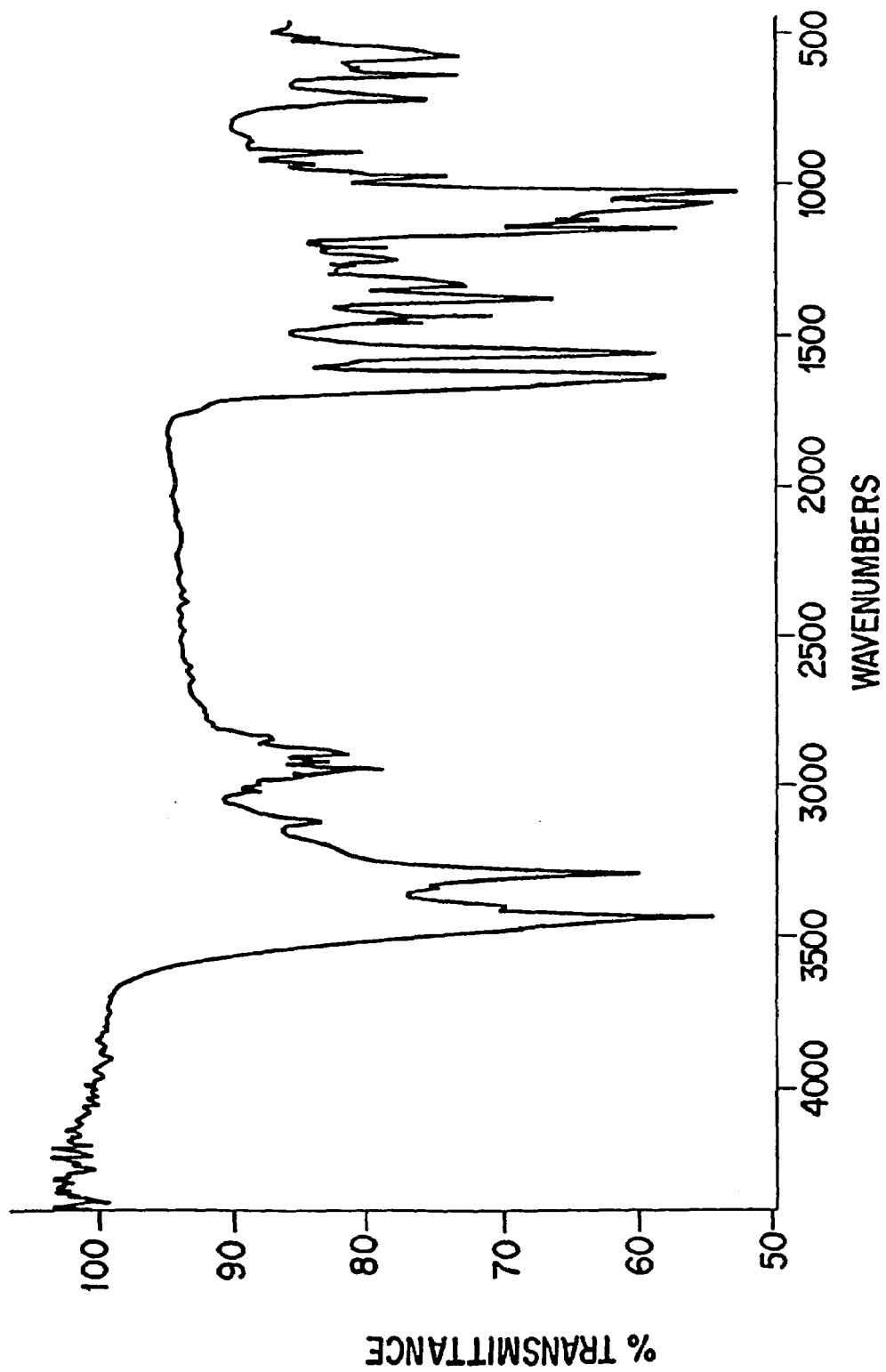

FIG. 4E. Infra-red spectrum analysis of a p-GlcNAc membrane prepared by the mechanical force purification method, as described in Section 5.3.1, below, following autoclaving.

FIG. 5A. NMR analysis of p-GlcNAc purified using the chemical/biological purification method as described in Section 5.3.2, below. Chart depicting peak amplitudes, areas, and ratios relative to reference controls. Ratio of total areas of peaks.

Figure 5B:
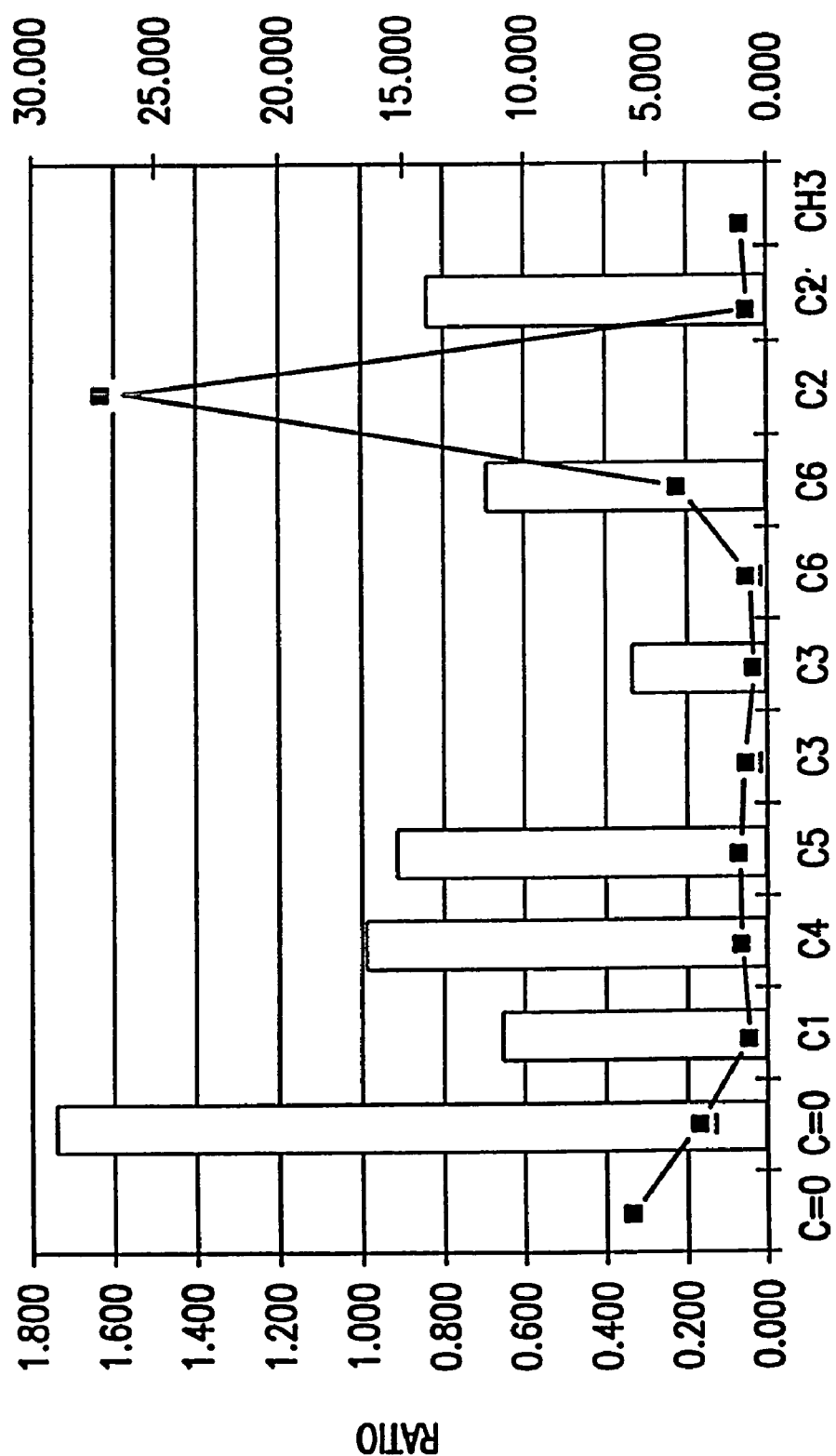

FIG. 5B. NMR analysis of p-GlcNAc purified using the chemical/biological purification method as described in Section 5.3.2. The graph depicts the ratios of total areas of peaks.

Figure 6A:
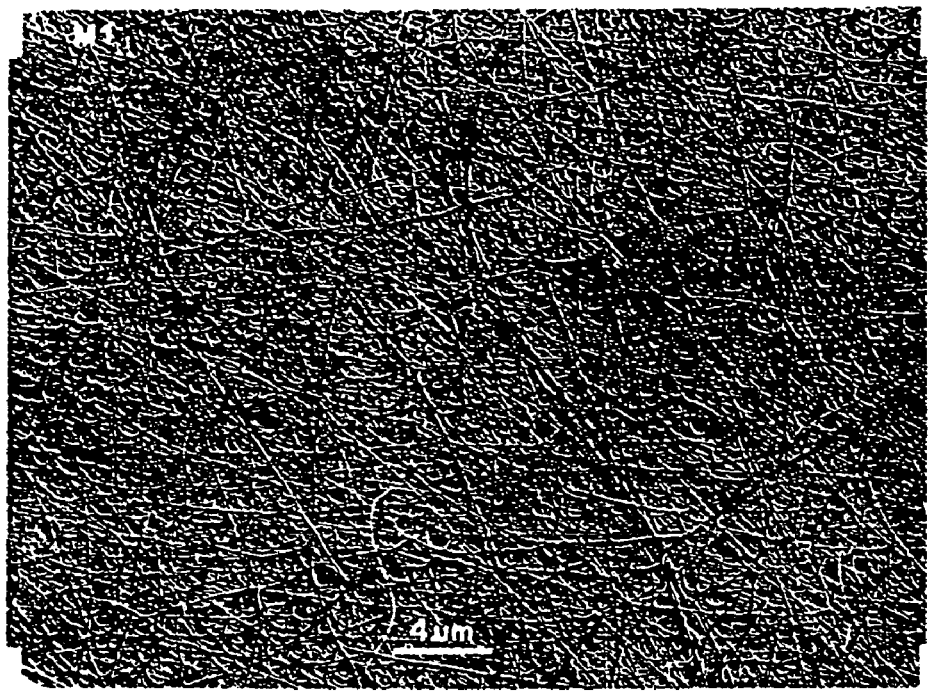
Figure 6B:
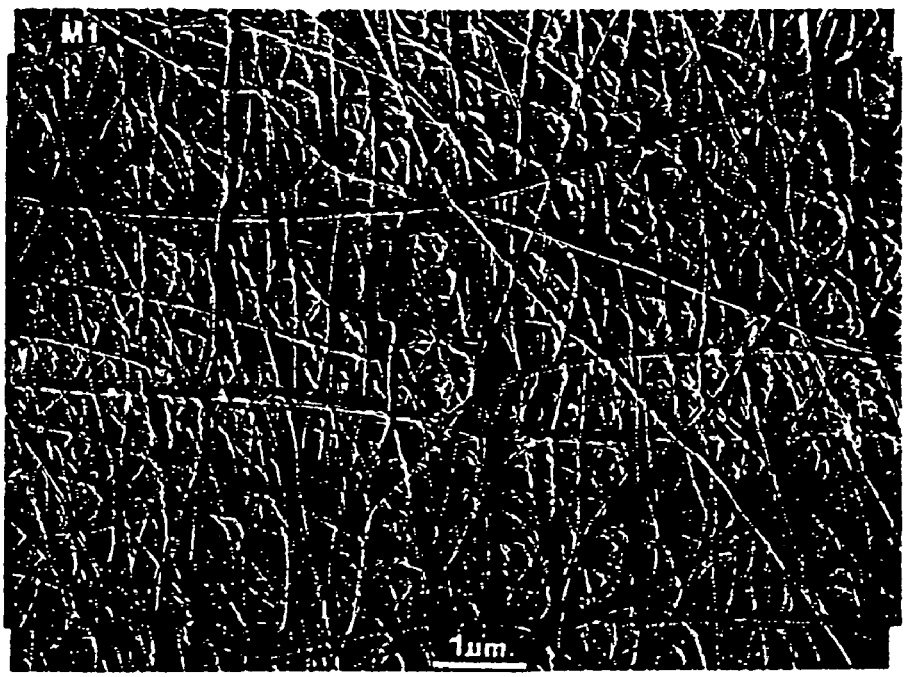

FIGS. 6A–B. Transmission electron micrographs (TEM) of a p-GlcNAc membrane prepared by the mechanical force purification method as described in Section 5.3.1, below. Magnification: (FIG. 6A), 4190×; (FIG. 6B), 16,250×.

Figure 7A:
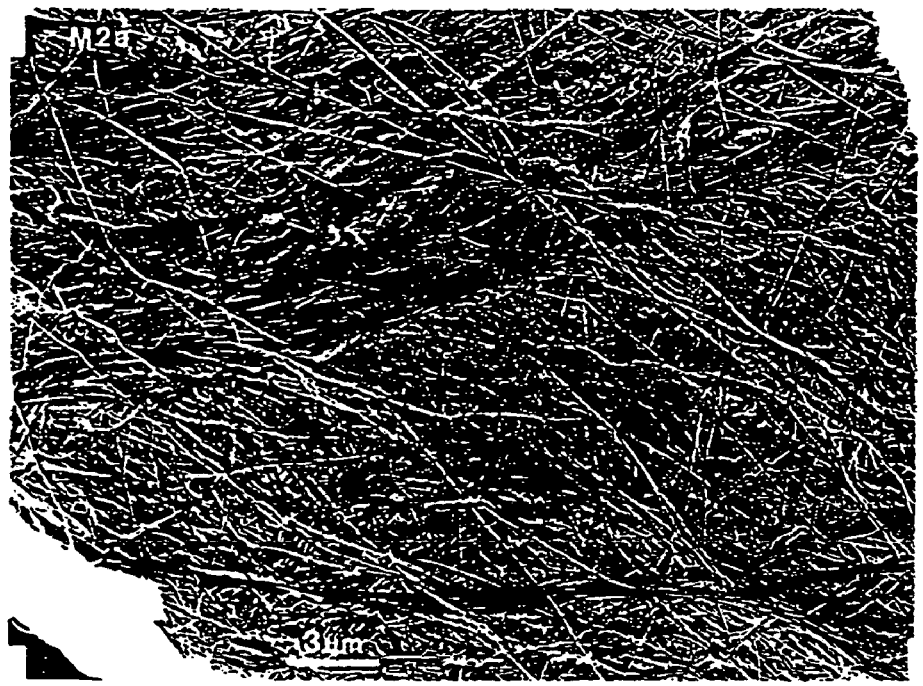
Figure 7B:
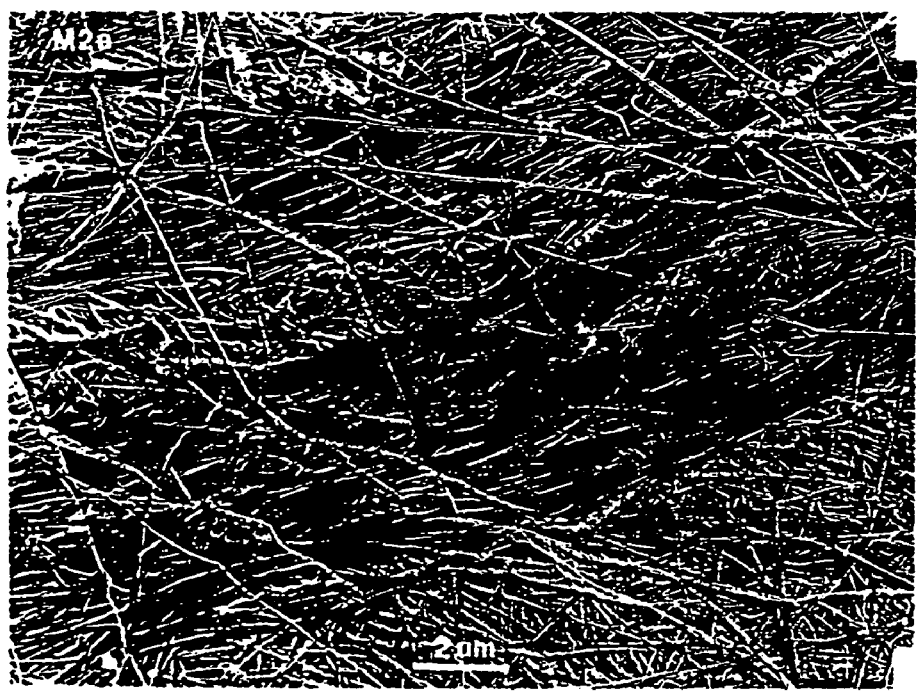

FIGS. 7A–B. Transmission electron micrographs (TEM) of a p-GlcNAc membrane by HF treatment as described in the discussion of the chemical/biological purification method in Section 5.3.2, below. Magnification: (FIG. 7A), 5270×; (FIG. 7B) 8150×.

Figure 8A:
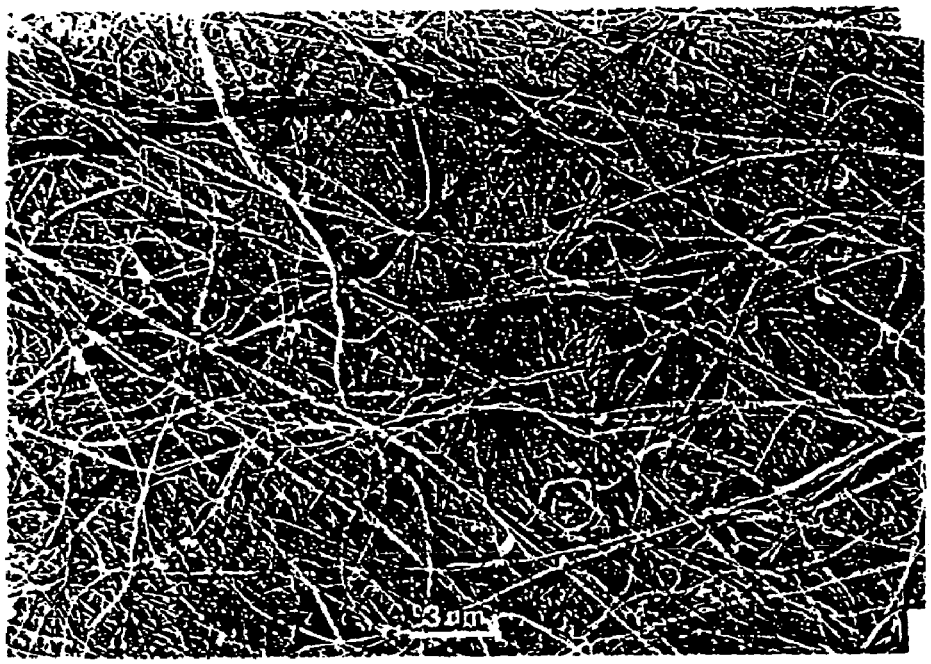
Figure 8B:

FIGS. 8A–B. Transmission electron micrographs (TEM) of a p-GlcNAc membrane prepared by the acid treatment/neutralization variation of the chemical/biological purification method, as described in Section 5.3.2, below. Magnification: (FIG. 8A), 5270×; (FIG. 8B), 16,700×.

Figure 9A:
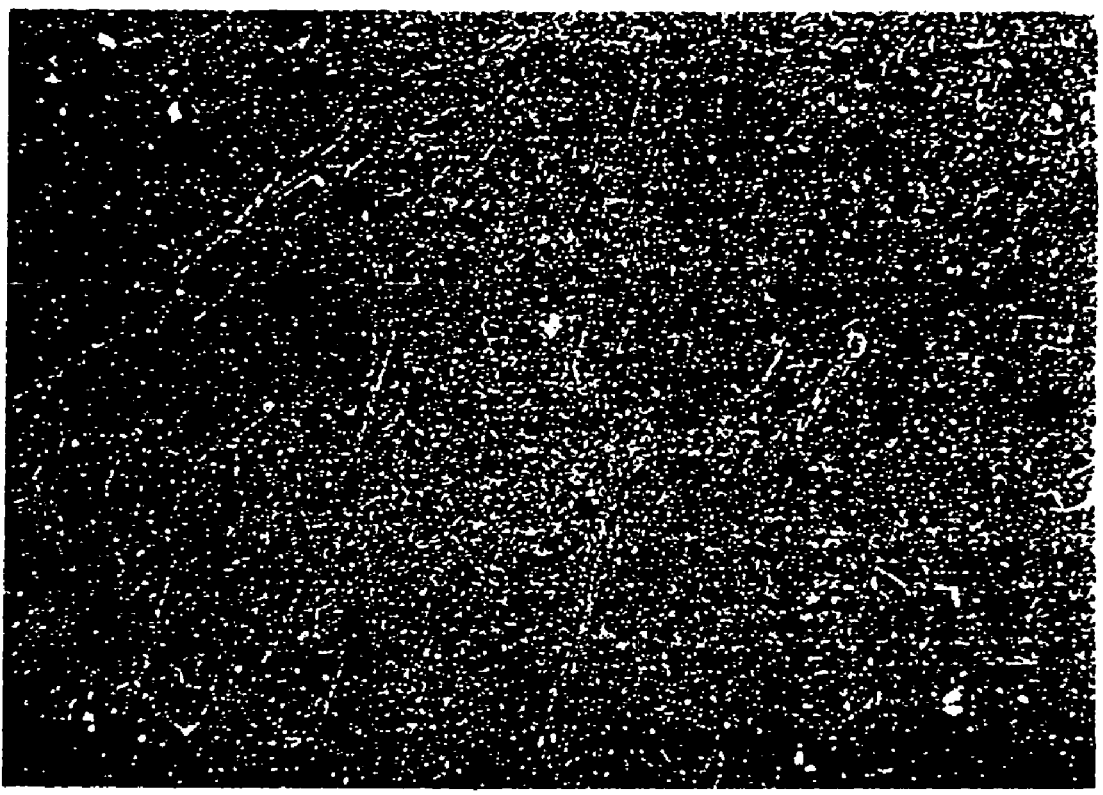

FIG. 9A. Scanning electron micrograph depicting a p-GlcNAc membrane prepared by the acid treatment/neutralization variation of the chemical/biological purification method as described in Section 5.3.2, below. Magnification: 200×.

Figure 9B:

FIG. 9B. Scanning electron micrograph depicting a p-GlcNAc membrane prepared by the acid treatment/neutralization variation of the chemical/biological purification method as described in Section 5.3.2, below. Magnification: 1000×.

Figure 9C:

FIG. 9C. Scanning electron micrograph depicting a p-GlcNAc membrane prepared by the acid treatment/neutralization variation of the chemical/biological purification method as described in Section 5.3.2, below. Magnification: 5000×.

Figure 9D:
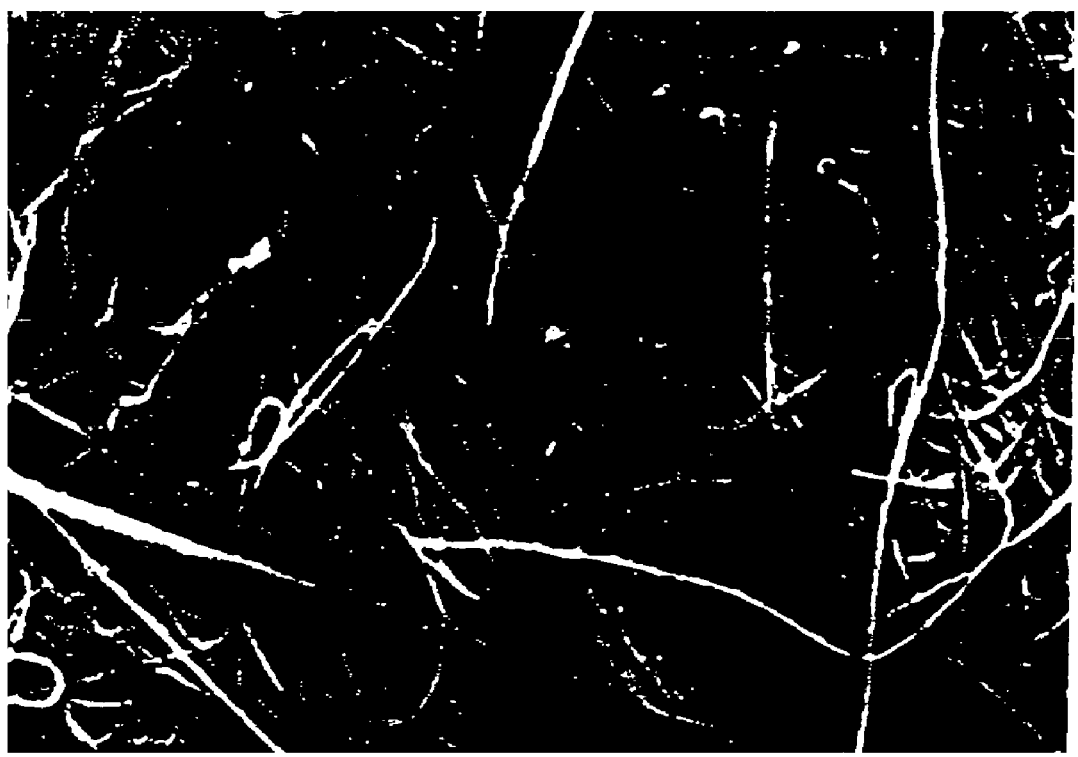

FIG. 9D. Scanning electron micrograph depicting a p-GlcNAc membrane prepared by the acid treatment/neutralization variation of the chemical/biological purification method as described in Section 5.3.2, below. Magnification: 10,000×.

Figure 9E:

FIG. 9E. Scanning electron micrograph depicting a p-GlcNAc membrane prepared by the acid treatment/neutralization variation of the chemical/biological purification method as described in Section 5.3.2, below. Magnification: 20,000×.

Figure 10A:
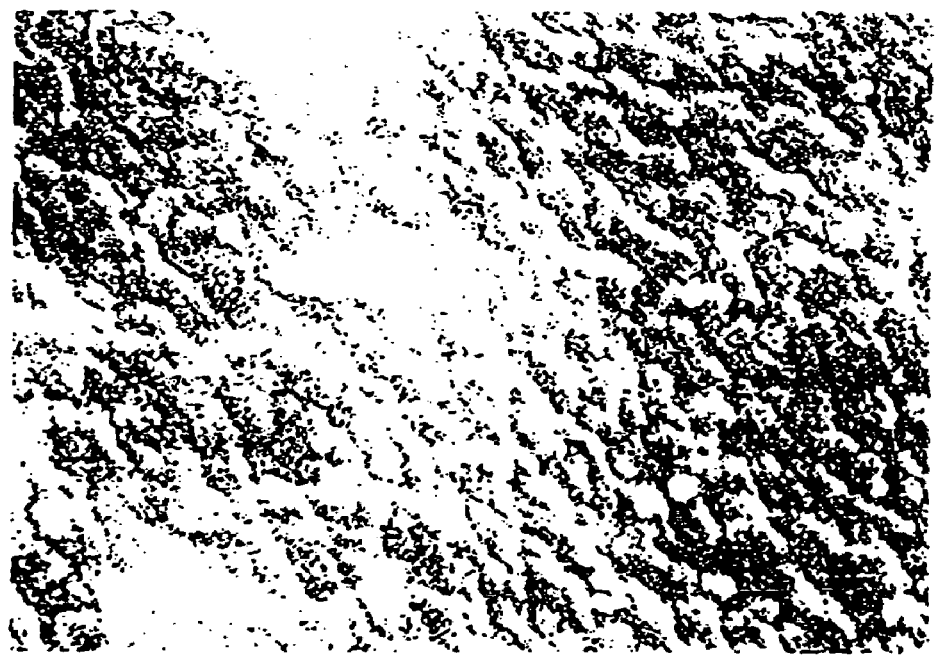
Figure 10B:
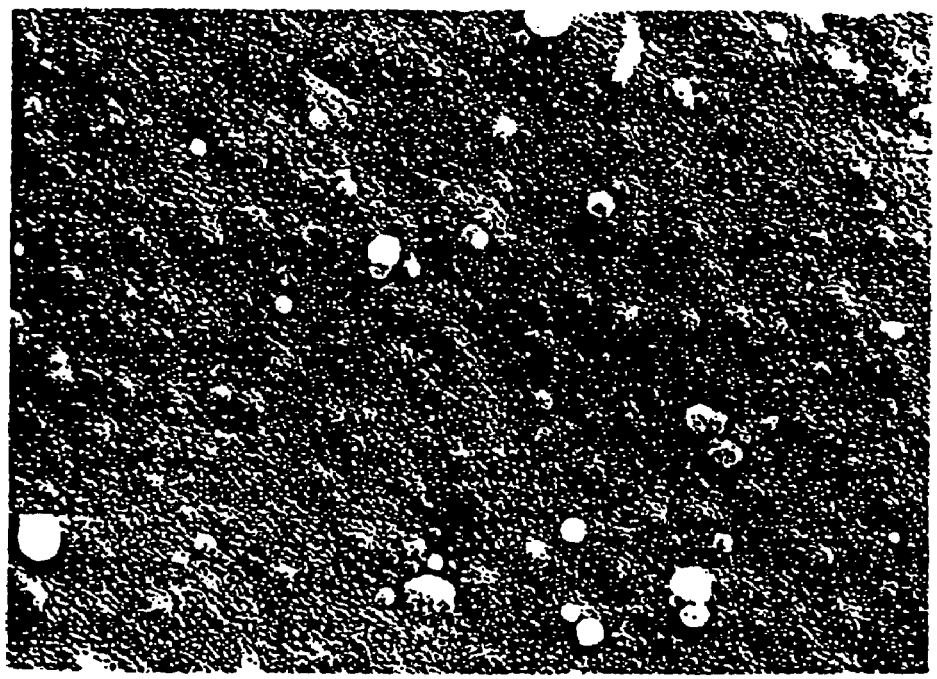

FIGS. 10A–B. Scanning electron micrographs of a pure p-GlcNAc membrane made from material which was initially produced using the cell dissolution/neutralization purification method described in Section 5.3, below, dissolved in dimethylacetamide/lithium chloride, and reprecipitated in $H_2O$ into a mat, as described below in Section 5.5. Magnification: (FIG. 10A), 1000×, (FIG. 10B), 10,000×.

Figure 11A:
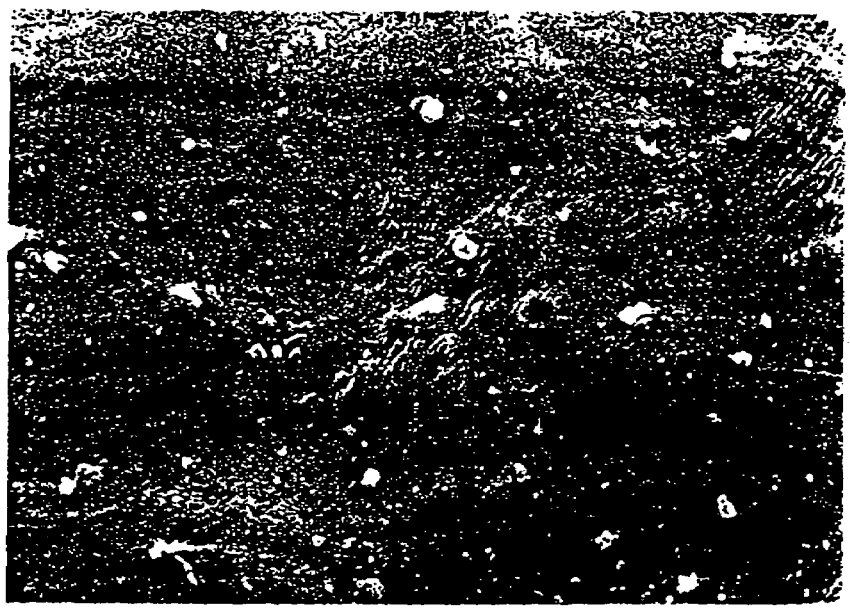
Figure 11B:
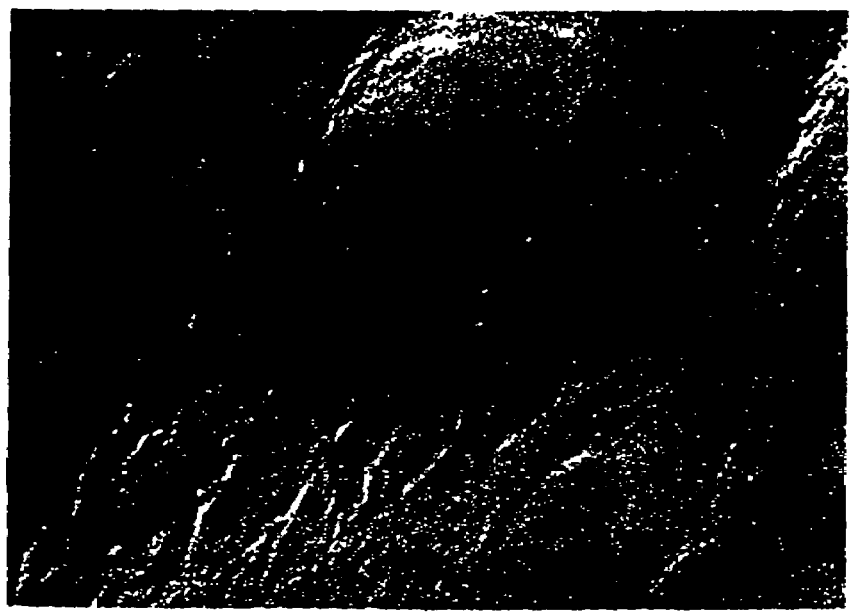

FIGS. 11A–B. Scanning electron micrographs of a deacetylated p-GlcNAc mat. Magnification: (FIG. 11A), 1000×, (FIG. 11B), 10,000×.

Figure 12A:
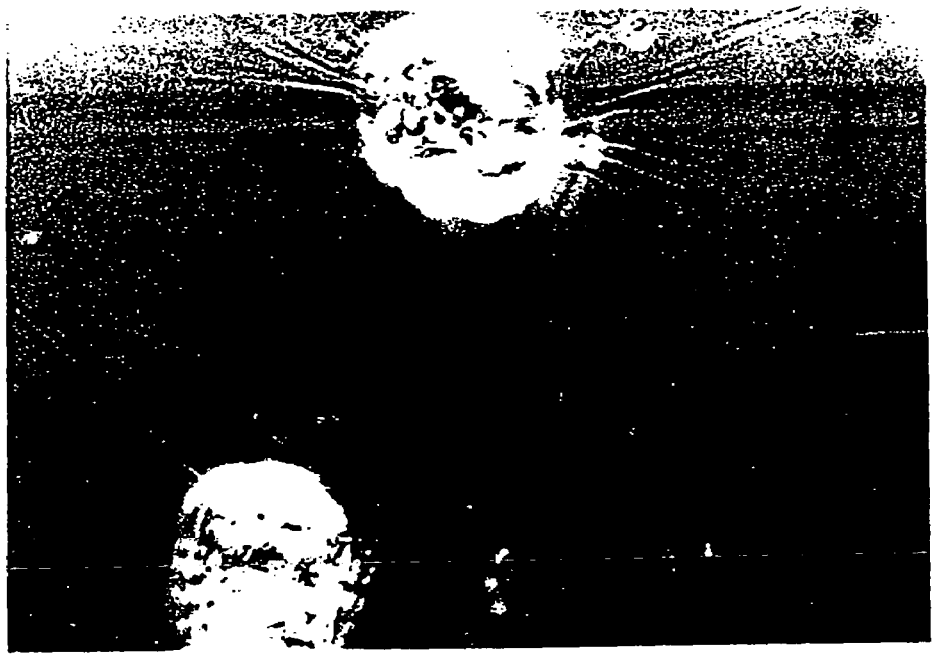
Figure 12B:

FIGS. 12A–B. Photographs of diatoms. Note the p-GlcNAc fibers extending from the diatom cell bodies.

Figure 13:
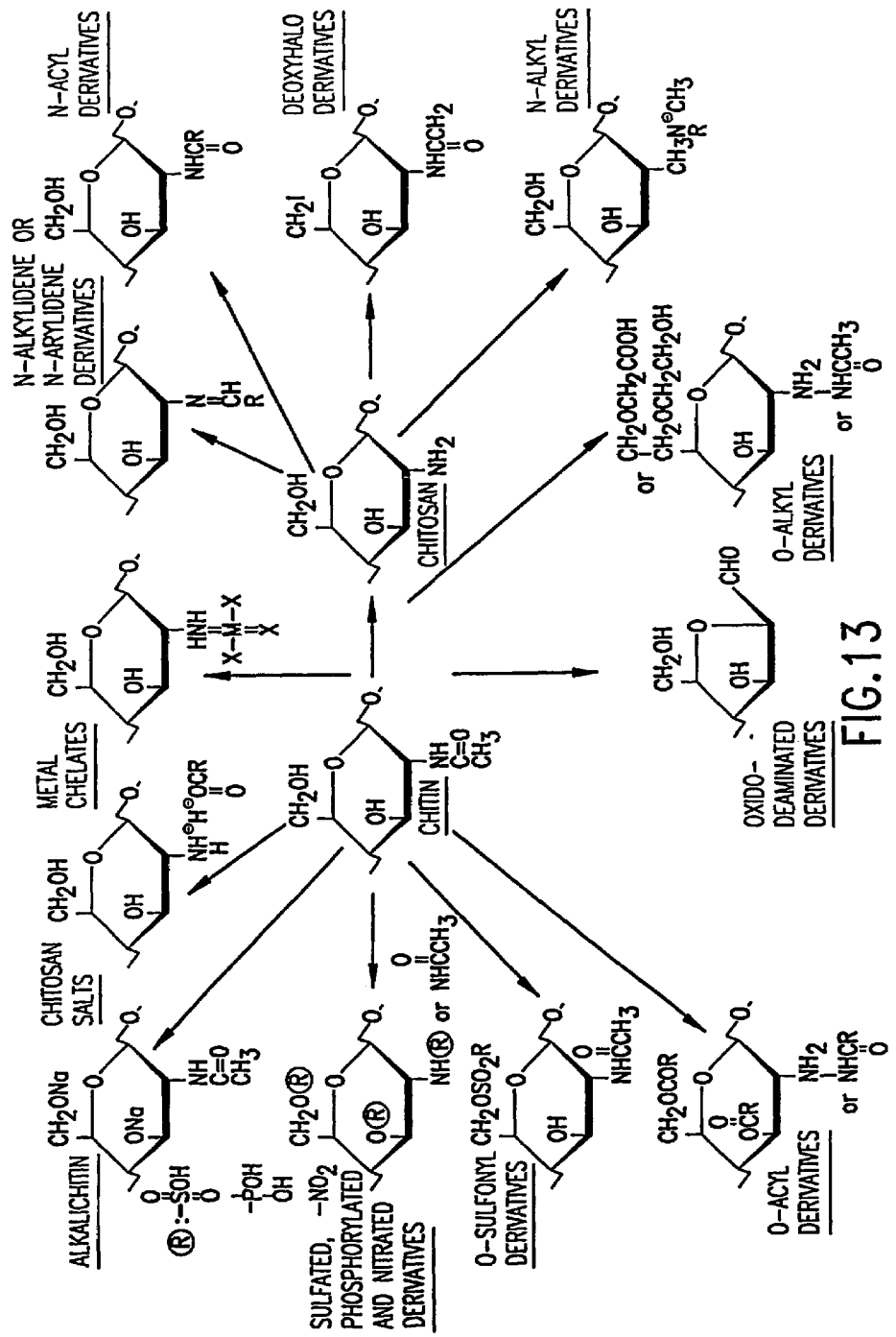

FIG. 13. Diagram depicting some of the possible p-GlcNAc and deacetylated derivatives of the p-GlcNAc starting material. (Adapted from S. Hirano, "Production and Application of Chitin and Chitosan in Japan", in "Chitin and Chitosan," 1989, Skjak-Braek, Anthonsen, and Sanford, eds. Elsevier Science Publishing Co., pp. 37–43.)

Figure 14:
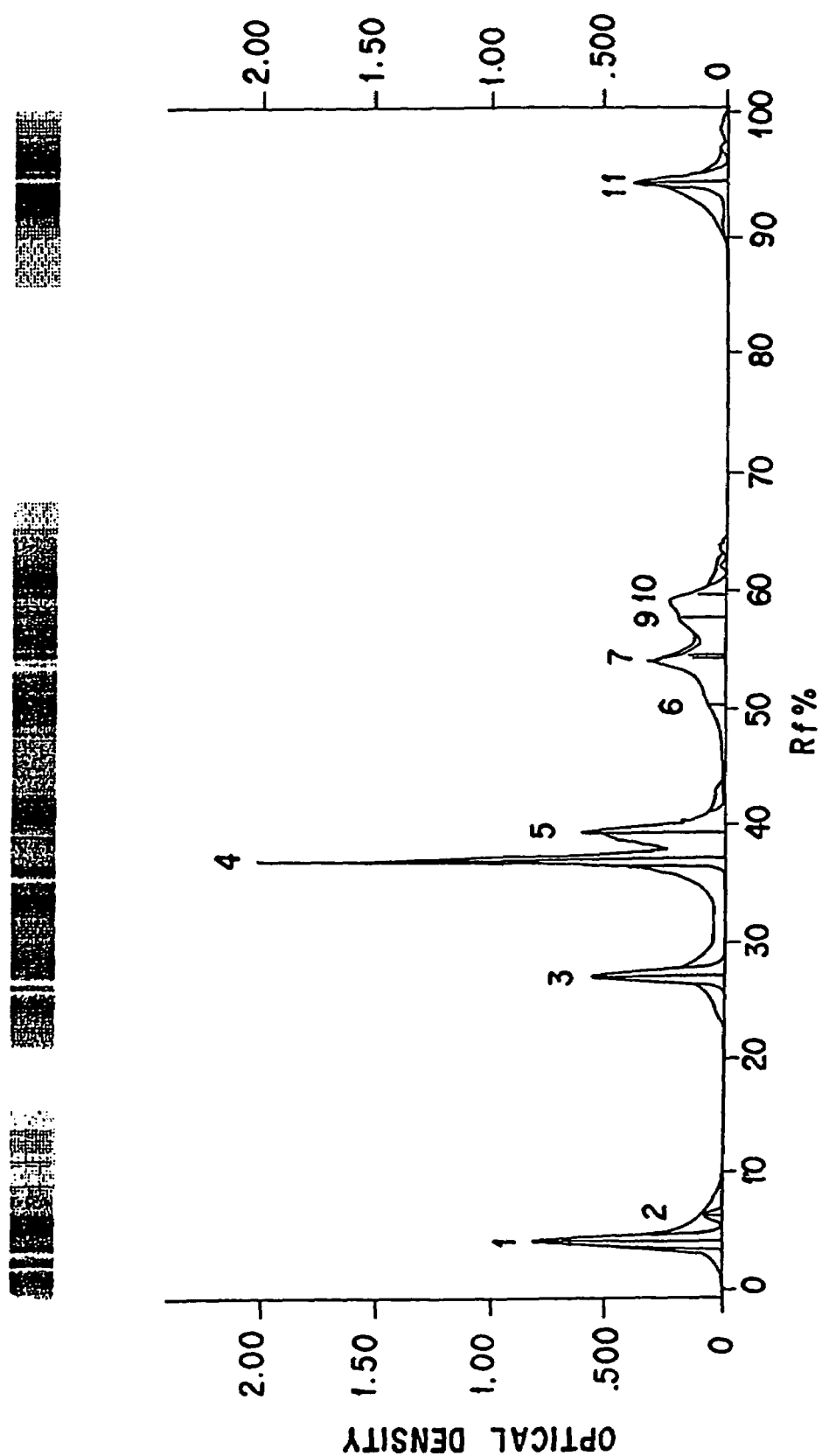

FIG. 14. Transformed NMR data curves, used to obtain areas for each carbon atom and to then calculate the $CH_3$ (area) to C-atom(area) ratios.

Figure 15:
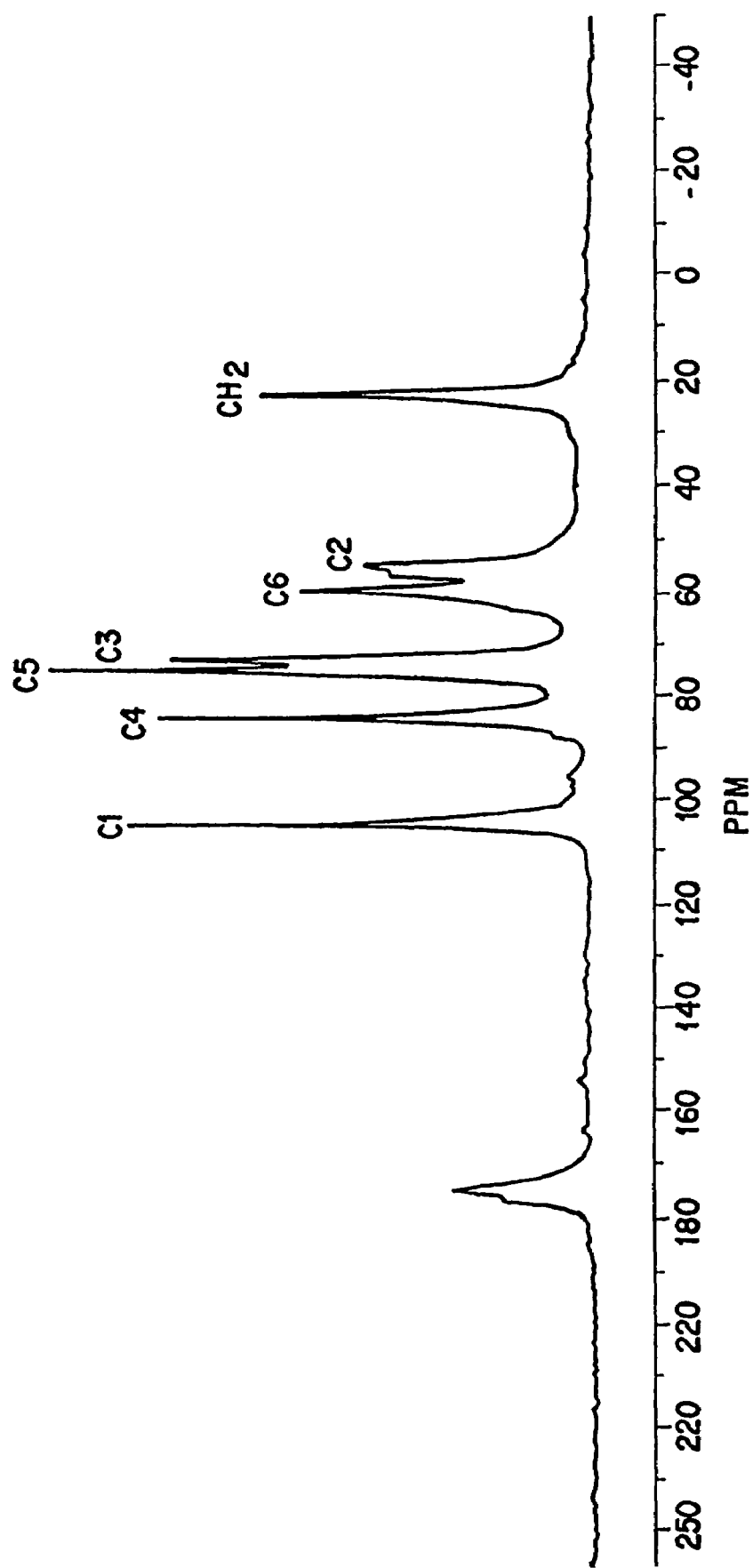

FIG. 15. Typical p-GlcNAc $C^{13}$-NMR spectrum. The individual peaks represent the contribution to the spectrum of each unique carbon atom in the molecule.

Figure 16:
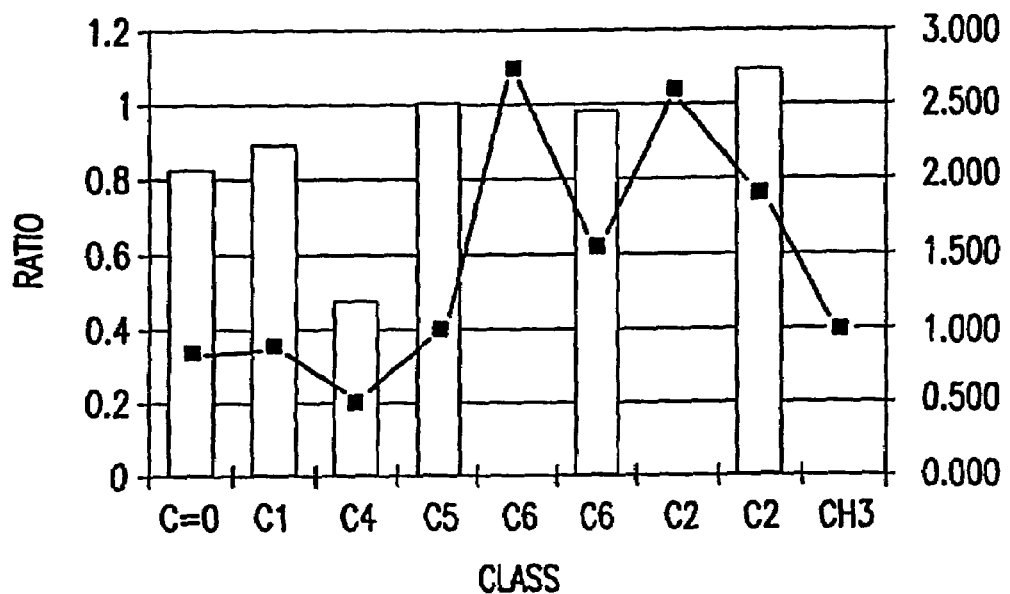

FIG. 16. Transformed NMR spectrum data representing values calculated for $CH_3$(area) to C-atom(area) ratios. Top: Graphic depiction of data; bottom: numerical depiction of data.

Figure 17A:
Figure 17B:
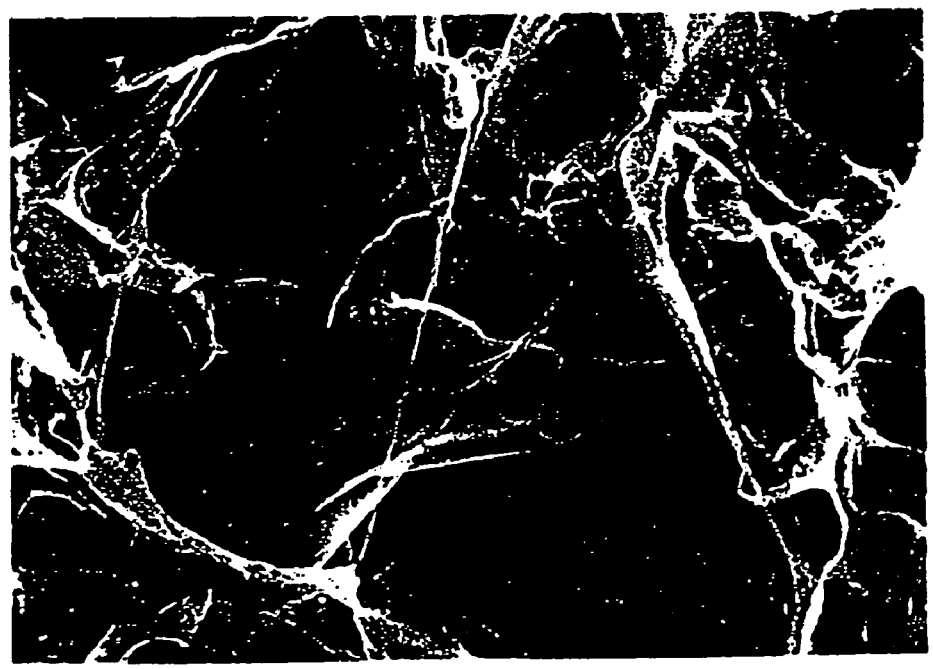
Figure 17C:
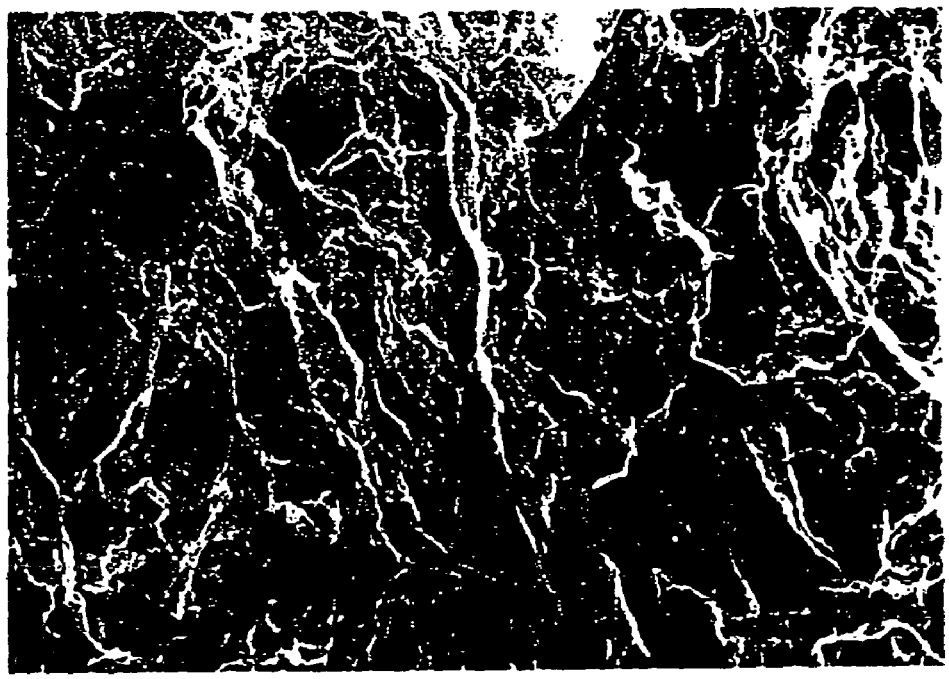
Figure 17D:
Figure 17E:
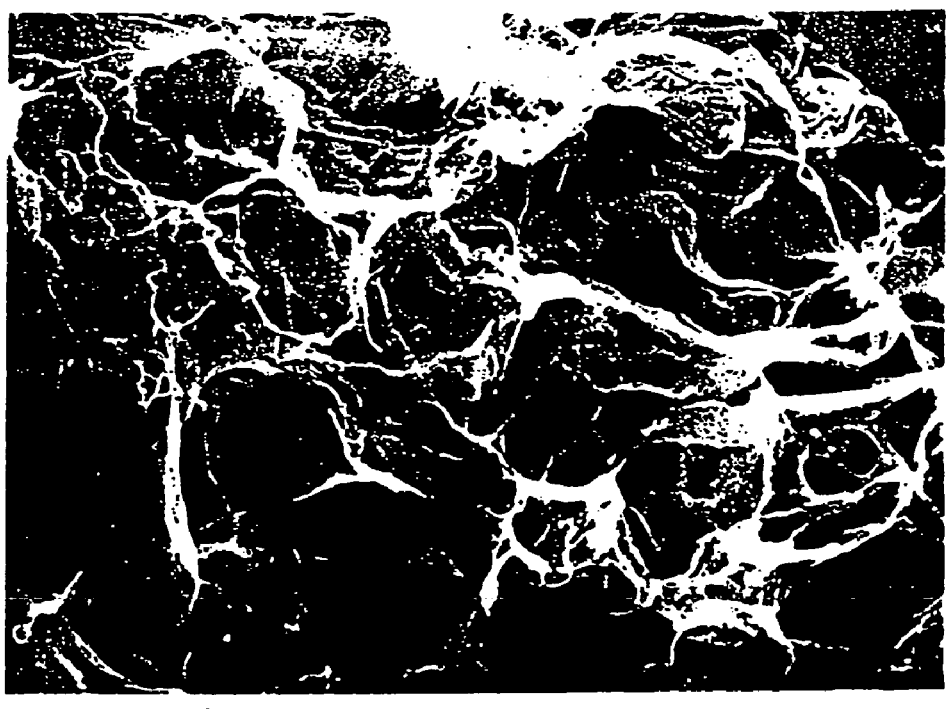
Figure 17F:
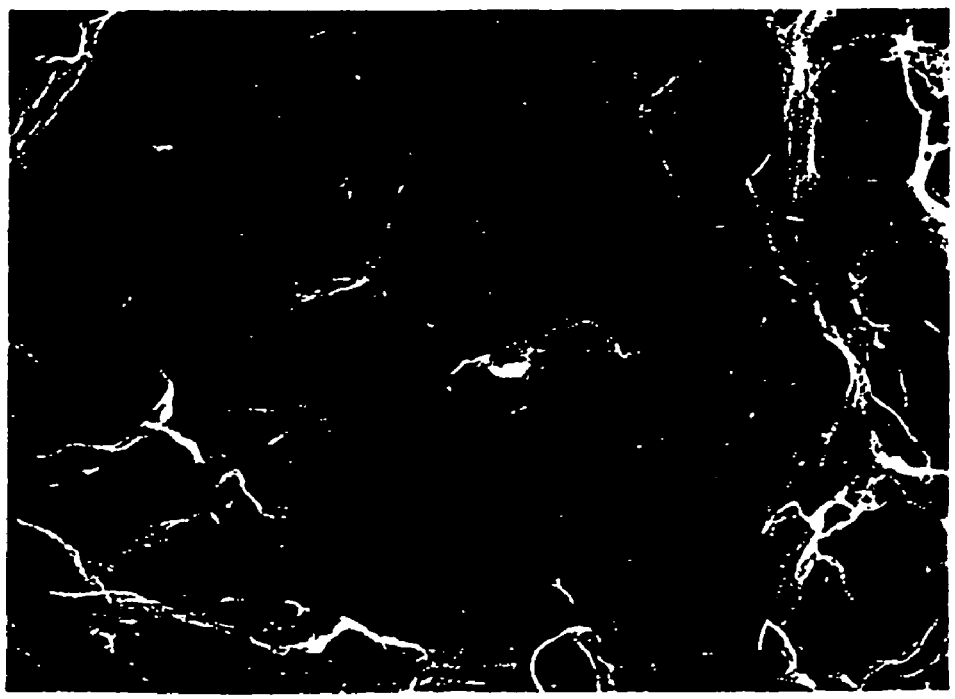
Figure 17G:
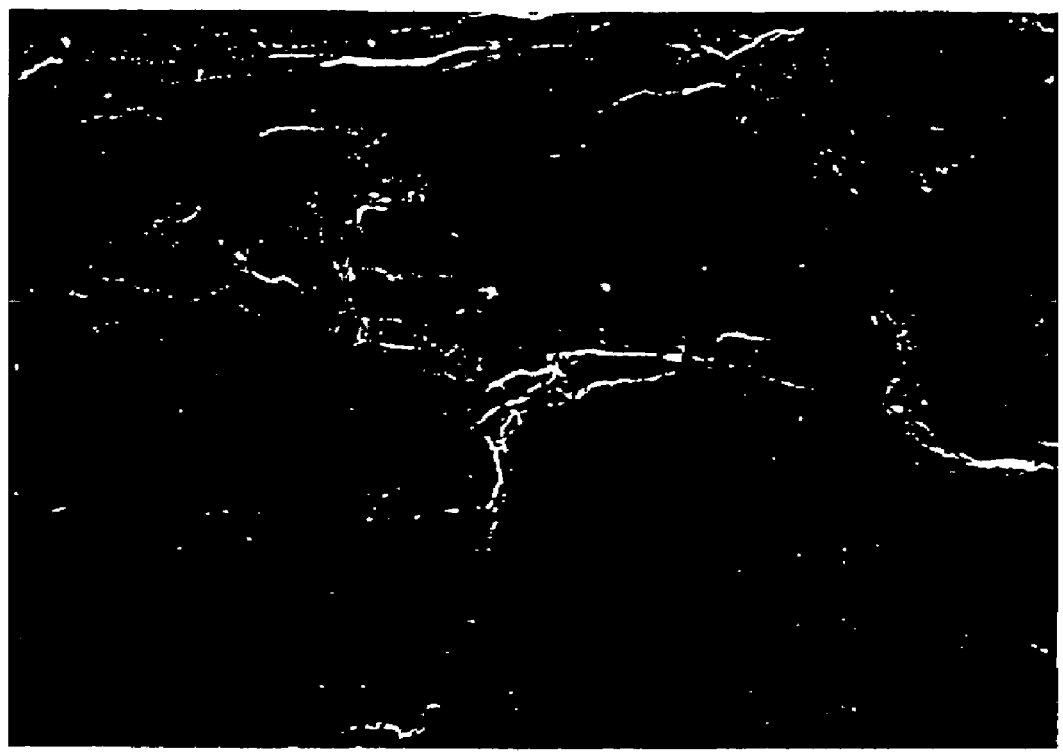

FIGS. 17A–G. Three-dimensional p-GlcNAc matrices produced in various solvents. Specifically, the p-GlcNAc matrices were produced in distilled water (FIG. 17A, FIG. 17D), 10% methanol in distilled water (FIG. 17B), 25% methanol in distilled water (FIG. 17C), 10% ethanol in distilled water (FIG. 17E), 25% ethanol in distilled water (FIG. 17F) and 40% ethanol in distilled water (FIG. 17G). Magnification: 200×. A scale marking of 200 microns is indicated on each of these figures.

Figure 18:
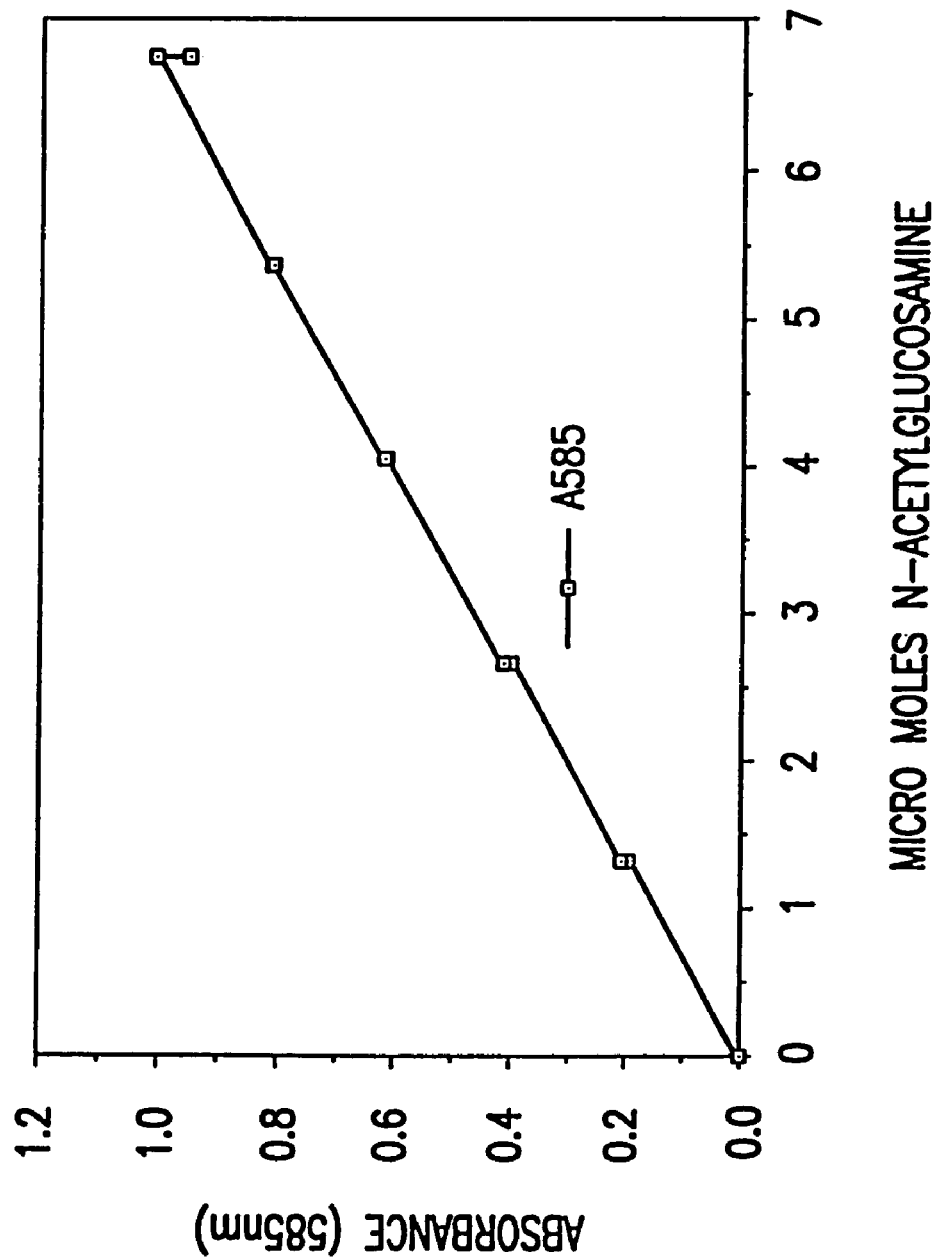

FIG. 18. A typical standard curve obtained using the procedure described, below, in Section 18.1. A standard curve such as this one was used in the lysozyme-chitinase assay also described, below, in Section 18.1.

Figure 19:
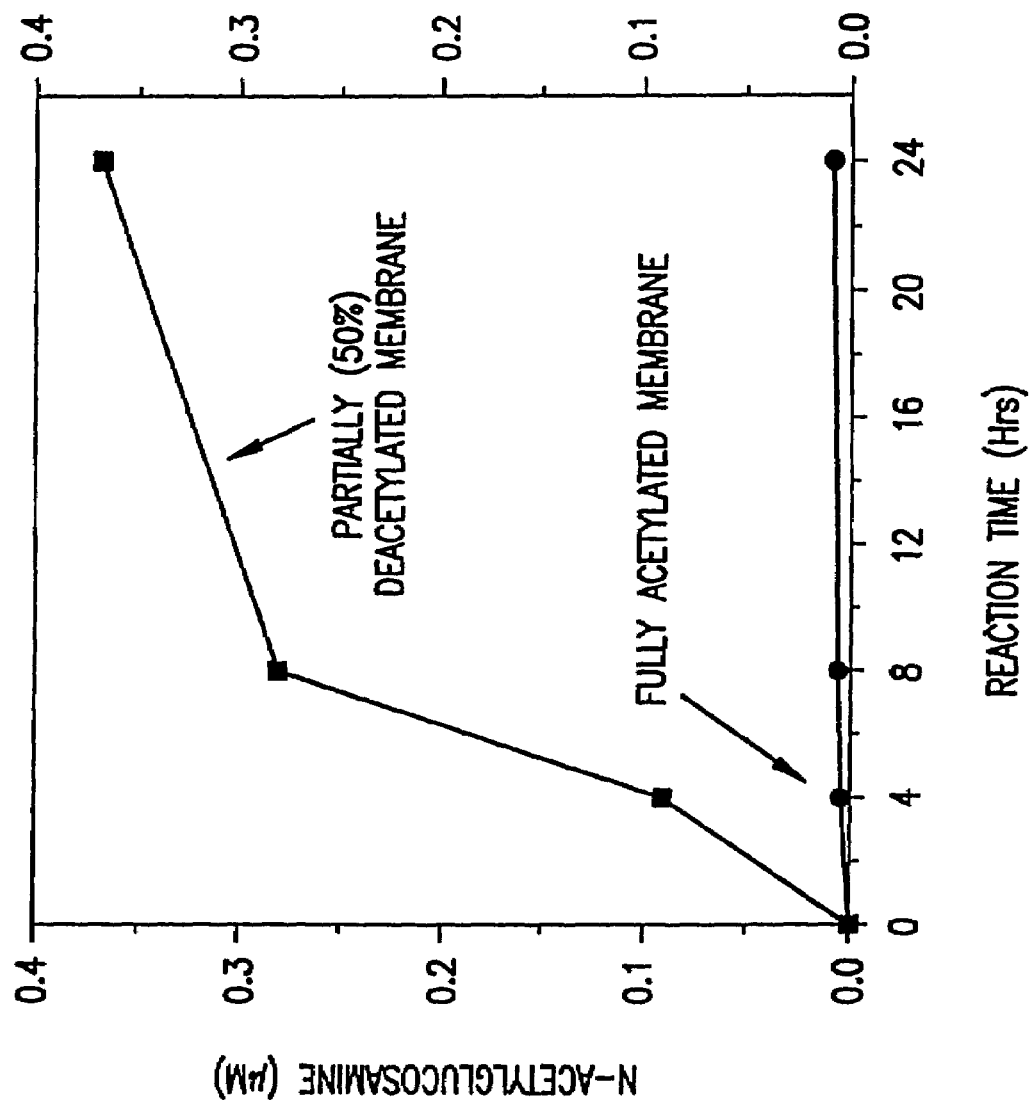

FIG. 19. p-GlcNAc lysozyme digestion data. The graph presented here depicts the accumulation of N-acetylglucosamine over time, as p-GlcNAc membranes are digested with lysozyme. The graph compares the degradation rate of fully acetylated p-GlcNAc to partially (50%) deacetylated p-GlcNAc, and demonstrates that the degradation rate for the partially deacetylated p-GlcNAc was substantially higher than that of the fully acetylated p-GlcNAc material.

Figure 20:
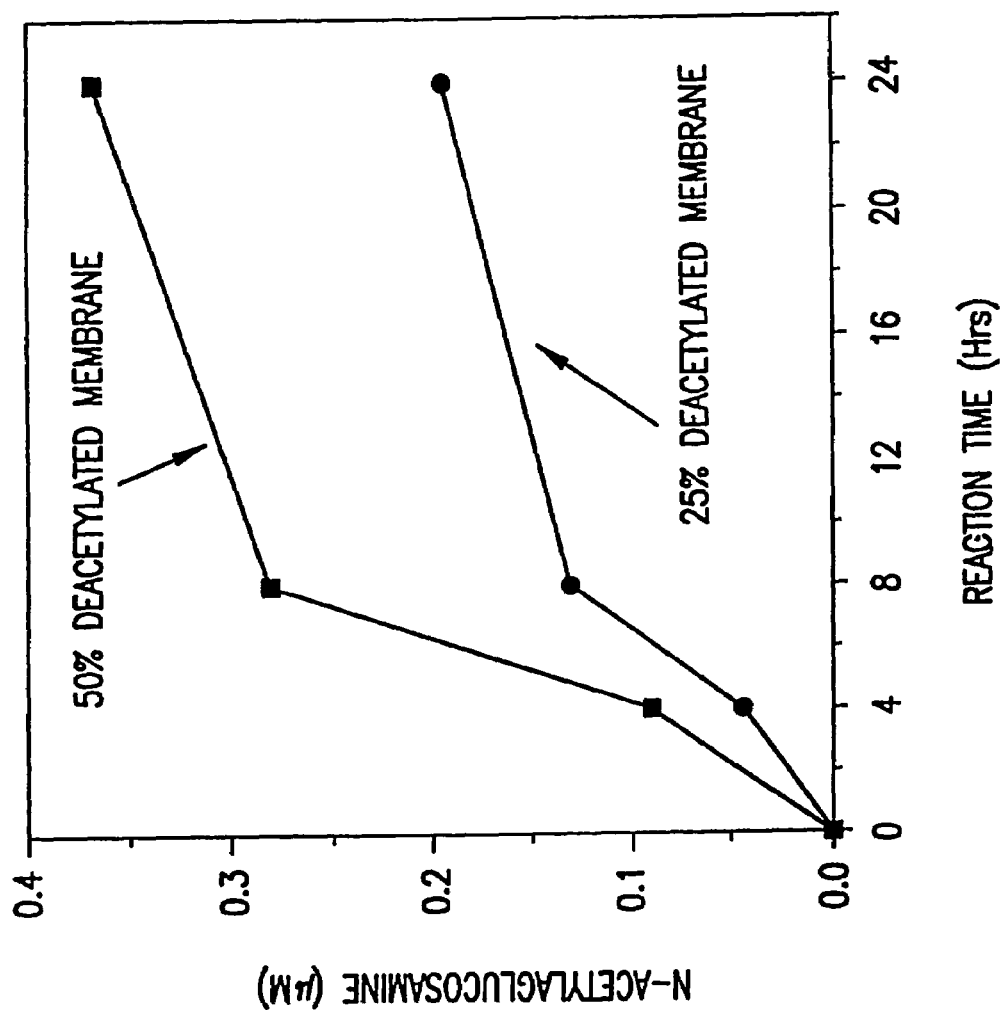

FIG. 20. p-GlcNAc lysozyme digestion data. The graph presented here depicts the accumulation of N-acetylglucosamine over time, as p-GlcNAc membranes are digested with lysozyme. The graph compares the degradation rate of two partially deacetylated p-GlcNAc membranes (specifically a 25% and a 50% deacetylated p-GlcNAc membrane). The data demonstrate that the degradation rate increases as the percent of deacetylation increases, with the degradation rate for the 50% deacetylated p-GlcNAc membrane being substantially higher than that of the 25% deacetylated p-GlcNAc membrane.

Figure 21A:
Figure 21B:
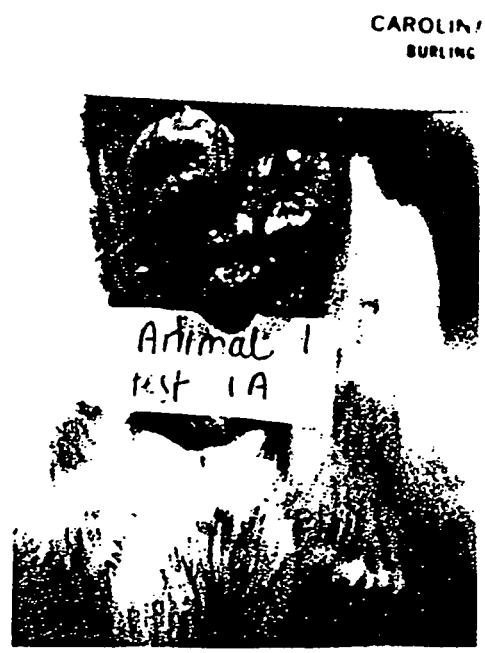
Figure 21C:
Figure 21D:
Figure 21E:
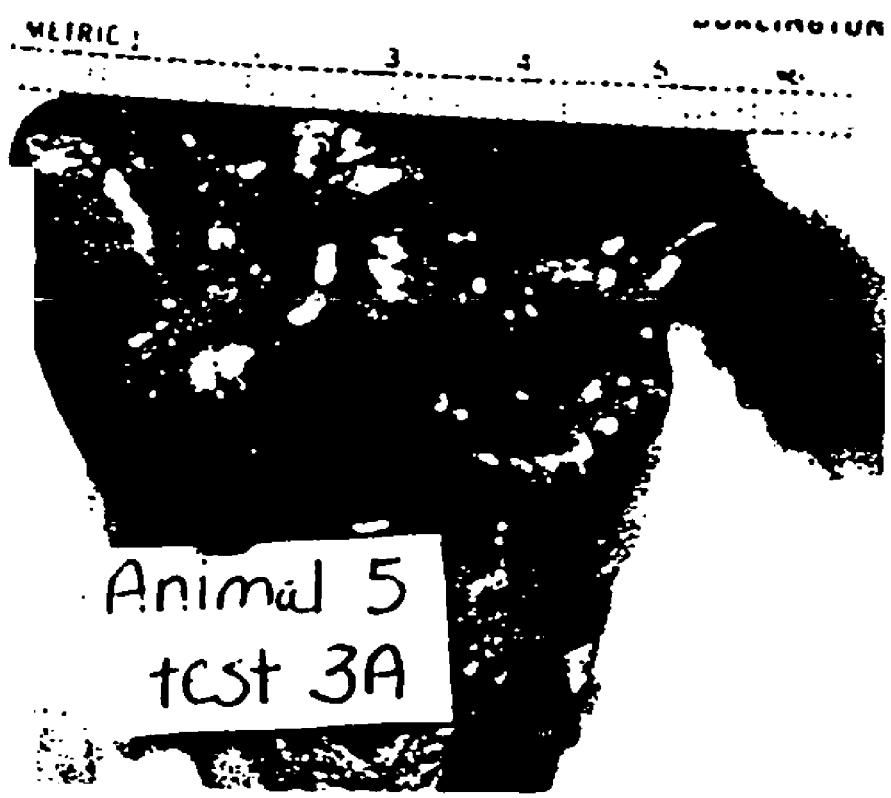

FIGS. 21A–21E. p-GlcNAc in vivo biodegradability data. FIGS. 21A–21C depict rats which have had prototype 1 (fully acetylated p-GlcNAc) membrane abdominally implanted, as described, below, in Section 18.1. FIG. 21A shows a rat at day 0 of the implantation; FIG. 21B shows a rat at day 14 post-implantation; FIG. 21C shows a rat at day 21 post-implantation. FIGS. 21D–21E depict rats which have had prototype 3A (lyophilized and partially deacetylated p-GlcNAc membrane) abdominally implanted, as described, below, in Section 18.1. FIG. 21D shows a rat at day 0 of the implantation; FIG. 21E shows a rat at day 14 post-implantation.

FIGS. 22A–22B. Dose-dependent vasoconstriction of isolated aortic rings by p-GlcNac, either with an intact endothelial layer FIG. 22A, or after removal of the endothelial layer, FIG. 22B. The number of contraction measurements that were averaged to provide the values reported at each concentration of p-GlcNac tested, either with or without an intact endothelial layer, is indicated within the figure, above each p-GlcNAc concentration tested.

Figure 23:
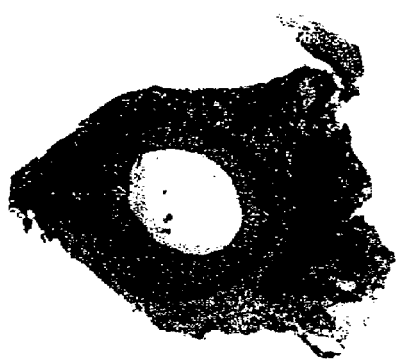
Figure 23:
Figure 23:
Figure 23:
Figure 23:

FIGS. 23A–E. Arterial vasoconstriction by p-GlcNac. FIG. 23(A) depicts a cross-section of a porcine artery obtained 60 minutes after application of a gauze dressing to one side of the artery. FIG. 23(B) depicts a cross-section of a porcine artery obtained 15 minutes after application of a p-GlcNac membrane to one side of the artery. FIG. 23 (C) depicts a cross-section of a porcine artery obtained 60 minutes after application of a p-GlcNac membrane to one side of the artery. FIG. 23(D) depicts a cross-section of a porcine artery obtained 15 minutes after application of a fibrin-coated collagen dressing to one side of the artery. FIG. 23 (E) depicts a cross-section of a porcine artery obtained 60 minutes after application of a fibrin-coated collagen dressing to one side of the artery.

Figure 24:
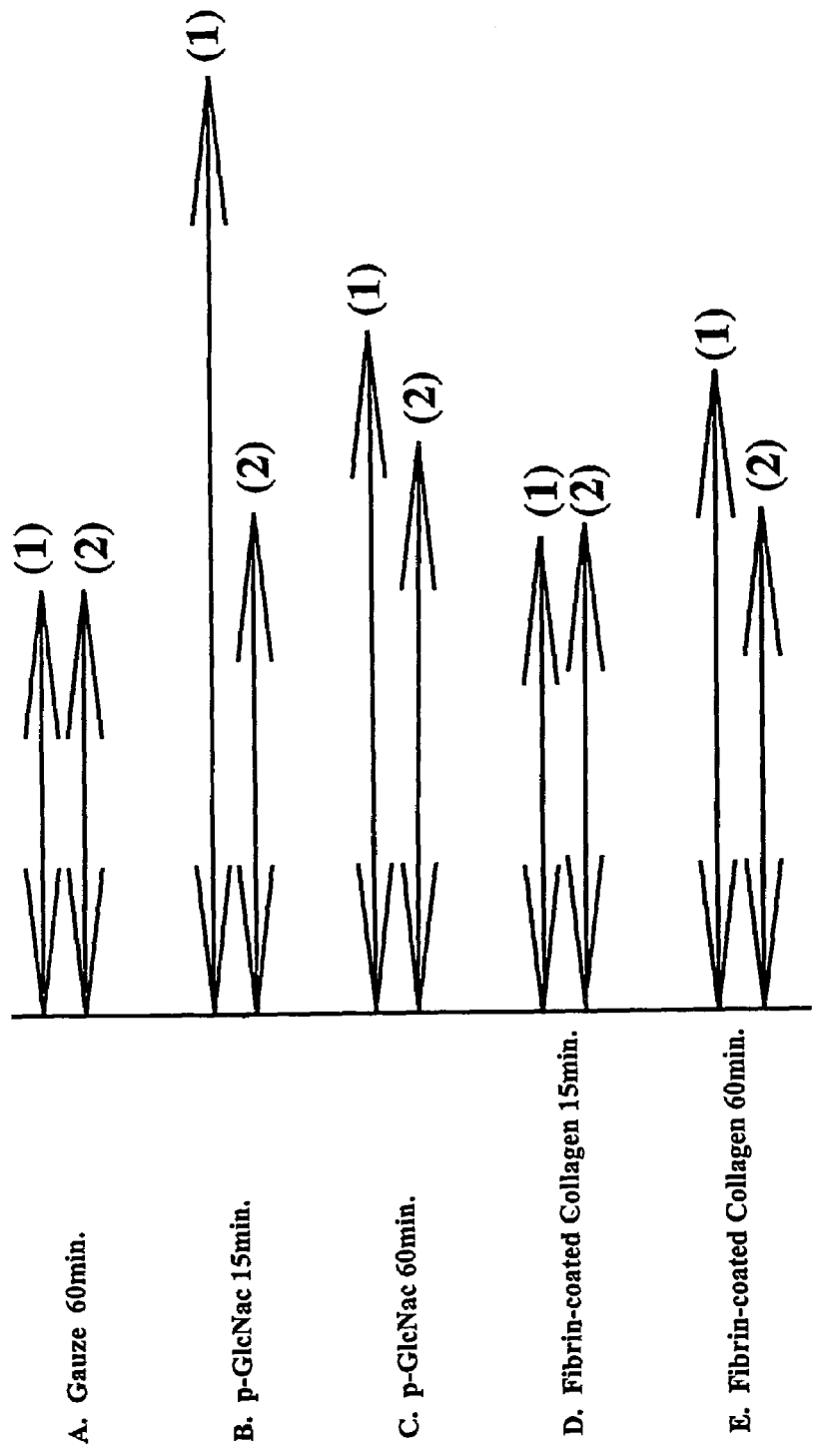

FIG. 24 Arterial vasoconstriction by p-GlcNac. FIG. 24 depicts the thickness of a porcine arterial wall that either was (1), or was not (2), in direct contact with the material tested, for 15 or 60 minutes, as indicated. The materials applied to one side of the artery were: (A) gauze dressing; (B) and (C) p-GlcNac membrane; (D) and (E) fibrin-coated collagen dressing.

5 DETAILED DESCRIPTION OF THE INVENTION

The present invention relates to compositions and methods useful for effecting transient, localized modulation of vascular structure and/or function, by, e.g. (1) stimulation of endothelin-1 release, (2) vasoconstriction, and (3) reduction in blood flow out of a breached vessel, comprising topical administration of compositions and materials that comprise semi-crystalline poly-β-1→4-N-acetylglucosamine (p-GlcNac) polysaccharide polymers. Stimulation of endothelin-1 release, vasoconstriction, and reduction in blood flow out of a breached vessel in a target tissue may be achieved either by direct application of the materials of the present invention to the target tissue, or by application of those materials to the skin or other organ or tissue surface that is adjacent to or contiguous with the target tissue.

The present invention is therefore, also directed to compositions and methods that contribute to or directly effect cessation of bleeding. Administration of the materials of the invention, which comprise semi-crystalline poly-β-1→4-N-acetylglucosamine polymers, results in stimulation of endothelin-1 release, vasoconstriction, and decrease in blood flow out of a breached vessel. These physiological responses, individually and/or collectively, contribute to or directly effect cessation of bleeding, which may be a capillary, vein, or artery. While not wishing to be bound by a particular theory or mechanism, it is believed that such cessation occurs in a coagulation-independent manner. Moreover, achievement of cessation of bleeding using the compositions and methods of the present invention is also not dependent upon formation of a physical barrier or mechanical matrix that promotes clotting. That is, according to the present invention, the material need not be a barrier-forming material that provides a mechanical matrix that adheres to the site of application and seals the boundaries of the wound. In contrast, the compositions and methods of the present invention induce a transient, localized alteration of vascular structure and/or function, and it is that alteration, which is independent of clot formation, that, per se, contributes to or directly effects cessation of bleeding.

Figure 22:
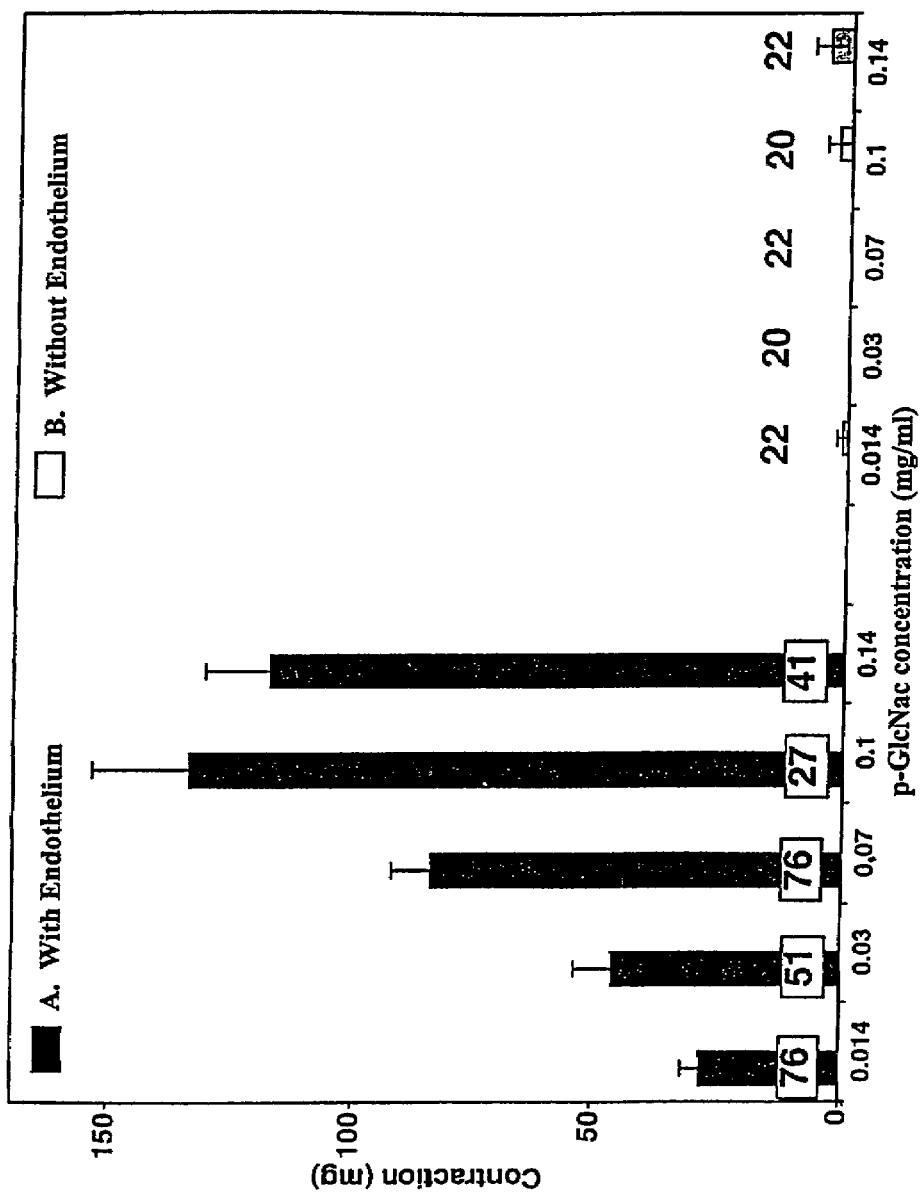

Furthermore, the preferred materials of the compositions and methods of the present invention comprise fully acetylated semi-crystalline poly-β-1→4-N-acetylglucosamine polymers, since, as demonstrated the Examples provided in Sections 16 and 17, as well as FIG. 22, infra, materials comprising 70%-deacetylated poly-β-1→4-N-acetylglucosamine polymers do not induce vasoconstriction and, therefore will not decrease the lumen of the vessel and, consequently, will not reduce blood flow out of a breached vessel.

This invention is based in part on Applicants' discovery that topically-applied materials, which need not be barrier-forming materials, that comprise semi-crystalline poly-β-1→4-N-acetylglucosamine (p-GlcNac) polymers, induce vasoconstriction in isolated Sprague-Dawley rat aortic rings. In this blood-free system, fully acetylated poly-β-1→4-N-acetylglucosamine induced contraction of the isolated aortic rings in a concentration-dependent manner. As demonstrated infra, in the Example presented in Section 17, the degree of vasoconstriction obtained was substantially proportional to the concentration of p-GlcNac applied to the isolated aortic ring. In contrast, 70% deacetylated poly-β-1→4-N-acetylglucosamine, did not induce vasoconstriction of the isolated aortic rings, at any concentration tested.

This invention is also based in part on Applicants' discovery that in vivo application of membrane membranes, which are formed from semi-crystalline poly-β-1→4-N-acetylglucosamine polymers, to experimental wounds in arteries, stimulated immediate vasoconstriction at the site of contact between the arterial tissue and the applied membrane. Histological analysis of treated tissue revealed that arterial constriction was greater on the side where the membrane was applied than on the opposite side of the artery. Furthermore, immunochemical analyses of these tissue samples also revealed the presence of a concentration gradient of endothelin-1 release, i.e., stimulation of endothelin-1 release was a localized physiological response. The extent of the stimulation of endothelin-1 release was greatest at the surface contacted by the semi-crystalline poly-β-1→4-N-acetylglucosamine polymer containing-membrane, and extended into adjacent tissue, although to an extent that decreased as the distance from the contact surface increased. A similar, localized stimulation of endothelin-1 release was observed in spleen tissue contacted with material comprising semi-crystalline poly-β-1→4-N-acetylglucosamine.

The methods of the present invention comprise topical administration of materials comprising a therapeutically effective form and a therapeutically effective amount of semi-crystalline poly-β-1→4-N-acetylglucosamine polymers, to a patient in order to achieve transient, localized: (1) enhancement of endothelin-1 release, (2) vasoconstriction, and/or (3) reduction of blood flow out of a breached vessel.

Presented below, is, first, a description of physical characteristics of the purified p-GlcNac starting material, and of its reformulations. Next, methods are described for the purification of the p-GlcNac starting material from microalgae, preferably diatom, starting sources. Third, reformulations of the p-GlcNac, and methods for the production of such reformulations are presented. Finally, uses are presented for the p-GlcNAc, p-GlcNAc derivatives and/or p-GlcNac reformulations of the starting material.

5.1. p-GlcNac

The p-GlcNac starting material can be made using techniques described herein, coupled with the teaching provided in U.S. Pat. Nos. 5,686,115, 5,624,679, 5,623,064, and 5,622,834, each of which is hereby incorporated by reference in its entirety. The p-GlcNac polymers used herein comprise about 50 to about 150,000 N-acetylglucosamine monosaccharides (FIG. 1). The purity of the p-GlcNac starting material is very high, as evidenced by chemical and physical criteria. Among these are chemical composition and non-polysaccharide contaminants. First, chemical composition data for the p-GlcNac produced using two different purification methods, both of which are described in Section 5.3, below, is shown in Table I below. As can be seen, the chemical composition of the p-GlcNac produced by both methods is, within the bounds of experimental error, the same as the formula compositions of p-GlcNac. Second, as is also shown in Table I, the p-GlcNac produced is free of detectable protein contaminants, is substantially free of other organic contaminants such as free amino acids, and is substantially free of inorganic contaminants such as ash and metal ions (the p-GlcNac starting material may deviate up to about 2% from the theoretical values of carbon, hydrogen, nitrogen and oxygen for pure p-GlcNac). Therefore, as used herein, the terms "substantially free of organic contaminants" and "substantially free of inorganic contaminants" refer to compositions of p-GlcNac having the profiles for carbon, hydrogen, nitrogen and oxygen which deviate no more than about 2% from the theoretical values, and preferably, the p-GlcNac starting material contain a profile as exemplified in the Experimental Data on p-GlcNac mats in Table I (allowing for the percent deviation). Further, the p-GlcNac starting material exhibits a low percentage of bound water.

TABLE I

CHEMICAL ANALYSIS DATA (% by weight)
Theoretical Values for Pure p-GlcNac:
Carbon - 47.29
Hydrogen - 6.40
Nitrogen - 6.89
Oxygen - 39.41
Protein - 0.00
Experimental Data on p-GlcNac Mats:
(Number of experimental batches for each membrane type being greater than 30 for each membrane type)

|  | MECHANICAL FORCE METHOD | | CHEMICAL/BIOLOGICAL METHOD | |
|---|---|---|---|---|
|  | Normalized[1] | % Dev. | Normalized[1] | % Dev. |
| Carbon | 47.21 ± 0.08 | −0.17 | 47.31 ± 0.01 | +0.04 |
| Hydrogen | 6.45 ± 0.08 | +0.78 | 6.34 ± 0.08 | −0.94 |
| Nitrogen | 6.97 ± 0.18 | +0.87 | 6.94 ± 0.16 | +0.73 |
| Oxygen | 39.55 ± 0.36 | +0.36 | 39.41 ± 0.10 | 0.00 |
|  | Average Values | | Average Values | |
| Protein | 0.00 | | 0.00 | |
| Ash | 1.30 | | 0.98 | |
| Moisture | 2.0 | | 1.2 | |

[1]Raw analytical data have been normalized to account for ash and moisture content of the samples.

The pure p-GlcNac starting material exhibits a carbohydrate analysis profile substantially similar to that shown in FIG. 2. The primary monosaccharide of the pure p-GlcNac starting material is N-acetylglucosamine. Further, the pure p-GlcNac starting material does not contain the monosaccharide glucosamine.

The circular dichroism (CD) and sharp infra-red spectra (IR) of the p-GlcNac starting material are shown in FIGS. 3A, and FIGS. 4A, 4D, and 4E, respectively, which present analyses of material produced using the methods described in Section 5.3, below. Such physical data corroborates that the p-GlcNac starting material is of high purity and semi-crystalline. The phrase "semi-crystalline" refers to the highly ordered nature of the material. One of skill in the art would readily appreciate that the sharp, well resolved peaks observed in the infra-red spectra of the p-GlcNAc polymers of the present invention reflect the highly ordered, crystalline nature of the material (i.e. "semi-crystalline") examined. That artisan would also appreciate that broadened, poorly resolved peaks in such a IR spectra, as for example depicted in FIGS. 4B and 4C, would indicate loss or lack of a semi-crystalline nature. The methods used to obtain the CD and IR data are described, below, in the Working Example presented in Section 6.

NMR analysis of the pure p-GlcNac starting material exhibits a pattern substantially similar to that seen in FIGS. 5A, 14, 15 and 16. Such an NMR pattern indicates not only data which is consistent with the p-GlcNac starting material being a fully acetylated polymer, but also demonstrates the lack of contaminating organic matter within the p-GlcNac species. The electron micrographic structure of the p-GlcNac starting material, as produced using the methods described in Section 5.3, below and demonstrated in the Working Examples presented below in Section 8 and 9, is depicted in FIG. 6 through FIG. 9E.

The p-GlcNac starting material exhibits a high degree of biocompatability. Biocompatability may be determined by a variety of techniques, including, but not limited to such procedures as the elution test, intramuscular implantation, or intracutaneous or systemic injection into animal subjects. Briefly, an elution test (U.S. Pharmacopeia XXII, 1990, pp. 1415–1497; U.S. Pharmacopeia XXII, 1991, Supplement 5, pp. 2702–2703) is designed to evaluate the biocompatibility of test article extracts, and assays the biological reactivity of a mammalian cell culture line which is sensitive to extractable cytotoxic articles (such as, for example, the L929 cell line) in response to the test article. The Working Example presented in Section 10, below, demonstrates the high biocompatibility of the p-GlcNac starting material.

5.2. Methods of Producing Microalgal Sources of p-GlcNac 5.2.1. Microalgal Sources of p-GlcNac The p-GlcNac starting material is produced by, and may be purified from, microalgae, preferably diatoms. The diatoms of several genuses and numerous species within such genuses may be utilized as p-GlcNac starting sources. Each of these diatoms produce p-GlcNac. See FIGS. 12A–B for photographs of such diatoms. The diatoms which may be used as starting sources for the production of the p-GlcNac starting material include, but are not limited to members of the *Coscinodiscus* genus, the *Cyclotella* genus, and the *Thalassiosira* genus, with the *Thalassiosira* genus being preferred.

Among the *Coscinodiscus* genus, the species of diatom that may be used to produce the p-GlcNac starting material include, but are not limited to the *concinnus* and *radiatus* species. The diatoms among the *Cyclotella* genus which may be used include, but are not limited to the *caspia, cryptica*, and *meneghiniana* species. The *Thalassiosira* diatoms that may be utilized to produce the starting material for the p-GlcNac starting material include, but are not limited to the *nitzschoides, aestivalis, antarctica, deciphens, eccentrica, floridana, fluviatilis, gravida, guillardii, hyalina, minima, nordenskioldii, oceanica, polychorda, pseudonana; rotula, tubifera, rumida*, and *weissflogii* species, with the *fluviatilis* and *weissflogii* species being preferred.

Diatoms such as those described above may be obtained, for example, from the culture collection of the Bigelow Laboratory for Ocean Sciences, Center for Collection of Marine Phytoplankton (McKown Point, West Boothbay Harbor, Me., 04575).

5.2.2. Methods for Growing Diatoms

Any of the diatoms described in Section 5.2.1, above, may be grown by utilizing, for example, the methods described in this section. New diatom cultures are initiated by inoculating, under aseptic conditions, Nutrient Medium with an aliquot of a mature diatom culture. The Nutrient Medium must be free of all other microorganisms, therefore all materials, including water, organic components, and inorganic components used in the preparation of the Nutrient Medium must be sterile. In addition, it is mandatory that all procedures involved in this operation be conducted under strictly aseptic conditions, i.e., all containers, all transfers of substances from one vessel to another, etc. must be performed in a sterile environment. The quantity of Nutrient Medium to be prepared at one time should not exceed what is necessary to start a new culture. For example, Fembach flasks which occupy approximately one square foot of surface may be used as vessels for the diatom cultures, and such vessels require one liter of Nutrient Medium for optimum growth of the diatom organism.

Preparation of the nutrient medium involves the following operations:

a) Acquisition and processing of seawater
b) Preparation of distilled and deionized water
c) Preparation of primary nutrient stocks
d) Preparation of nutrient working stocks
e) Preparation of the final nutrient medium Filtered seawater may be obtained, for example, from the Marine Biology Laboratory (Woods Hole, Mass.). Seawater containers should be stored at 5° C. (±2° C.). When required, the necessary volume of water may be filtered through a Buchner filtration unit, using a Supor-800 polyether sulfone filter membrane with 0.8 micron pore size (Gelman, Inc.). The seawater is then sterilized by autoclaving at, for example, 121° C. for at least about 15 minutes per liter. On completion of the sterilization process, the capped flasks are immediately cooled, preferably by transfer to a cold room capable of allowing the solutions to reach a temperature of approximately 5° C. (±2°). When it is to be used, solutions are allowed to reach room temperature.

Tap water is distilled and deionized using standard equipment and procedures, and collected and stored in clean, securely capped, preferably glass, containers.

Listed below are formulas which may be followed in preparing the stock solutions necessary for the preparation of the Nutrient Medium. It is to be understood that while such formulas are to be used as guides, it is intended that routine variations of such formulas which contribute to the preparation of a Nutrient Medium capable of sustaining microalgal diatom growth sufficient for the p-GlcNac preparative processes described here also be within the scope of the present invention.

I. Trace Metal Primary Stocks (TMPS)

a. 39 mM $CuSO_4.5H_2O$ (copper [II] sulfate pentahydrate) (9.8 g copper [II] sulfate/L)

b. 7.5 mM $ZnSO_4.7H_2O$ (Zinc sulfate heptahydrate) (22 g zinc sulfate/L)

c. 42 mM $CoCl_2.6H_2O$ (Cobalt [II] chloride hexahydrate) (10 g cobalt [II] chloride/L)

d. 91 mM $MnCl_2.4H_2O$ (Manganese [II] chloride tetrahydrate) 18 g manganese [II] chloride/L)

e. 26 mM $NaMoO_4.2H_2O$ (Sodium molybdate dihydrate) 6.3 g sodium molybdate/L)

f. 1 mM $H_2SeO_3$ (Selenious acid) (0.129 g selenious acid/L).

Sterile filter each nutrient with a filter of no greater than 0.2 micron pore size.

II. Vitamin Primary Stocks (VPS)

a. 1 mg/ml Vitamin B12b. 0.1 mg/ml Biotin

Sterile filter both stocks with a filter of no greater than 0.2 micron pore size.

III. Sodium Salts Working Stocks (SSWS)

a. Sodium nitrate working stock: 0.88M (75 g $NaNO_3$/L)

b. Sodium phosphate monobasic monohydrate working stock: 36.2 mM $NaH_2PO_4.H_2O$ (5 g $NaH_2PO_4.H_2O$/L). Sodium metasilicate monohydrate working stock: 0.11M $Na_2SiO_3.9H_2O$ (30 g $Na_2SiO_3.9H_2O$/L)Sterile filter each of the SSWS with a filter of no greater than 0.2 micron pore size.

IV. Trace Metal Working Stocks (TMWS)

11.7 mM $Na_2EDTA$ (Ethylenediamine Tetraacetic acid, disodium salt dihydrate) (4.36 g/L)

11.7 mM $FeCl_3.6H_2O$ (Iron [III] chloride hexahydrate) (3.15 g/L)

1 ml/L of each of the six primary trace metal stocks listed above.

Sterile filter with a filter of no greater than 0.2 micron pore size. Note that the trace metal working stock must be prepared fresh weekly.

V. Vitamin Working Stock (VWS)

1.0 µg/ml Biotin (1.0 ml primary Biotin Stock/100 ml)

1.0 µg/ml Vitamin B12 (0.1 ml Vitamin B12 primary stock/100 ml)

0.20 mg/ml of Thiamine HCl (20 mg Thiamine hydrochloride/100 ml).

Sterile filter with a filter of no greater than 0.2 micron pore size. Note that a new Vitamin Working Stock should be prepared fresh weekly.

Described below are techniques which may be followed for the preparation of Nutrient Medium and for diatom culturing. It is to be understood that, in addition to these techniques, any routine variation in the formulas and/or procedures described herein which result in a Nutrient Medium and in procedures capable of sustaining diatom growth sufficient for the preparative processes described herein is intended to be within the scope of the present invention.

Nutrient Medium may be prepared, for example, as follows: To each liter of filtered and sterilized seawater may be added 1 ml of the $NaNO_3$ working stock, 1 ml of the $NaH_2PO_4.H_2O$ working stock, 1 ml of the Trace Metal working stock, and 1 ml of the $Na_2SiO_3.9H_2O$ working stock. Simultaneously with the addition of $Na_2SiO_3.9H_2O$, 2 mls of 1N HCl may be added and the solution may be shaken to mix. Next, 1.5 mls 1N NaOH may be added and the solution may again be shaken to mix. Finally, 0.5 ml of the Vitamin working stock may be added.

In order to grow a new diatom culture, 7 ml of a mature culture, (having a cell density within a range of about $1 \times 10^5$ to about $1 \times 10^6$ cells/ml.), may be transferred to a sterile container containing 100 ml of sterile Nutrient Medium, which may be prepared according to the methods described above. The inoculated culture may then be incubated for 8 days under the following conditions:

Temperature: 20° Centigrade Constant illumination.

Agitation: Gentle swirling of flasks once per day.

After 8 days of incubation, 80 ml of this incubated culture may be transferred, under sterile conditions, to 1000 ml of Nutrient Medium, which may, for example, be contained in a 2.8 L Fernbach flask, protected by a cotton wool plug covered by cheesecloth. Such a culture may be allowed to incubate and grow to the desired cell density, or alternatively, may be used to inoculate new diatom cultures. Once a culture reaches a desired cell density, the culture's p-GlcNac fibers may be harvested, and the p-GlcNac starting material may be purified, using methods such as those described below in Section 5.3, below.

$CO_2$ may be dissolved in the culture solution in order to maintain a culture pH of approximately 7 to 8, with approximately 7.4 being preferred. The maintenance of such a neutral pH environment greatly increases the p-GlcNac yield that may be obtained from each diatom culture.

5.3. Methods for Isolation, Purification, and Concentration of p-GlcNac Fibers

Presented in this Section are methods which may be utilized for the preparation of p-GlcNac fibers from diatom cultures such as those described, above, in Section 5.2.

While each of the methods described below for the purification of p-GlcNac from microalgae, preferably diatom, starting sources produces very pure, unadulterated, semi-crystalline p-GlcNac. For example, the p-GlcNac starting material can be purified via the Mechanical Force method presented in Section 5.3.1, below. The second method, which is referred to as the Chemical/Biological method and is described below in Section 5.3.2, produces a much higher average yield than the average p-GlcNac yield produced by the Mechanical Force method. Additionally, the acid treatment/neutralization variation described as part of the Chemical/Biological method of Section 5.3.2, below, produces extremely long p-GlcNac fibers, with some fibers being in excess of 100 µm, and containing molecules of the p-GlcNac polymer of very high molecular weight, as high as 20–30 million daltons. Molecular weight determination of the p-GlcNac polymeric starting material is determined using chromatographic and physiochemical methods well known to those of ordinary skill in the art including, but not limited to measurement of intrinsic viscosity.

5.3.1. Mechanical Force Method for Preparation of Pure p-GlcNac

The p-GlcNac fibers may be separated from diatom cell bodies by subjecting the contents of the culture to an appropriate mechanical force. Such a mechanical force may include, but is not limited to, a shear force generated by, for example, a colloid mill, an ultrasound device, or a bubble generator, or a cutting force generated by, for example, a Waring blender.

The resulting suspension of diatom cell bodies and p-GlcNac fibers are then segregated. For example, the suspension may be subjected to a series of centrifugation steps which segregate the p-GlcNac fibers from the cell bodies, yielding a clear supernatant exhibiting little, if any, visible flocculent material. A fixed angle rotor, and a temperature of about 10° C. are preferred for the centrifugation steps. The speed, duration, and total number of centrifugation steps required may vary depending on, for example, the specific centrifugation rotor being used, but the determination of the values for such parameters will be apparent to one of ordinary skill in the art.

The p-GlcNac fibers in the supernatant may then be concentrated using techniques well known to those of skill in the art. Such techniques may include, but are not limited to suction and filtration devices.

Finally, the concentrated p-GlcNac fibers are washed with, for example, distilled-deionized water, HCl and ethanol, or other appropriate solvents, preferably solvents, such as alcohols, in which both organic and inorganic materials dissolve.

The Working Example presented in Section 7, below, demonstrates the use of this method for the purification of p-GlcNac.

5.3.2. Chemical/Biological Method for Purification of p-GlcNac

In this method, p-GlcNac fibers are separated from diatom cell bodies by subjecting them to chemical and/or biological agents as described in more detail below.

Diatom cultures may be treated with a chemical capable of weakening diatom cell walls, which leads to a release of the p-GlcNac fibers without altering their length and structure. Such a chemical may include, but is not limited to, hydrofluoric acid (HF). Alternatively, a mature diatom culture may be treated with a biological agent capable of altering a biological process may be used to inhibit p-GlcNac fiber synthesis, thus releasing the fibers already present. For example, such an agent may include, but is not limited to, polyoxin-D, an inhibitor of the enzyme N-acetylglucosaminyl-P-transferase.

The cell bodies and p-GlcNac-containing fibers of diatom cultures treated with a member of the above described chemical or biological agents are then segregated. For example, the contents of treated diatom cultures may be allowed to settle such that the contents of the cultures are allowed to form two distinct layers. The upper layer will contain primarily the p-GlcNac fibers, while the bottom layer will contain the cell bodies. The upper p-GlcNac fiber-containing layer may be siphoned off, leaving behind the settled cellular material of the bottom layer.

The siphoned off p-GlcNac fiber-containing layer may then be further purified to remove protein and other unwanted matter by treatment with a detergent that will not damage the p-GlcNac fibers. Such a detergent may include, but is not limited to, sodium dodecyl sulfate (SDS).

When acid treatment, such as HF treatment, is used to separate p-GlcNac fibers from diatom cell bodies, a step may be included for the dispersal of the fibers. Such a step may include, but is not limited to, the use of mechanical force for fiber dispersal, such as a step in which the fibers are subjected to the movements of an orbital shaker.

Alternatively, the acid-treated suspension may, in an optional step, be neutralized prior to further purification by detergent treatment. Such neutralization will, in general, change the pH of the suspension from approximately 1.8 to approximately 7.0, and may be accomplished by, for example, the addition of an appropriate volume of 1M Tris (pH 8.0) or the addition of an appropriate volume of sodium hydroxide (NaOH). Neutralization, in general, yields pure p-GlcNac fibers of a substantially greater length than the other purification methods discussed herein.

The purified p-GlcNac fibers may then be concentrated using techniques well known to those of skill in the art, such as by utilizing a suction and filtration device. Finally, the p-GlcNac fibers are washed, in a series of steps with distilled-deionized water, HCl and ethanol, or other appropriate solvents, preferably solvents, such as alcohols, in which both organic and inorganic materials dissolve.

The Working Example presented, below, in Section 8 demonstrates the successful utilization of such a purification method.

The p-GlcNac starting material, or its partially deacetylated derivative, may be subjected to controlled hydrolysis conditions, which yield groups of molecules having uniform, discrete molecular weight and other physical characteristics. Such hydrolysis conditions may include, for example, treatment with the enzyme, lysozyme. p-GlcNac may be exposed to lysozyme for varying periods of time, in order to control the extent of hydrolysis. Such enzymatic, partial-digestion reactions may also be controlled by varying the concentration of the substrate, or of the enzyme, or both the substrate and enzyme, as well as the pH and temperature. In addition, the rate of hydrolysis may be controlled as a function of the extent to which the p-GlcNac that is being lysozyme-treated has been deacetylated. Deacetylation conditions may be as described earlier in this Section. The more fully a p-GlcNac molecule has been deacetylated, between about 20 and about 90 percent deacetylated, the more fully the molecule will be hydrolyzed in a given time. Changes in physical characteristics, in addition to the lowering of molecular weight, may be elicited by hydrolysis and/or deacetylation treatments. The results of a hydrolysis/deacetylation procedure are presented below in the Working Example of Section 9, below.

5.4. Derivatization of p-GlcNac

The pure, fully acetylated p-GlcNac starting material may be derivatized, by utilizing a variety of controlled conditions and procedures, into a large range of different compounds. See FIG. 13 for a diagram depicting some of these compounds. Such derivatized compounds may include, but are not limited to, partially deacetylated p-GlcNac, which has been modified via chemical and/or enzymatic means, as described in further detail, below. Additionally, p-GlcNac, or its partially deacetylated derivative, may be derivatized by being sulfated, phosphorylated, and/or nitrated. Further, as detailed below, O-sulfonyl, N-acyl, O-alkyl, N-alkyl, and N-alkylidene and N-arylidene and other derivatives may be prepared from the p-GlcNac or partially deacetylated p-GlcNac starting material. The partially deacetylated p-GlcNac starting material may also be used to prepare a variety of organic salts and/or metal chelates. Further, the p-GlcNac starting material, or a derivative thereof, may have attached to it, either covalently or non-covalently, any of a variety of molecules. Still further, the p-GlcNac starting material, or a derivative thereof, may be subjected to controlled hydrolysis conditions which yield groups of molecules having uniform and discrete molecular weight characteristics. Such materials are useful in the present invention provided the p-GlcNac polymer retains its semi-crystalline structure as demonstrated by sharp, discrete peaks when the polymer is analyzed by IR absorption spectroscopy.

One or more of the monosaccharide units of the p-GlcNac starting material may be deacetylated to form a partially-deacetylated poly-β-1→4-N-acetylglucosamine species. The deacetylated monomers can be, generally, essentially randomly distributed throughout the polymer, or may be relative clustered in discrete subregions within the poly-β-1→4-N-acetylglucosamine polymer. A poly-β-1→4-N-glucosamine species starting material in which a portion of the monosaccharide units of the poly-β-1→4-N-acetylglucosamine species starting material has been deacetylated will have a molecular weight of up to about 30 million daltons, comprising about 150,000 glucosamine monosaccharides covalently attached in a β-1→4-N configuration. In one embodiment, at least about 90% of the glucosamine monosaccharide units of the poly-β-1→4-N-glucosamine species remain acetylated, while in other embodiments, at least about 80%, 70%, 60%, 50%, or 40% of the monosaccharide units of the poly-β-1→4-N-glucosamine species remain acetylated, provided the partially-deacetylated poly-β-1→4 N-acetylglucosamine polymer retains its semi-crystalline structure as demonstrated by sharp, discrete peaks when the polymer is analyzed by IR absorption spectroscopy, as described in Example 6, below, and as depicted in FIGS. 4A, 4D, and 4E, in contrast to IR absorption spectra displayed by non-crystalline p-GlcNac polymers, as depicted in FIGS. 4B and 4C.

The p-GlcNac starting material may be deacetylated by treatment with a base to yield glucosamines with free amino groups. This hydrolysis process may be carried out with solutions of concentrated sodium hydroxide or potassium hydroxide at elevated temperatures. However, to control the extent of deacetylation precisely and to avoid degradation of the main carbohydrate chain of the polysaccharide molecule, it is preferable that an enzymatic procedure utilizing a chitin deacetylase enzyme be used for p-GlcNac deacylation. Such a deacetylase enzymatic procedure is well known to those of skill in the art and may be performed as in (U.S. Pat. No. 5,219,749), which is incorporated herein, by reference, in its entirety.

One or more of the monosaccharide units of the p-GlcNac starting material may be derivatized to contain at least one sulfate group, or, alternatively, may be phosphorylated or nitrated, as depicted below:

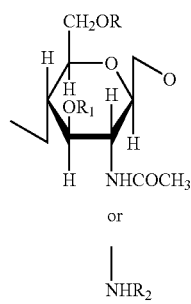

where, R and/or $R_1$, in place of a hydrogen, and/or $R_2$, in place of —$COCH_3$, may be a sulfate (—$SHO_3$), a phosphate (—$P(OH)_2$), or a nitrate (—$NO_2$) group.

Described below are methods by which such p-GlcNac derivatives may be prepared. Before performing methods such as those described in this Section, it may be advantageous to first lyophilize, freeze in liquid nitrogen, and pulverize the p-GlcNac starting material.

Sulphated p-GlcNac derivatives may be generated, by, for example, a two step process. In the first step, O-carboxymethyl p-GlcNac may be prepared from the p-GlcNac and/or p-GlcNac derivatives of the starting material by, for example, utilizing techniques such as those described by Tokura et al. (Tokura, S. et al., 1983, Polym. J. 15:485). Second, the sulfation step may be carried out with, for example, N,N-dimethyl-formamide-sulfur trioxide, according to techniques well known to those of skill in the art, such as are described by Schweiger (Schweiger, R. G., 1972, Carbohydrate Res. 21:219). The resulting product may be isolated as a sodium salt. Phosphorylated p-GlcNac derivatives of the starting material may be prepared, for example, by utilizing techniques well known to those of skill in the art, such as those described by Nishi et al. (Nishi, N. et al., 1986, in "Chitin in Nature and Technology," Muzzarelli et al., eds. Plenum Press, New York, pp. 297–299). Briefly, p-GlcNac/methanesulfonic acid mixture may be treated with phosphorus pentoxide (in an approximately 0.5 to 4.0 molar equivalent) with stirring, at a temperature of about 0° C. to about 5° C. Treatment may be for about 2 hours. The resulting product may then be precipitated and washed using standard techniques well known to those of skill in the art. For example, the sample may be precipitated with a solvent such as ether, centrifuged, washed with a solvent such as ether, acetone, or methanol, and dried.

Nitrated p-GlcNac derivatives may be prepared by utilizing techniques well known to those of skill in the art, such as those described by Schorigin and Halt (Schorigin, R. and Halt, E., 1934, Chem. Ber. 67:1712). Briefly, p-GlcNac and/or a p-GlcNac derivative may be treated with concentrated nitric acid to form a stable nitrated product.

One or more of the monosaccharide units of the p-GlcNac starting material may contain a sulfonyl group, as depicted below:

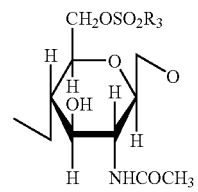

where $R_3$ may be an alkyl, an aryl, an alkenyl, or an alkynyl moiety. Such a derivative may be generated by well known methods such as the method described in Kurita et al. (Kurita, K. et al, 1990, Polym. Prep (Am. Chem. Soc., Div. Polym. Chem.) 31:624–625). Briefly, an aqueous alkali p-GlcNac solution may be reacted with a chloroform solution of tosyl chloride, and the reaction may then be allowed to proceed smoothly at low temperatures.

One or more of the monosaccharides of the p-GlcNac starting material or its deacetylated derivative may contain one or more O-acyl groups as depicted below:

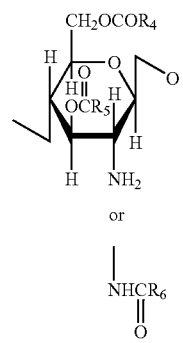

where $R_4$ and/or $R_5$, in place of hydrogen, may be an alkyl, an alkenyl, or an alkynyl moiety, and $R_6$ may be an alkyl, an alkenyl, or an alkynyl moiety. An example of such a derivative may be generated by well known methods such as those described by Komai (Komai, T. et al., 1986, in "Chitin in Nature and Technology," Muzzarelli et al., eds., Plenum Press, New York, pp. 497–506). Briefly, p-GlcNac may be reacted with any of a number of suitable acyl chlorides in methanesulfonic acid to yield p-GlcNac derivatives which include, but are not limited to, caproyl, capryl, lanoyl, or benzoyl derivatives.

One or more of the monosaccharides of the deacetylated p-GlcNac starting material may contain an N-acyl group, as depicted below:

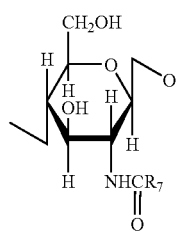

where $R_7$ may be an alkyl, an alkenyl, or an alkynyl moiety. Such a derivatization may be obtained by utilizing techniques well known to those of skill in the art, such as the technique described in Hirano et al. (Hirano, S. et al., 1976, Carbohydrate Research 47: 315–320).

Deacetylated p-GlcNac is soluble in a number of aqueous solutions of organic acids. The addition of selected carboxylic anhydrides to such p-GlcNac-containing solutions, in aqueous methanolic acetic acid, results in the formation of N-acyl p-GlcNac derivatives.

One or more of the monosaccharides of the deacetylated p-GlcNac starting material or of its deacetylated derivative, may contain an O-alkyl group, as depicted below:

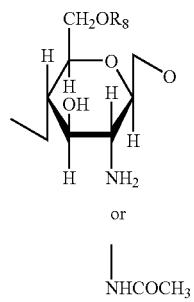

where $R_8$ may be an alkyl, and alkenyl, or a alkynyl moiety. Such a derivatization may be obtained by using techniques well known to those of skill in the art. For example, the procedure described by Maresh et al. (Maresh, G. et al., in "Chitin and Chitosan," Skjak-Braek, G. et al., eds., 1989, Elsevier Publishing Co., pp. 389–395). Briefly, deacetylated p-GlcNac may be dispersed in dimethoxyethane (DME) and reacted with an excess of propylene oxide. The period of the reaction may be 24 hours, and the reaction takes place in an autoclave at 40° to 90° C. The mixture may then be diluted with water and filtered. The DME may be removed by distillation. Finally, the end-product may be isolated via lyophilization.

One or more of the monosaccharide units of the p-GlcNac starting material may be an alkali derivative, as depicted below:

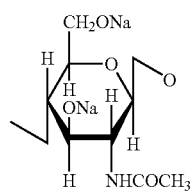

Such a derivative may be obtained by using techniques well known to those of skill in the art. For example, a method such as that described by Noguchi et al. (Noguchi, J. et al., 1969, Kogyo Kagaku Zasshi 72:796–799) may be utilized. Briefly, p-GlcNac may be steeped, under vacuo, in NaOH (43%, preferably) for a period of approximately two hours at about 0° C. Excess NaOH may then be removed by, for example, centrifugation in a basket centrifuge and by mechanical pressing.

One or more of the monosaccharide units of the deacetylated derivative of the p-GlcNac starting material may contain an N-alkyl group, as depicted below:

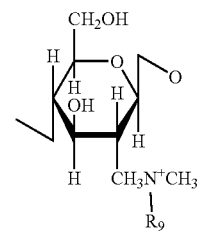

where $R_9$ may be an alkyl, an alkenyl, or an alkynyl moiety. Such a derivatization may be obtained by utilizing, for example, a procedure such as that of Maresh et al. (Maresh, G. et al., in "Chitin and Chitosan," Skjak-Brack, G. et al., eds. 1989, Elsevier Publishing Co., pp. 389–395), as described, above, for the production of O-alkyl p-GlcNac derivatives.

One or more of the monosaccharide units of the deacetylated derivative of the p-GlcNac starting material may form a salt, as depicted below:

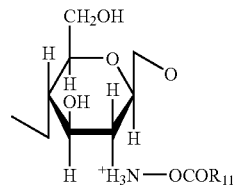

where $R_{11}$ may be an alkyl, an alkenyl, or an alkynyl moiety. Such a derivatization may be obtained by using techniques well known to those of skill in the art. For example, a procedure such as that described by Austin and Sennett (Austin, P. R. and Sennett, S., in "Chitin in Nature and Technology," 1986, Muzzarelli, R. A. A. et al., eds. Plenum Press, pp. 279–286) may be utilized. Briefly, deacetylated p-GlcNac may be suspended in an organic medium such as, for example, ethyl acetate or isopropanol, to which may be added an appropriate organic acid such as, for example, formic, acetic, glycolic, or lactic acid. The mixture may be allowed to stand for a period of time (1 to 3 hours, for example). The temperature of reaction and drying may vary from about 12° C. to about 35° C., with 20° to 25° C. being preferred. The salts may then be separated by filtration, washed with fresh medium, and the residual medium evaporated.

One or more of the monosaccharide units of the deacetylated derivative of the p-GlcNac starting material may form a metal chelate, as depicted below:

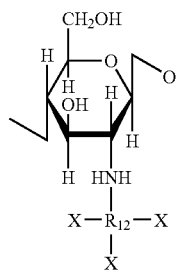

where $R_{12}$ may be a metal ion, particularly one of the transition metals, and X is the dative bond established by the nitrogen electrons present in the amino and substituted amino groups present in the deacetylated p-GlcNac.

One or more of the monosaccharide units of the deacetylated derivative of the p-GlcNac starting material may contain an N-alkylidene or an N-arylidene group, as depicted below:

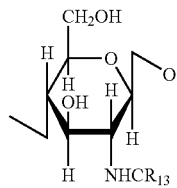

where $R_{13}$ may be an alkyl, an alkenyl, an alkynyl, or an aryl moiety. Such a derivatization may be obtained by using techniques well known to those of skill in the art. For example, a procedure such as that described by Hirano et al (Hirano, S. et al., 1981, J. Biomed. Mat. Res. 15:903–911) may be utilized. Briefly, an N-substitution reaction of deacetylated p-GlcNac may be performed with carboxylic anhydrides and/or arylaldehydes to yield acyl- and/or arylidene derivatives.

Further, the p-GlcNac starting material, or its partially-deacetylated derivative, may be subjected to controlled hydrolysis conditions, which yield groups of molecules having uniform, discrete molecular weight and other physical characteristics. Such hydrolysis conditions may include, for example, treatment with the enzyme, lysozyme. p-GlcNac may be exposed to lysozyme for varying periods of time, in order to control the extent of hydrolysis. In addition, the rate of hydrolysis may be controlled as a function of the extent to which the p-GlcNac that is being lysozyme treated has been deacetylated (see, for example the Examples provided in Section 15, and depicted in FIGS. 18–20). Such enzymatic, partial digestion reactions may also be controlled by varying the concentration of the substrate, the enzyme, or both the substrate and enzyme, as well as the pH and temperature. In another embodiment, p-GlcNac polymers are reduced in size by sonication which may be varied not only by the power of the instrument used but also by the pH, salt concentration, and temperature of the sample. Solubilization of p-GlcNac or derivatives thereof are described below in Section 5.5. Accordingly, by using one or more of these methods, either alone or in combination with one another, higher molecular weight p-GlcNac polymers can be hydrolyzed to smaller fragments, which can be chromatographically separated according to size using, for example, column chromatography.

For example, one skilled in the art will vary the extent of partial digestion of p-GlcNac to provide reaction product having a desired range of molecular weight. In other embodiments, the substrate used for partial digestion with lysozyme, is p-GlcNac that has been sonicated and/or partially de-acetylated. By combining partial enzymatic digestion with separation techniques, such as column chromatography, HPLC separations or other techniques and methods well-known in the art, a skilled artisan can isolate digestion products with a narrow range of molecular weight distribution. Moreover, by combining the products of a series of partial-digestion reactions, one skilled in the art can assemble a composition comprising p-GlcNac polymers having a wider range of molecular weight species of semi-crystalline p-GlcNac products, including, e.g., the populations disclosed herein, that is polymers comprising from about 50 to about 150,000 monomeric units in one embodiment, as well as about 50 to about 50,000, about 50 to about 10,000, and about 50 to about 4,000 monomeric units.

Deacetylation conditions may be as described earlier in this Section. The more fully a p-GlcNac molecule has been deacetylated, between about 20 and about 90 percent deacetylated, the more fully the molecule will be hydrolyzed in a given time. Changes in physical characteristics, in addition to the lowering of molecular weight, may be elicited by hydrolysis and/or deacetylation treatments.

Further, a variety of molecules may be covalently or non-covalently functionally attached to the deacetylated derivatives of the p-GlcNac starting material. Such molecules may include, but are not limited to such polypeptides as growth factors, such as nerve growth factor, proteases, such as pepsin, hormones, or peptide recognition sequences such as RGD sequences, fibronectin recognition sequences, laminin, integrins, cell adhesion molecules, and the like. See, e.g., the compounds discussed, below, in Section 5.6.1.1. Covalent attachment of molecules to the exposed primary amines of deacetylated p-GlcNac may be accomplished by, for example, chemical attachment utilizing bi-functional cross-linking reagents that act as specific length chemical spacers. Such techniques are well known to those of skill in the art, and may resemble, for example, the methods of Davis and Preston (Davis, M. and Preston, J. F. 1981, Anal. Biochem. 116:404–407) and Staros et al. (Staros, J. V. et al, 1986, Anal. Biochem. 156:220–222). Briefly, carboxylic residues on the peptide to be attached to the deacetylated or partially deacetylated p-GlcNac starting material may be activated and then crosslinked to the p-GlcNac. Activation may be accomplished, for example, by the addition of a solution such as carbodiimide EDC (1-ethyl-3-(3-dimethylaminopropyl)carbodiimide) to a peptide solution in a phosphate buffer. Preferably, this solution would additionally contain a reagent such as sulpho-NHS (N-hydroxysulphosuccinimide) to enhance coupling. The activated peptide may be crosslinked to the deacetylated p-GlcNac by mixing in a high pH buffer, such as carbonate buffer (pH 9.0–9.2).

The biological activity of the attached peptide (or any covalently attached molecule) can be maintained by varying the length of the linker molecule (e.g., the bi-functional crosslinking compound) utilized to attach the molecule to the p-GlcNac starting material. An appropriate linker length for a given molecule to be attached which will not alter the biological activity of the attached molecule can routinely be ascertained. For example, the biological, activity (e.g., a therapeutically effective level of biological activity) of a molecule which has been attached via a linker of a given length can be tested by utilizing well-known assays specific for the given molecule being attached.

Additionally, in order to maintain the biological activity of the molecule being attached, it may be necessary to utilize a linker which can be cleaved by an appropriate naturally occurring enzyme to release the peptide (or any covalently attached molecule).

As above, assays commonly employed by those of skill in the art may be used to test for the retention of the biological activity of the particular molecule being attached to ensure that an acceptable level of activity (e.g., a therapeutically effective level activity) is retained.

Alternatively, molecules such as those described above may be non-covalently attached to p-GlcNac and its derivatives using techniques well known to those of skill in the art. For example, a molecule or molecules of choice may be mixed with suspensions of p-GlcNac, or partially deacetylated p-GlcNac solution, with a p-GlcNac-lactate solution, with a deacetylated or partially deacetylated p-GlcNac salt solution, or with any p-GlcNac derivative solution. The mixtures can then be lyophilized. Molecules become bound to the p-GlcNac matrices following lyophilization, presumably via hydrophobic, electrostatic and other non-covalent interactions. Such p-GlcNac formulations are, therefore, very easy to produce. Further, such formulations can effectively be achieved with a wide variety of molecules having a broad spectrum of physical characteristics and water solubility properties, ranging from the most hydrophobic to the most hydrophilic. Upon attachment of the molecule or molecules, assays commonly employed by those of skill in the art to test the activity of the particular non-covalently attached molecule or molecules can be used to ensure that an acceptable level of activity (e.g., a therapeutically effective activity) is achieved with the attached molecule.

Alternatively, hybrids comprising p-GlcNac and/or p-GlcNac derivatives may be formed. Such hybrids may contain any of a number of natural and/or synthetic materials, in addition to p-GlcNac and/or p-GlcNac derivatives. For example, hybrids may be formed of p-GlcNac and/or p-GlcNac derivatives plus one or more extracellular matrix (ECM) components. Such ECM components may include, but are not limited to, collagen, fibronectin, glycosaminoglycans, and/or peptidoglycans. Hybrids may also be formed of p-GlcNac and/or p-GlcNac derivatives plus one or more synthetic materials such as, for example, polyethylene. Such a p-GlcNac/polyethylene or p-GlcNac derivative/polyethylene hybrid may be made by thermally linking the hybrid components via, for example, autoclaving. Such hybrid polymers are useful in the present methods, provided the hybrid polymer retains the p-GlcNac semi-crystalline structure as demonstrated by sharp, discrete peaks when the polymer is analyzed by IR absorption spectroscopy, as described in Example 6, below.

In the case of a collagen/p-GlcNac hybrid, briefly, a p-GlcNac suspension and a collagen suspension may be mixed and lyophilized, and crosslinked, preferably dehydrothermally crosslinked. The collagen species of such hybrids may be native or synthetic, and may be of human or non-human, such as bovine, for example, origin. p-GlcNac/collagen and/or p-GlcNac derivative/collagen hybrid materials exhibit uniform properties, and form a porous matrix. The Working Example presented in Section 13 below, demonstrates the formation, properties and usefulness of such a p-GlcNac/collagen hybrid.

Additionally, an iodo-p-GlcNac derivative may be copolymerized with, for example, styrene, for the manufacture of novel plastic materials. Iodo-p-GlcNac can be prepared by a process similar to that described by Kurita and Inoue (Kurita, K. and Inoue, S., 1989, in "Chitin and Chitosan," Skjak-Braek et al., eds., Elsevier Science Publishing Co., Inc., p. 365), via tosylation and iodination of p-GlcNac. The iodo derivative of p-GlcNac can then be dispersed in nitrobenzene and reacted with styrene, with tin (IV) chloride being used as a catalyst.

Hybrids comprising combinations of deacetylated p-GlcNac and such compounds as, for example sodium alginate, and carboxymethyl p-GlcNac may be formulated using techniques such as those described herein. Such combinations may be formed or reformed into, for example, membranes and fibers.

Complexes of partially deacetylated p-GlcNac with polyanions such as, for example, polyacrylic acid or pectin, possessing both positive and negative charges, may be formulated. The formation of such complexes may be accomplished according to a method similar to that described by Mireles et al. (Mireles, C. et al., 1992, in "Advances in Chitin and Chitosan," Brine, C. J. et al., eds., Elsevier Publishers, Ltd.). Partially deacetylated p-GlcNac and polyacrylic acid, carrageenan or pectin, for example, are dissolved in HCl and NaCl, respectively, and the reactant solutions, with equal pH, are mixed. This operation produces effective molecules possessing both positive and negative characteristics, useful, for example, in the immobilization of enzymes and therapeutic compounds.

5.5. Reformulations

The p-GlcNac starting material, as well as its partially deacetylated derivatives and/or their derivatives, such as those described above in Section 5.4, may be dissolved and subsequently reformulated into a variety of shapes and configurations.

Solution of the p-GlcNac starting material can be achieved by treatment with dimethyl acetamide (DMA)/lithium chloride. p-GlcNac may be readily dissolved by stirring in a DMA solution containing 5% LiCl (by weight of the DMA). Water soluble p-GlcNac derivatives, such as p-GlcNac salts, may be dissolved in water. p-GlcNac which has been partially deacetylated may be put into solution in, for example, a mild acidic solution, such as 1% acetic acid. p-GlcNac derivatives that are water-insoluble may be put into solution in organic solvents.

Derivatization of p-GlcNac in DMA:LiCl with phenyl isocyanates may be used to produce carbanilates. Further, derivatization of p-GlcNac in DMA:LiCl with toluene-p-sulphonylchloride may be used to produce toluene-p-sulfonate.

The p-GlcNac starting material, its partially deacetylated derivatives, and/or their derivatives in solution may then be precipitated and reformulated into shapes which include, but are not limited to, mats, strings, microspheres, microbeads, membranes, fibers, microfibers, powders, and sponges. Further, ultrathin (i.e., less than about 1 micron thick) uniform membranes may be formulated.

Such reformulations may be achieved, by, for example, taking advantage of the fact that pure p-GlcNac is insoluble in solutions such as water and alcohol, preferably ethanol. Introduction, by conventional means, such as by injection, for example, of the p-GlcNac-containing DMA/LiCl mixture into such a water or alcohol, preferably ethanol, solution will bring about the reprecipitation, and therefore reformulation, of the dissolved p-GlcNac. Such a pure p-GlcNac reformulation is demonstrated in the Working Example presented, below, in Section 11. In the case of water soluble p-GlcNac derivatives, reformulations may be achieved by reprecipitating in such organic solvents as, for example, ethyl acetate or isopropanol. Reformulations of p-GlcNac which has been partially deacetylated may be achieved by reprecipitating in an alkaline solution. Water-insoluble p-GlcNac derivatives may be reformulated by reprecipitation in aqueous solutions, such as, for example, water.

p-GlcNac membranes and three-dimensional p-GlcNac matrices may be produced via methods which provide for the formation of controlled average pore sizes within either the membranes or the matrices. Pore size can be controlled in membranes and matrices by varying the amount of p-GlcNac material used, and by the addition of certain solvents such as methanol or ethanol, with ethanol being preferred, in specific amounts, ranging from about 5% to about 40%, prior to the formation of membranes and/or matrices. In general, the greater the percentage of solvent, the smaller the average pore size formed will be. The Example presented, below, in Section 15, demonstrates the synthesis and characterization of such porous p-GlcNac structures.

In other embodiments, the semi-crystalline p-GlcNac is formulated as a gel, foam, spray, or as a solution or suspension comprising microspheres, microbeads, or microfibrils. Such formulations, therefore may further comprise a suitable amount of a pharmaceutically acceptable vehicle or carrier so as to provide the form for proper administration of the semi-crystalline p-GlcNac to the patient.

In a specific embodiment, the term "pharmaceutically acceptable" means approved by a regulatory agency of the Federal or a state govermnent or listed in the U.S. Pharmacopeia or other generally recognized pharmacopeia for use in mammals, and more particularly in humans. The term "carrier" refers to a diluent, adjuvant, excipient, or vehicle with which a therapeutic agent is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, auxiliary, stabilizing, thickening, lubricating and coloring agents may be used. When administered to a patient, the p-GlcNac and the pharmaceutically acceptable carriers are preferably sterile. Saline solutions and aqueous dextrose and glycerol solutions can be employed as liquid carriers. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. p-GlcNac compositions, if desired, can also contain minor amounts of wetting or emulsifying agents, or pH buffering agents.

Compositions containing p-GlcNac can take the form of solutions, suspensions, suppositories, emulsions, aerosols, sprays, or any other form suitable for use. Other examples of suitable pharmaceutical carriers are described in "Remington's Pharmaceutical Sciences" by E. W. Martin.

Although the p-GlcNac formulations and compositions will be supplied as a pre-mixed dosage form, in other embodiments, the semi-crystalline p-GlcNac disclosed herein can be supplied separately, for example as a dry lyophilized powder or water free concentrate in a hermetically sealed container such as an ampoule or sachette indicating the quantity of active agent, which can be suspended or dissolved at a desired concentration in a pharmaceutically acceptable vehicle or solvent prior to use.

The amount of the semi-crystalline p-GlcNac effective in the treatment of a particular disorder or condition will depend on the nature of the disorder or condition, and can be determined by standard clinical techniques. In addition, in vitro or in vivo assays can optionally be employed to help identify optimal dosage ranges. The precise dose of semi-crystalline p-GlcNac to be employed in the compositions will also depend on the route of administration, and the seriousness of the disease or disorder, and should be decided according to the judgment of the practitioner and each patient's circumstances. However, semi-crystalline p-GlcNac is generally topically applied within a range of about 1 mg/cm$^2$ to about 500 mg/cm$^2$. In other embodiments, semi-crystalline p-GlcNac is generally topically applied within a range of about 2 mg/cm$^2$ to about 100 mg/cm$^2$, 5 mg/cm$^2$ to about 50 mg/cm$^2$, and 10 mg/cm$^2$ to about 20 mg/cm$^2$. Effective doses may be extrapolated from dose-response curves derived from in vitro or animal model test systems. In addition to those presented infra in the Examples provided in Sections 16 and 17, other animal model test systems that are well known in the art, include, without limitation the following: (a) a porcine model of partial hepatectomy for evaluating hemostasis treatment as described by Davidson et al. (Davidson et al. 2000, *Br. J. Surg.* 87(6): 790–95); (b) a canine, bleeding ulcer mode, for evaluating treatments intended to achieve hemostasis is described by Pasricha et al. (Pasricha et al. 1999 *Gastointest Endosc* 49(5): 627–31); (c) a surgical bleeding model in the rat, based upon treatment of liver incisions, has been described by Sirieix et al (Sirieix et al 1998 *Ann Vasc Surg* 12(4): 311–16); (d) a method for evaluating vasosconstriction in isolated rat thoracic aortic rings with intact endothelium has been described by Kim et al (Kim et al 2000 *J Lab Clin Med* 135(2): 180–87; also see Guo et al 1994 *Methods Find Exp Clin Pharmaocl* 15(5): 347–54); (e) an experimental model intended to measure both vessel diameter and blood flow through that vessel in the rabbit has been described by Caron et al (Caron et al 1998 *Artif Cells Blood Substit Immobil Biotechnol* 26(3): 293–308); (f) a method permitting the direct observation of uterine microvessels in the rat, permitting evaluation of the circumferential diameters of arterioles as a function of the amount of vasoactive agent applied has been described by Alsip et al (Alsip et al 1996 *Am J Obstet Bynecol* 175(2):388–95); and (g) a model system using spontaneously hypertensive rats has been described by Schiffrin et al, which inter alia, evaluates the level of immunoreactive endothelin in blood vessels using radioimnmunoassay procedures (Schiffrin et al 1995 *Br J Pharmacol* 115(8): 1377–81).

The particular formulation of semi-crystalline p-GlcNac used will vary depending upon the intended application. For example, semi-crystalline p-GlcNac may be formulated and manufactured as a membrane, or bandage etc. for direct application to an accessible surface. In such formulations, the semi-crystalline p-GlcNac can be combined with one or other materials, including but not limited to natural or man-made fibers, and/or reformulated as a copolymer as described herein. The amount of semi-crystalline p-GlcNac/cm$^2$ formulated into such a material is determined by the intended use, e.g., the lower ranges for treating, inter alia, minor cuts and scrapes, and higher p-GlcNac levels for treatment of mor serious injuries. The size, shape, thickness, and overall composition, including the total amount of semi-crystalline p-GlcNac formulated therein, of such materials is similarly determined by the intended use.

Where the semi-crystalline p-GlcNac is to be topically administered to a surface not readily accessible, e.g., oral or nasal cavities, or deep wounds to the body, the semi-crystalline p-GlcNac is formulated, inter alia, as a gel, foam, spray, emulsion, suspension or solution, employing the pharmaceutically acceptable carriers and vehicles disclosed above. Such formulations, which usually will be non-barrier forming materials, generally comprise microspheres, microbeads, or microfibrils formed from semi-crystalline p-GlcNae, and may further comprise materials, including but not limited to, natural or man-made fibers, and/or semi-crystalline p-GlcNac reformulated as a copolymer as described herein. Again, the amount and/or concentration of semi-crystalline p-GlcNac included in such formulations is dependent upon the intended use, and would be apparent to those of skill in the art and readily determined through routine in vitro and in vivo testing, especially with animal model systems well known in the art.

Since the modulating effects of semi-crystalline p-GlcNac on vascular structure and/or function are both localized and transient, administration of formulations comprising semi-crystalline p-GlcNac may be repeated, at intervals, until the condition to be corrected is resolved. Generally, such intervals are about one hour, but they may be shorter or longer, depending on the nature of the condition treated and the amount of semi-crystalline p-GlcNac applied. In those instances in which a composition comprising a semi-crystalline p-GlcNac formulation has been applied to a relatively non-accessible surface, bio-degradable compositions and formulations are preferred.

5.6. Uses

The p-GlcNac starting material has a variety of uses, including modulation of vascular structure and/or function via, for example, stimulation of endothelin-1 release, vasoconstriction, and reduction in blood flow out of a breached vessel, as well as contributing to or effecting cessation of bleeding. The topically-applied p-GlcNac of the present invention is biocompatible, biodegradable, nontoxic, and non-pyrogenic. Because the p-GlcNac materials of the present invention are also immunoneutral, they do not elicit an immune response in humans, and therefore are particularly advantageously used in the formulation of the devices disclosed herein, which include but are not limited to films, membranes, gels, sponges, microspheres, microbeads, microfibrils, foams, and sprays. Certain additional materials, such as natural alginates and, in some cases, synthetic polymers, can also be used in the construction of such materials and devices, in combination with the p-GlcNac described herein, provided the poly-$\beta$-1$\rightarrow$4 N-acetylglucosamine polymer retains its semi-crystalline structure as demonstrated by sharp, discrete peaks when the polymer is analyzed by IR absorption spectroscopy, as described in Example 6, below. In one embodiment, the p-GlcNac consists essentially of fully acetylated, semi-crystalline polymers of $\beta$-1$\rightarrow$4 N-acetylglucosamine wherein the polymer comprises about 50 to about 150,000 N-acetylglucosamine monosaccharides covalently attached in a $\beta$-1$\rightarrow$4 conformation, free of protein, substantially free of other organic contaminants, substantially free of inorganic contaminants, and having a molecular weight of about 10,000 daltons to about 30 million daltons. In other embodiments, the p-GlcNac consists essentially of fully acetylated, semi-crystalline polymers of $\beta$-1$\rightarrow$4 N-acetylglucosamine wherein the polymer comprises about 50 to about 50,000, about 50 to about 10,000, or about 50 to about 4,000 N-acetylglucosamine monosaccharides covalently attached in a $\beta$-1$\rightarrow$4 conformation, free of protein, substantially free of other organic contaminants, substantially free of inorganic contaminants, and having a molecular weight of about 10,000 daltons to about 10 million daltons, of about 10,000 daltons to about 2 million daltons, and about 10,000 daltons to about 800,000 daltons, respectively.

5.6.1. Stimulation of Endothelin-1 Release p-GlcNac materials of the present invention are used, for example, to stimulate the release of endothelin-1, as demonstrated successfully in the Example presented in section 16, below. Stimulation of endothelin-1 release is used, inter alia, for the treatment of menorrhagia associated with markedly lower levels of endothelin-1 production by uterine endometrial tissue.

Stimulation of endothelin-1 release is achieved by topical application of compositions and materials comprising p-GlcNac to target tissue of a human or a non-human mammal, including but not limited to veterinary and companion animals. Such materials and compositions may comprise certain additional materials, such as natural alginates and, in some cases, synthetic polymers, in combination with the p-GlcNac described herein. The p-GlcNac of such compositions and materials, in preferred embodiments, consists essentially of fully acetylated, semi-crystalline polymers of $\beta$-1$\rightarrow$4 N-acetylglucosamine polymers which are free of protein, substantially free of other organic contaminants, and are substantially free of inorganic contaminants, and have a molecular weight of up to about 30 million daltons.

Materials of the present invention, which comprise p-GlcNac, are formulated and applied as, for example, gels, films, membranes, and sponges. Such materials may also be formulated and applied as a solution or suspension of microspheres, microbeads, microfibrils, or as a foam or spray. Accordingly, the materials of the present invention that comprise p-GlcNac need not be barrier-forming materials.

Compositions and materials of the present invention, comprising p-GlcNac, are applied directly to target tissue, i.e. tissue in which it is desired to stimulate endothelin-1 release, which could be, e.g., uterine endometrial tissue of patients affected by menorrhagia. The target tissue is, generally, endothelial tissue, and more particularly, will include blood vessels, which can be arteries, veins, or capillaries. The materials comprising semi-crystalline p-GlcNac are topically applied, for example, as a gel, film, membrane, sponge, spray or foam, as well as a suspension, emulsion, or solution of microspheres, microbeads, or microfibrils.

Topical application of the compositions and materials of the present invention, which comprise p-GlcNac, stimulate, relative to target tissue untreated with p-GlcNac, release of endothelin-1 in the target tissue, that is localized, transient, and dependent upon the dose of p-GlcNac administered. Stimulation of endothelin-1 release is localized in that it is most pronounced in that tissue in direct contact with the material comprising p-GlcNac, and, furthermore, the degree of stimulation of endothelin-1 release in the adjacent tissue diminishes as the distance from the point of contact between the target tissue and the material comprising p-GlcNac increases (see e.g. the Example presented in section 16, infra.).

Stimulation of endothelin-1 release is transient in that the level of endothelin-1 in tissue contacted with material comprising semi-crystalline p-GlcNac is greatest shortly after administration of such materials and declines thereafter to the levels observed prior to stimulation. That is, the concentration of endothelin-1 in the contacted tissue is greatest generally not later than 15 minutes after administration of semi-crystalline p-GlcNac, and the concentration of endothelin-1 returns substantially to the level observed immediately prior to that contact, within about 60 minutes after administration of semi-crystalline p-GlcNac (see e.g the Example presented in section 16, infra.). Accordingly, in those instances requiring prolonged stimulation of endothelin-1 release, additional aliquots or doses of compositions and/or materials formulated with semi-crystalline p-GlcNac, are applied to the target tissue, in a sequential manner.

Stimulation of endothelin-1 release is dose-dependent in that the level of endothelin-1 released by endothelial tissue contacted with material comprising p-GlcNac is substantially proportional to the amount p-GlcNac in that material (for a representative demonstration of such a "substantially proportionate" effect, see e.g. the Example presented in section 16, infra.). Accordingly, compositions and materials are formulated and constructed to comprise that level of p-GlcNac required for the level of stimulation of endothelin-1 release needed. Determination of such levels is readily ascertained from routine in vitro experimentation, and animal model testing. Accordingly, in those instances in which a greater degree of stimulation of endothelin-1 release is required, compositions and materials are formulated with an increased concentration of p-GlcNac.

5.6.2. Induction of Vasoconstriction p-GlcNac materials of the present invention are used, for example, to induce vasoconstriction, as demonstrated successfully in the Examples presented in Sections 16 and 17, below, as well as depicted in FIG. 22. Vasoconstriction is achieved by topical application of compositions and materials comprising semi-crystalline p-GlcNac to target tissue of a human or a non-human mammal, including but not limited to veterinary and companion animals.

Clinical applications for which the topical application of compositions comprising semi-crystalline p-GlcNac are useful include, inter alia, use in diagnostic procedures which result in biopsy wounds in, for example, liver and kidney, or result in puncture wounds in blood vessels, e.g. cardiac catheterization and balloon angioplasty procedures. The methods of the present invention are therefore particularly useful in patients afflicted with any form of coagulopathy, which may arise from a genetic defect or from administration of an anticoagulant such as coumadin or heparin. While not wishing to be bound to any particular theory or mechanism, it is believed that vasoconstriction elicited by topical application of semi-crystalline p-GlcNac physically reduces the size of the puncture wound and thereby facilitates or effects cessation of bleeding in a manner and by a mechanism that is not dependent upon clot formation.

The materials and compositions used in the present invention may comprise certain additional materials, such as natural alginates and, in some cases, synthetic polymers, in combination with the p-GlcNac described herein. The p-GlcNac of such compositions and materials, in preferred embodiments, consists essentially of fully acetylated, semi-crystalline polymers of β-1→4 N-acetylglucosamine, which are free of protein, substantially free of other organic contaminants, and substantially free of inorganic contaminants, and having a molecular weight of up to about 30 million daltons.

Materials of the present invention, which comprise p-GlcNac, are formulated as, for example, gels, films, membranes, and sponges. Such materials may also be formulated an applied as a solution or suspension of microspheres, microbeads, microfibrils, or as a spray or foam. Accordingly, the materials of the present invention that comprise p-GlcNac need not be barrier-forming materials.

Compositions and materials of the present invention, comprising p-GlcNac, are applied to the skin or other tissue adjacent to or contiguous with the target tissue, or are applied directly to the target tissue, i.e. tissue or vessel in which it is desired to induce vasoconstriction. The target tissue or vessel includes, generally, arteries, veins, or capillaries. The materials of the present invention which comprise p-GlcNac are topically applied, for example, as a gel, film, membrane, or sponge, spray or foam, or as suspension or solution of microspheres, microbeads, or microfibrils.

Topical application of the compositions and materials of the present invention, which comprise p-GlcNac, stimulate vasoconstriction that is localized, and transient, and dependent upon the dose of p-GlcNac administered. Induction of vasoconstriction is localized in that it is most pronounced in those vessels in direct contact with the material comprising p-GlcNac, and, furthermore, the degree of stimulation of vasoconstriction diminishes as the distance from the point of contact of the material comprising p-GlcNac and the target vessel increases.

Stimulation of vasoconstriction is transient in that the degree of vasoconstriction in the vessel is greatest shortly after administration of the p-GlcNac materials of the present invention and declines thereafter to the levels observed prior to stimulation. That is, the degree of vasoconstriction is greatest generally not later than 15 minutes after administration of p-GlcNac, and then declines to substantially control levels, within about 60 minutes after administration of p-GlcNac. Accordingly, in those instances requiring prolonged vasoconstriction, additional aliquots or doses of compositions and/or materials formulated with p-GlcNac, are applied to the target tissue, in a sequential manner.

Induction of vasoconstriction is dose-dependent in that the degree of vasoconstriction in those vessels contacted with material comprising p-GlcNac is substantially proportional to the amount p-GlcNac in that material. Accordingly, compositions and materials are formulated and constructed to comprise that level of p-GlcNac required for the degree of vasoconstriction desired. Determination of such levels of p-GlcNac is readily ascertained from routine in vitro experimentation, and animal model testing. Accordingly, in those instances in which a greater induction of vasoconstriction is required, compositions and materials are formulated with an increased concentration of p-GlcNac.

5.6.3. Reduction in Blood Flow out of a Breached Vessel

The methods of the present invention, which comprise topical administration of material comprising p-GlcNac, are also used, for example, to reduce blood flow out of a breached vessel in a target tissue. Clinical uses for the topical application of p-GlcNac to effect a reduction in blood flow out of a breached vessel, include, but are not limited to, treatment of abdominal aortic aneurysms, embolization treatment of tumors, uterine fibroid lesions and cerebral aneurysms, wounds including, for example, spleen, liver and blood vessel injuries, and in standard and minimally invasive surgical procedures, for example, endometriosis surgery and operations on the gallbladder. In each of these examples, reduction in blood flow out of a breached vessel as a result of topical application of p-GlcNac-containing materials, results in a reduction in blood loss during the procedure. Accordingly, use of the compositions and methods disclosed herein to bring about vasoconstriction would be particularly useful for the treatment of such condition is patients afflicted with any form of coagulopathy, which may arise from a genetic defect or from administration of an anticoagulant such as coumadin or heparin.

Materials and compositions used in the present methods may comprise certain additional materials, such as natural alginates and, in some cases, synthetic polymers, in combination with the p-GlcNac described herein. The p-GlcNac of such compositions and materials, in preferred embodiments, consists essentially of fully acetylated, semi-crystalline polymers of β-1→4 N-acetylglucosamine wherein the polymer is free of protein, substantially free of other organic contaminants, substantially free of inorganic contaminants, and having a molecular weight of up to about 30 million daltons.

Materials of the present invention, which comprise p-GlcNac, are formulated as, for example, as gels, films, membranes, and sponges. Such materials may also be formulated and applied as a solution or suspension of microspheres, microbeads, or microfibrils, and/or applied as foam or spray. Accordingly, the materials of the present invention that comprise p-GlcNac need not be barrier-forming materials.

Compositions and materials of the present invention, comprising p-GlcNac, are applied either to the skin or other tissue adjacent to or contiguous with the target tissue, or are applied directly to the target tissue, i.e. tissue or blood vessel in which it is desired to reduce blood flow out of a breached vessel. The target vessel may be an artery, vein, or capillary. The materials of the present invention, which comprise p-GlcNac, are topically applied, for example, as a gel, film, membrane, sponge, spray or foam, or as a suspension or solution of microspheres, microbeads, and/or microfibrils.

Topical application of the compositions and materials of the present invention, which comprise p-GlcNac, induce a reduction in blood flow out of a breached vessel that is localized, transient, and dependent upon the dose of p-GlcNac administered. Reduction in blood flow out of a breached vessel is localized in that it is most pronounced in vessels in direct contact with the material comprising p-GlcNac, and, furthermore, the degree of reduction in blood flow out of a breached vessel diminishes as the distance from the point of contact between the material comprising p-GlcNac and the target vessel increases.

Reduction in blood flow out of a breached vessel is transient in that the reduction in blood flow contacted with material comprising p-GlcNac is greatest shortly after administration of such materials and blood flow out of a breached vessel thereafter returns to control levels. That is, the degree of reduction of blood flow out of a breached vessel is greatest generally not later than 15 minutes after administration of p-GlcNac, and then blood flow out of a breached vessel returns to control levels within about 60 minutes after administration of p-GlcNac. Accordingly, in those instances requiring prolonged reduction of blood flow out of a breached vessel, additional aliquots or doses of compositions and/or materials formulated with p-GlcNac, are applied to the target tissue or vessel, in a sequential manner.

Reduction of blood flow out of a breached vessel is dose-dependent in that the reduction in blood flow out of vessels contacted with material comprising p-GlcNac is substantially proportional to the amount p-GlcNac in that material. Accordingly, compositions and materials are formulated and constructed to comprise that level of p-GlcNac required for the reduction in blood flow out of a breached vessel desired. Determination of such levels is readily ascertained from routine in vitro experimentation, and animal model testing. Accordingly, in those instances in which a greater degree reduction in blood flow out of a breached vessel is required, compositions and materials are formulated with an increased concentration of p-GlcNac.

5.6.4 Specific Indications for Use of the Disclosed Methods

Specific instances in which stimulation of endothelin-1 release, vasoconstriction, and/or reduction in blood flow out of a breached vessel, as well as cessation of bleeding are desired include, but are not limited to, use in diagnostic procedures which result in biopsy wounds in, for example, liver and kidney; in embolization procedures including, but not limited to the prevention of bleeding following endovascular treatment of abdominal aortic aneurysms, as well as embolization treatment of tumors, uterine fibroid lesions and cerebral aneurysms; for treatment of menorrhagia; in wounds including, for example, spleen, liver and blood vessel injuries; in standard and minimally invasive surgical procedures, for example, endometriosis surgery and operations on the gallbladder; in soft and hard tissue wound repair, for example, skin wounds and burn healing; in surgical procedures, in particular, for splenic wounds; and for blood vessel puncture diagnostic and treatment procedures such as catheterization and balloon angioplasty procedures.

The p-GlcNac based starting material, which can be formulated as a solid material or as a gel, foam, spray, emulsion, suspension, or solution comprising p-GlcNac microbeads, microspherse, or microfibrils, can be applied using standard surgical procedures, and can be used with both standard and minimally invasive surgical interventions. The gels of the invention can be delivered, for example, by extrusion from a syringe type device or in combination with a membrane or film. The membrane or film can be manufactured from a fully acetylated p-GlcNac based material or other natural or synthetic materials.

In connection with the blood vessel puncture procedures mentioned above, the compositions and materials of the invention, which are used to stimulate endothelin-1 secretion, vasoconstriction, and reduction of blood flow out of a breached vessel, may be applied at the time when a catheter sheath is being removed from a blood vessel by applying the p-GlcNac-based material directly to the skin in conjunction with manual compression, or introduced into the catheter track. Alternatively, a device that detects the removal of the catheter sheath from the blood vessel can be developed using electronic or mechanical systems that monitor chemical, physical or other differences between the tissue inside and outside of the vessel. For example, the differential in fluid dynamics or heat dissipation can be detected when a probe is removed from the vessel; at that point a signal is sent to initiate the application of the composition or material comprising p-GlcNac, which will stimulate release of endothelin-1, induce vasoconstriction, and/or reduce blood flow out of a breached vessel.

The methods of the present invention, which comprise topical administration of p-GlcNac, preferably fully acetylated, highly ordered, semi-crystalline polymers of p-GlcNac, to induce endothelin-1 release, vasoconstriction, and reduction of blood flow out of a breached vessel may be used in conjunction with those methods and compositions useful for achieving hemostasis. Such other methods and compositions include, but are not limited to (1) application of barrier-forming materials that provide a matrix impermeable to erythrocytes, and platelets and which may concentrate circulating factors required for the clotting cascade, and (2) application to a wound of materials comprising components of the clotting cascade including, for example, thrombin, fibrinogen, and Factor 13.

The methods of the present invention may also be used prophylactically to minimize the need for, or increase the efficiency of, methods and compositions for achieving hemostasis where a need therefor can be anticipated. Examples of such a need include, but are not limited to removal of polyps during gastroenterological procedures, excision of tumor tissue, and tooth extraction. In such instances, the methods of the present invention are used to induce transient, localized endothelin-1 release, vasoconstriction, and a reduction in blood flow out of a breached vessel in those tissues and vessels adjacent to or contiguous with a target tissue, thereby minimizing subsequent bleeding resulting from the procedure carried out on the patient.

6. EXAMPLE

Physical Characterization of Preparations of Pure p-GlcNac

Presented in this Example, are circular dichroism (CD) and infra-red spectra (IR) analyses of p-GlcNac and deacetylated p-GlcNac membranes.

6.1. Materials and Methods p-GlcNac and commercial "chitin" preparations:

The p-GlcNac used in the CD studies' was prepared using the Mechanical Force purification method described, above, in Section 5.3.1.

Commercial "chitin" was purchased from NovaChem, Ltd., PO Box 1030 Armdale, Halifax, Nova Scotia, Canada, B3L 4K9.

The p-GlcNac membranes used in the IR studies were prepared by either the Mechanical Force purification method as described, above, in Section 5.3.1, or by the Chemical/Biological purification method, as described, above, in Section 5.3.2, as indicated.

The commercial "p-GlcNac" preparations were cast into membranes by dissolving in a dimethylacetamide solution containing 5% lithium chloride, and layering onto distilled, deionized water until membranes precipitated.

p-GlcNac derivatives and treatments: The Deacetylated p-GlcNac used in both the CD and IR studies was prepared by treatment of the p-GlcNac with 50% NaOH at 60° C. for 2 hours. The heat-denatured p-GlcNac membranes used in the IR studies were modified by boiling in 0.2 mM EDTA for 3 minutes. p-GlcNac was autoclaved for 30 minutes at 122° C.

CD techniques: Solid state CD techniques were carried out essentially according to Domard (Domard, A., 1986, Int. J. Macromol. 8:243–246).

6.2. Results 6.2.1. CD Analysis

In the CD spectra obtained from untreated p-GlcNac (FIG. 3A), the expected n-$\pi$* and $\pi$-$\pi$* optically active electronic transitions (220–185 nM) were observed due to the presence of the carbonyl group in the acetyl moiety of p-GlcNac. Such peaks are completely absent in the CD spectrum obtained from the deacetylated p-GlcNac product, as shown in FIG. 3B.

6.2.2. IR Spectra Analysis

The IR spectra obtained in this study are consistent with the chemical structure of p-GlcNac. Additionally, the sharp definition of each IR peak is indicative of the presence of an ordered and regular (i.e., semi-crystalline) structure in the p-GlcNac fibers. See FIG. 4A for the IR spectrum of p-GlcNac purified via the Mechanical Force purification method, and FIG. 4D for the IR spectrum of p-GlcNac purified via the Chemical/Biological method. For comparison, see FIG. 4B, which demonstrates the IR spectrum of a commercial "chitin" preparation.

The IR spectrum obtained from the autoclaved p-GlcNac material (FIG. 4E) does not differ visibly from the IR spectrum observed in FIG. 4A. This data indicates that the p-GlcNac material may be sterilized by autoclaving with no loss of polymer structure.

7. EXAMPLE

Purification of p-GlcNac Using the Mechanical Force Purification Method

In this section, p-GlcNac was purified using the Mechanical Force technique described above, in Section 5.3.1.

7.1. Materials and Methods/Results

Diatom culture conditions: The diatom species *Thalassiosira fluviatilis* was grown in culture according the procedures described, above, in Sections 5.1 and 5.2.

SEM procedures: The SEM techniques used here are as those described, below, in Section 12.1.

p-GlcNac Purification procedure: p-GlcNac was purified from the diatom culture by utilizing the Mechanical Force technique described above, in Section 5.3.1. Specifically, the p-GlcNac fibers were separated from the diatom cell bodies by subjecting the contents of the culture to three short bursts of top speed mixing motion in a Waring blender Total time of the three bursts was about one second. The resulting suspension was centrifuged at 3500 rpm in a Sorvall GS-4 fixed angle rotor, for 20 minutes at about 10° C. The supernatant was decanted, and centrifuged again, this time at 4000 rpm, in a Sorvall GS-4 fixed angle rotor for 20 minutes at about 10° C. Once again, the supernatant was decanted and centrifuged at 4000 rpm at 10° C. The final supernatant of the third centrifugation was clear, with little, if any, visible flocs floating in the liquid. The clear supernatant was decanted into a Buchner filtration unit equipped with a Supor-800 polyether sulfone filter membrane with 0.8 µm pore size (Gelman, Inc.), suction was then applied and the liquid was filtered from the fiber suspension, allowing the fibers to be collected on the membrane. The collected fibers were washed with 1 liter of distilled, deionized $H_2O$ at 70° C. When almost all of the water had been drained, fibers were washed, with suction, with 1 liter of 1N HCl at 70° C. When most of the acid solution had been drained, the fibers were washed with 1 liter of distilled, deionized $H_2O$ at 70° C., using suction. When most of the wash water had been drained, the fibers were washed with 1 liter of 95% ethanol at room temperature, and vacuum was applied. The filter membrane on which the white fiber membrane had been collected was then removed from the filtration unit and the membrane and its membrane support was dried in a drying oven at 58° C. for 20 minutes, after which the membrane and its support were placed in a desiccator for 16 hours.

Following this purification procedure, the yield of p-GlcNac from a 1000 ml culture was 6.85 milligrams per liter of diatom culture. SEM photographs of the membrane formed by the collection of the p-GlcNac fibers via this technique is shown in FIG. 6.

8. EXAMPLE

Purification of p-GlcNac Using the Biological/Chemical Purification Method

In this section, p-GlcNac was purified using two of the Chemical/Biological techniques described above, in Section 5.3.2. Briefly, p-GlcNac was purified via HF treatment, in one case, and via acid treatment/neutralization in the second case.

8.1. Materials and Methods/Results

Diatom culture conditions: The diatom species *Thalassiosira fluviatilis* was grown in a culture according to the procedures described, above, in Sections 5.1 and 5.2.

SEM procedures: The techniques utilized in this study were as described, below, in Section 12.1.

Purification procedure: First, p-GlcNac was purified by HF treatment, the results of which are shown in FIG. 7. Specifically, under a fume hood, 2.42 ml of a 49% (29N) HF solution was added to the diatom contents of the culture, at room temperature, for each 1000 ml of the volume of the original cell culture, resulting in a 0.07M HF solution. The mixture was then shaken vigorously for about 30 seconds, causing persistent foam to appear over the liquid. The container was allowed to stand undisturbed for 5–6 hours to allow heavy particulates to settle. At the end of this time, a layer of foam had formed, while the liquid itself was divided into two strata: first, a narrow, very dark green layer resting on the bottom of the container below a second, much lighter colored grayish-green and murky phase which represented perhaps 85–90% of the total volume of liquid. The foam layer was carefully siphoned off, using a capillary glass tube and vacuum suction. The grayish cloudy supernatant was then siphoned off, with care being taken not to disturb the dark bottom layer, which consisted mainly of settled cell bodies, and was transferred to a separate plastic container. The grayish cloudy supernatant was allowed to stand undisturbed for an additional 16 hours. The liquid was initially almost colorless, light grey, but not transparent. After 16 hours settling time, a small amount of foam remained on top of the main body of liquid and a small amount of green matter had settled on the bottom of the container. The liquid was lighter in color, but still not transparent. The foam on top of the liquid was siphoned off as before. The main body of liquid was then carefully siphoned off, leaving behind the small amount of settled green material at the bottom of the container. The liquid which had thus been isolated, contained the majority of the p-GlcNac fibers and some impurities.

To remove proteins and other unwanted matter liberated by the diatoms during the preceding steps in the procedure from the fiber-containing liquid, the suspension of fibers and cell remnants was washed with sodium dodecyl sulfate (SDS). Specifically, the necessary volume of a 20% SDS solution was added to make the final concentration of the liquid 0.5% SDS by volume. The container holding the liquid was sealed, secured in a horizontal position on a shaking machine, and agitated for 24 hours at about 100 shakes a minute. Soon after shaking began, large flocs of white p-GlcNac fibers appeared in the suspension, and a considerable amount of foam accumulated in the head space of the containers. At the end of the SDS washing, the contents of the containers were transferred to a Buchner filtration equipment provided with a Supor-800 polyether sulfone filter membrane, with 0.8 micron pore size (Gelman, Inc.). The liquid was filtered with suction, and the p-GlcNac fibers in the liquid were collected on the filter membrane.

The p-GlcNac fibers collected on the filter membrane were then washed further. First, the fibers were washed with hot (70° C.) distilled, deionized $H_2O$, using three times the volume of the original suspension. With a water jet using distilled, deionized $H_2O$, the white fiber clumps collected on the filter membrane of the Buchner filter were transferred to a Waring blender, and the fiber clumps were disintegrated with about 10 short mixing bursts. The suspension of disintegrated fibers was transferred to a Buchner filter funnel equipped with a polyether sulfone filter membrane as described above, and the liquid was removed under suction. The collected fibers were washed with 1000 ml of hot (70° C.) 1N HCl solution, and subsequently further washed with 1000 ml hot (70° C.) distilled, deionized $H_2O$. Finally, the fibers were washed with 1000 ml 95% ethanol at room temperature, and filtered to dryness. The fiber membrane and the filter membrane supporting the fiber membrane were then dried in a drying oven at 58° C. for 20 minutes. The membrane and membrane support was then placed in a desiccator for 16 hours. The membrane was then carefully detached from the filter membrane.

Second, p-GlcNac was purified by using the acid treatment/neutralization method described, above, in Section 5.3.2. Specifically, the p-GlcNac was processed as described earlier in this Section, until prior to the SDS wash step, at which point the solution was neutralized to a pH of approximately 7.0 by the addition of a 2.9M Tris solution. The p-GlcNac yield from this particular purification procedure was 20.20 milligrams per liter of diatom culture, although, on average, approximately 60 milligrams per liter diatom culture are obtained. SEM micrographs of membranes formed during the purification procedure are shown in FIGS. 8A–B and 9A–9E.

9. EXAMPLE p-GlcNac Deacetylation

A p-GlcNac membrane was suspended in an aqueous 50% NaOH solution. The suspension was heated at 80° C. for 2 hours. The resulting deacetylated membrane was dried and studied by scanning electron microscopy, as shown in FIGS. 11A–B.

10. EXAMPLE p-GlcNac Biocompatibility

In this Example, it is demonstrated that the p-GlcNac starting material exhibits no detectable biological reactivity, as assayed by elution tests, intramuscular implantation in rabbits, intracutaneous injection in rabbits, and systemic injections in mice.

10.1. Materials and Methods

10.1.1. Elution Test

Conditions for the elution test conformed to the specifications set forth in the U.S. Pharmacopeia XXII, 1990, pp. 1415–1497 and to U.S. Pharmacopeia XXII, Supplement 5, 1991, pp. 2702–2703.

Cell culture: Mouse fibroblast L929 cell line (American Type Culture Collection Rockville, Md.; ATCC No. CCL1; NCTC clone 929) was utilized. A 24 hour confluent monolayer of L929 cells was propagated in complete Minimum Essential Medium (MEM).

p-GlcNac: a solid membrane of p-GlcNac which had been prepared according to the Mechanical Force method of purification described, above, in Section 5.3.1, was extracted in 20 ml serum-supplemented MEM as per U.S. Pharmacopeia XXII (1990) requirements.

Controls: Natural rubber was used as a positive control, and silicone was used as a negative control. Controls were tested in the same manner as the test article, p-GlcNac.

Extracts: Extracts were prepared at 37° C., in a humidified atmosphere containing 5% carbon dioxide, for 24 hours. Extracts were evaluated for a change in pH, and adjustments were made to bring the pH to within ±0.2 pH units of the original medium. Adjustments were made with HCl to lower the extract pH or with $NaHCO_3$ to raise the extract pH. Extracts were sterile filtered by passage through a 0.22 micron filter, prior to being applied to the cell monolayer.

Dosing: 3 mls of p-GlcNac or control extracts were used to replace the maintenance medium of cell cultures. All extracts were tested in duplicate.

Evaluation Criteria: Response of the cell monolayer was evaluated either visually or under a microscope. The biological reactivity, i.e., cellular degeneration and/or malformation, was rated on a scale of 0 to 4, as shown below. The test system is suitable if no signs of cellular reactivity (Grade 0) are noted for the negative control article, and the positive control article shows a greater than mild reactivity (Grade 2). The test article (i. e., p-GlcNac) meets the biocompatibility test if none of the cultures treated with the test article show a greater than mild reactivity.

| Grade | Reactivity | Description of Reactivity Zone |
|---|---|---|
| 0 | None | Discrete intracytoplasmic granules; No cell lysis |
| 1 | Slightly | Not more than 20% of the cells are round, loosely attached, and without intra- cytoplasmic granules; occasional lysed cells are present |
| 2 | Mild | Not more than 50% of the cells are round and devoid of intracytoplasmic granules; extensive cell lysis and empty areas between cells |
| 3 | Moderate | Not more than 70% of the cell layers contain rounded cells and/or are lysed |
| 4 | Severe | Nearly complete destruction of the cell layers |

10.1.2. Intramuscular Implantations

Animals: Healthy, New Zealand White Rabbits, male and female, (Eastern Rabbit Breeding Laboratory, Taunton, Mass.) were used. Rabbits were individually housed using suspended stainless steel cages. Upon receipt, animals were placed in quarantine for 8 days, under the same conditions, as for the actual test. Hardwood chips (Sani-chips™, J. P. Murphy Forest Products, Montvale, N.J.) were used as non-contact bedding under cages. The animal facility was maintained at a temperature of 68°±3° F., with a relative humidity at 30–70%, a minimum of 10–13 complete air exchanges per hour, and a 12-hour light/dark cycle using full spectrum fluorescent lights. Animals were supplied with commercial feed (Agway ProLab, Waverly, N.Y.) under controlled conditions and municipal tap water ad libitum. No known contaminants were present in the feed, bedding, or water which would be expected to interfere with the test results. Animals selected for the study were chosen from a larger pool of animals. Rabbits were weighted to nearest 10 g and individually identified by ear tattoo.

p-GlcNac: The p-GlcNac used was as described, above, in Section 10.1.1.

Implantation Test: Two rabbits were used for each implantation test. On the day of the test, the animal skin on both sides of the spinal column was clipped free of fur. Each animal was anesthetized to prevent muscular movement. Using sterile hypodermic needles and stylets, four strips of the test p-GlcNac (1 mm×1 mm×10 mm) were implanted into the paravertebral muscle on one side of the spine of each of two rabbits (2.5 to 5 cm from the midline, parallel to the spinal column, and about 2.5 cm from each other). In a similar fashion, two strips of the USP negative control plastic RS (1 mm×1 mm×10 mm) were implanted in the opposite muscle of each animal. Animals were maintained for a period of 7 days. At the end of the observation period, the animals were weighed and euthanized by an injectable barbiturate, Euthanasia-5 (Veterinary Laboratories, Inc., Lenexa, Kans.). Sufficient time was allowed to elapse for the tissue to be cut without bleeding. The area of the tissue surrounding the center portion of each implant strip was examined macroscopically using a magnifying lens. Hemorrhaging, necrosis, discolorations and infections were scored using the following scale: 0=Normal, 1=Mild, 2=Moderate, and 3=Severe. Encapsulation, if present, was scored by first measuring the width of the capsule (i.e., the distance from the periphery of the implant to the periphery of the capsule) rounded to the nearest 0.1 mm. The encapsulation was scored as follows:

| Capsule Width | Score |
|---|---|
| None | 0 |
| up to 0.5 mm | 1 |
| 0.6–1.0 mm | 2 |
| 1.1–2.0 mm | 3 |
| Greater than 2.0 mm | 4 |

The differences between the average scores for the p-GlcNac and the positive control article were calculated. The test is considered negative if, in each rabbit, the difference between the average scores for each category of biological reaction for the p-GlcNac and the positive control plastic implant sites does not exceed 1.0; or, if the difference between the mean scores for all categories of biological reaction for each p-GlcNac article and the average score for all categories for all the positive control plastic implant sites does not exceed 1.0, for not more than one of four p-GlcNac strips.

10.1.3. Intracutaneous Injections

Animals: New Zealand white rabbits were used and maintained as described, above, in Section 10.1.2.

p-GlcNac: A solid membrane of p-GlcNac which had been prepared according to the mechanical force method of purification described, above, in Section 5.3.1, was placed in an extraction flask, to which 20 ml of the appropriate medium were added. Extractions were performed by heating to 70° C. for 24 hours. Following this procedure, extracts were cooled to room temperature. Each extraction bottle was shaken vigorously prior to administration.

Intracutaneous Test: On the day of the test, animals were clipped free of fur on the dorsal side. A volume of 0.2 ml of each p-GlcNac extract was injected intracutaneously at five sites on one side of each of two rabbits. More than one p-GlcNac extract was used per rabbit. At five sites on the other side of each rabbit, 0.2 ml of the corresponding control was injected. Injection sites were observed for signs of erythema, edema, and necrosis at 24, 48, and 72 hours after injection. Observations were scored according to the Draize Scale for the Scoring Skin Reaction (USP Pharmacopeia XXII, 1990, 1497–1500; USP Pharmacopeia XXII, Supplement 5, 1991, 2703–2705) as shown in Table II, below:

TABLE II

Draize Scale for Scoring Skin Reactions

| | Value |
|---|---|
| Erythema and Eschar Formation | |
| No erythema | 0 |
| Very slight erythema (barely perceptible) | 1 |
| Well defined erythema | 2 |
| Moderate to severe erythema | 3 |
| Severe erythema (beet redness) to slight eschar formation (inuries in depth) | 4 |
| Total possible erythema score = 4 | |
| Edema Formation | |
| No edema | 0 |
| Very slight erythema (barely perceptible) | 1 |
| Slight edema (edges are well defined by definite raising) | 2 |
| Moderate edema (raised approximately 1 mm and extending beyond area of exposure) | 3 |
| Severe edema (raised more than 1 mm and extending beyond area of exposure) | 4 |
| Total possible edema score = 4 | |

All erythema and edema scores at 24, 48, and 72 hours were totaled separately and divided by 12 (i.e., 2 animals×3 scoring periods×2 scoring categories) to determine the overall mean score for the p-GlcNac versus the corresponding control. Animals were weighed at the end of the observation period and euthanized by injection of a barbiturate, Euthanasia-5 (Veterinary Laboratories, Inc., Lenexa, Kans.). The results of the test are met if the difference between the p-GlcNac and the control means reaction scores (erythema/edema) is 1.0 or less.

10.1.4. Systemic Injections

Animals: Albino Swiss mice (Mus musculus), female, (Charles River Breeding Laboratories, Wilmington, Mass.) were used. Groups of 5 mice were housed in polypropylene cages fitted with stainless steel lids. Hardwood chips (Sanichips™, J. P. Murphy Forest Products, Montvale, N.J.) were used as contact bedding in the cages. The animal facility was maintained as a limited access area. The animal rooms were kept at a temperature of 68°±3° F., with a relative humidity of 30–70%, a minimum of 10–13 complete air exchanges per hour, and a 12 hour light/dark cycle using full spectrum fluorescent lights. Mice were supplied with commercial feed and municipal tap water ad libitum. There were no known contaminants present in the feed, bedding, or water which would be expected to interfere with the test results. Animals selected for the study were chosen from a larger pool of animals. Mice were weighed to the nearest 0.1 g and individually identified by ear punch.

p-GlcNac: The samples used were as described, above, in Section 10.1.1. . . Extracts were prepared according to the procedures described in Section 10. 1.3, above.

Systemic Injection Test: Groups of 5 mice were injected with either p-GlcNac extract or a corresponding control article, in the same amounts and by the same routes as set forth below:

| Test Article Control or Article Extracts | Dosing Route | Dose/Kg | Injection Rate |
|---|---|---|---|
| 0.9% Sodium Chloride Injection, USP (0.9% NaCl) | Intravenous | 50 ml | 0.1 ml/sec |
| 1 in 20 Alcohol in 0.9% Sodium Chloride Injection USP (EtOH:NaCl) | Intravenous | 50 ml | 0.1 ml/sec |
| Polyethylene Glycol 400 (PEG 400) | Intraperitoneal | 10 g | — |
| Cottonseed Oil (CSO) | Intraperitoneal | 50 ml | — |

Extracts of the p-GlcNac prepared with PEG 400, and the corresponding control, were diluted with 0.9% NaCl, to obtain 200 mg of PEG 400 per ml. For the Intracutaneous Test, PEG 400 was diluted with 0.9% NaCl to obtain 120 mg of PEG 400 per ml.

The animals were observed immediately after injection, at 24 hours, 48 hours, and 72 hours after injection. Animals were weighed at the end of the observation period and euthanized by exposure to carbon dioxide gas. The requirements of the test are met if none of the animals treated with the p-GlcNac shows a significantly greater biological reactivity than the animals treated with the control article.

10.2. Results 10.2.1. Elution Test

The response of the cell monolayer to the p-GlcNac test article was evaluated visually and under a microscope. No cytochemical stains were used in the evaluation. No signs of cellular biological reactivity (Grade 0) were observed by 48 hours post-exposure to the negative control article or to the p-GlcNac. Severe reactivity (Grade 4) was noted for the positive control article, as shown below in Table III:

TABLE III

REACTIVITY GRADES

|  | p-GlcNac | | Control Articles | | | |
|---|---|---|---|---|---|---|
|  |  |  | Negative | | Positive | |
| Time | A | B | A | B | A | B |
| 0 Hours | 0 | 0 | 0 | 0 | 0 | 0 |
| 24 Hours | 0 | 0 | 0 | 0 | 4 | 4 |
| 48 Hours | 0 | 0 | 0 | 0 | 4 | 4 |

The p-GlcNac starting material, therefore, passes requirements of the elution test for iocompatibility, and, thus, is noncytotoxic.

10.2.2. Intramuscular Implantations

Both rabbits (A and B) tested increased in body weight and exhibited no signs of toxicity. See Table IV for data. In addition, there were no overt signs of toxicity noted in either animal. Macroscopic evaluation of the test and control article implant sites showed no inflammation, encapsulation, hemorrhage, necrosis, or discoloration. See Table IV for results. The test, therefore, demonstrates that the p-GlcNac assayed exhibits no biological reactivities, in that, in each rabbit, the difference between the average scores for all of the categories of biological reaction for all of the p-GlcNac implant sites and the average score for all categories for all the control implant sites did not exceed 1.0.

TABLE IV

IMPLANTATION TEST
(Macroscopic Observations)
Test Article: p-GlcNac
Animal Species: Rabbit

| Tissue Site: | T1 | T2 | T3 | T4 | Test Average | C1 | C2 | Control Average |
|---|---|---|---|---|---|---|---|---|
| Animal #: A | | | | | | | | |
| Inflammation | 0 | 0 | 0 | 0 | 0 | 0 | 0 | 0 |
| Encapsulation | 0 | 0 | 0 | 0 | 0 | 0 | 0 | 0 |
| Hemorrhage | 0 | 0 | 0 | 0 | 0 | 0 | 0 | 0 |
| Necrosis | 0 | 0 | 0 | 0 | 0 | 0 | 0 | 0 |
| Discoloration | 0 | 0 | 0 | 0 | 0 | 0 | 0 | 0 |
| Total | 0 | 0 | 0 | 0 |  | 0 | 0 |  |
| MEAN SCORE: (total/5) | 0 | 0 | 0 | 0 |  | 0 | 0 |  |
| AVERAGE CONTROL VALUE: | | | | | | | | 0 |
| Animal #: B | | | | | | | | |
| Inflammation | 0 | 0 | 0 | 0 | 0 | 0 | 0 | 0 |
| Encapsulation | 0 | 0 | 0 | 0 | 0 | 0 | 0 | 0 |
| Hemorrhage | 0 | 0 | 0 | 0 | 0 | 0 | 0 | 0 |
| Necrosis | 0 | 0 | 0 | 0 | 0 | 0 | 0 | 0 |
| Discoloration | 0 | 0 | 0 | 0 | 0 | 0 | 0 | 0 |
| Total | 0 | 0 | 0 | 0 |  | 0 | 0 | 0 |
| MEAN SCORE: (total/5) | 0 | 0 | 0 | 0 |  | 0 | 0 |  |
| AVERAGE CONTROL VALUE: | | | | | | | | 0 |

10.2.3 Intracutaneous Test

All of the animals increased in weight. See Table V for data. There were no signs of erythema or edema observed at any of the p-GlcNac or control article sites. Overt signs of toxicity were not observed in any animal. Because the difference between the p-GlcNac and control article mean reaction scores (erythema/edema) was less than 1.0, the p-GlcNac meets the requirements of the intracutaneous test.

See Table VI for results. Therefore, as assayed by this test, the p-GlcNac demonstrates no biological reactivity.

TABLE V

Intracutaneous and Implant Tests
Body Weights and Clinical Observations
Test Article: p-GlcNac Animal Species: Rabbit

| Group | Animal # | Sex | Body Weight (Kg) Day 0 | Body Weight (Kg) Day 3 | Weight Change | Signs of Toxicity* |
|---|---|---|---|---|---|---|
| 0.9% NaCl & CSO | 23113 | Male | 2.51 | 2.55 | 0.04 | None |
| 0.9% NaCl & CSO | 23114 | Male | 2.43 | 2.46 | 0.03 | None |
| EtOH: NaCl & PEG 400 | 23115 | Male | 2.47 | 2.50 | 0.03 | None |
| EtOH: NaCL & PEG 400 | 23116 | Male | Male | 2.63 | 0.04 | None |

| Group | Animal # | Sex | Body Weight (Kg) Day 0 | Body Weight (Kg) Day 7 | Weight Change | Signs of Toxicity* |
|---|---|---|---|---|---|---|
| Implant | A | Male | 2.74 | 2.80 | 0.06 | None |
|  | B | Female | 2.66 | 2.74 | 0.08 | None |

*Summary of Observations Day 0 Through Day 7 (Implant) and Day 0 through Day 3 (Intracutaneous).

TABLE VI

INTRACUTANEOUS TEST DRAIZE SCORES
Test Article: p-GlcNac
(T = test, C = control) Animal Species: Rabbit

| Animal ID # | Vehicle | T-1 | C-1 | T-2 | C-2 | T-3 | C-3 | T-4 | C-4 | T-5 | C-5 | Time: | T | C |
|---|---|---|---|---|---|---|---|---|---|---|---|---|---|---|
| | NaCl Extract |
| 23113 | NaCl | 0/0 | 0/0 | 0/0 | 0/0 | 0/0 | 0/0 | 0/0 | 0/0 | 0/0 | 0/0 | 24 hr. | 0/0 | 0/0 |
|  |  | 0/0 | 0/0 | 0/0 | 0/0 | 0/0 | 0/0 | 0/0 | 0/0 | 0/0 | 0/0 | 48 hr | 0/0 | 0/0 |
|  |  | 0/0 | 0/0 | 0/0 | 0/0 | 0/0 | 0/0 | 0/0 | 0/0 | 0/0 | 0/0 | 72 hr. | 0/0 | 0/0 |
|  | Total | 0/0 | 0/0 | 0/0 | 0/0 | 0/0 | 0/0 | 0/0 | 0/0 | 0/0 |  |  | 0/0 | 0/0 |
| 23114 | NaCl | 0/0 | 0/0 | 0/0 | 0/0 | 0/0 | 0/0 | 0/0 | 0/0 | 0/0 | 0/0 | 24 hr. | 0/0 | 0/0 |
|  |  | 0/0 | 0/0 | 0/0 | 0/0 | 0/0 | 0/0 | 0/0 | 0/0 | 0/0 | 0/0 | 48 hr. | 0/0 | 0/0 |
|  |  | 0/0 | 0/0 | 0/0 | 0/0 | 0/0 | 0/0 | 0/0 | 0/0 | 0/0 | 0/0 | 72 hr. | 0/0 | 0/0 |
|  | Total | 0/0 | 0/0 | 0/0 | 0/0 | 0/0 | 0/0 | 0/0 | 0/0 | 0/0 |  |  | 0/0 | 0/0 |
| | CSO Extract |
| 23113 | CSO | 0/0 | 0/0 | 0/0 | 0/0 | 0/0 | 0/0 | 0/0 | 0/0 | 0/0 | 0/0 | 24 hr. | 0/0 | 0/0 |
|  |  | 0/0 | 0/0 | 0/0 | 0/0 | 0/0 | 0/0 | 0/0 | 0/0 | 0/0 | 0/0 | 48 hr. | 0/0 | 0/0 |
|  |  | 0/0 | 0/0 | 0/0 | 0/0 | 0/0 | 0/0 | 0/0 | 0/0 | 0/0 | 0/0 | 72 hr. | 0/0 | 0/0 |
|  | Total | 0/0 | 0/0 | 0/0 | 0/0 | 0/0 | 0/0 | 0/0 | 0/0 | 0/0 |  |  | 0/0 | 0/0 |
| 23114 | CSO | 0/0 | 0/0 | 0/0 | 0/0 | 0/0 | 0/0 | 0/0 | 0/0 | 0/0 | 0/0 | 24 hr. | 0/0 | 0/0 |
|  |  | 0/0 | 0/0 | 0/0 | 0/0 | 0/0 | 0/0 | 0/0 | 0/0 | 0/0 | 0/0 | 48 hr. | 0/0 | 0/0 |
|  |  | 0/0 | 0/0 | 0/0 | 0/0 | 0/0 | 0/0 | 0/0 | 0/0 | 0/0 | 0/0 | 72 hr. | 0/0 | 0/0 |
|  | Total | 0/0 | 0/0 | 0/0 | 0/0 | 0/0 | 0/0 | 0/0 | 0/0 | 0/0 |  |  | 0/0 | 0/0 |
| | NaCl/EtOH Extract |
| 23115 | NaCl | 0/0 | 0/0 | 0/0 | 0/0 | 0/0 | 0/0 | 0/0 | 0/0 | 0/0 | 0/0 | 24 hr. | 0/0 | 0/0 |
|  | EtOH | 0/0 | 0/0 | 0/0 | 0/0 | 0/0 | 0/0 | 0/0 | 0/0 | 0/0 | 0/0 | 48 hr. | 0/0 | 0/0 |
|  |  | 0/0 | 0/0 | 0/0 | 0/0 | 0/0 | 0/0 | 0/0 | 0/0 | 0/0 | 0/0 | 72 hr. | 0/0 | 0/0 |
|  | Total | 0/0 | 0/0 | 0/0 | 0/0 | 0/0 | 0/0 | 0/0 | 0/0 | 0/0 |  |  | 0/0 | 0/0 |
| 23116 | NaCl | 0/0 | 0/0 | 0/0 | 0/0 | 0/0 | 0/0 | 0/0 | 0/0 | 0/0 | 0/0 | 24 hr. | 0/0 | 0/0 |
|  | EtOH | 0/0 | 0/0 | 0/0 | 0/0 | 0/0 | 0/0 | 0/0 | 0/0 | 0/0 | 0/0 | 48 hr. | 0/0 | 0/0 |
|  |  | 0/0 | 0/0 | 0/0 | 0/0 | 0/0 | 0/0 | 0/0 | 0/0 | 0/0 | 0/0 | 72 hr. | 0/0 | 0/0 |
|  | Total | 0/0 | 0/0 | 0/0 | 0/0 | 0/0 | 0/0 | 0/0 | 0/0 | 0/0 |  |  | 0/0 | 0/0 |

TABLE VI-continued

INTRACUTANEOUS TEST DRAIZE SCORES
Test Article: p-GlcNac
(T = test, C = control) Animal Species: Rabbit

| Animal ID # | Vehicle | Site Numbers | | | | | | | | | | Scoring (ER/ED) | | | | | | Averages | | |
|---|---|---|---|---|---|---|---|---|---|---|---|---|---|---|---|---|---|---|---|---|
| | | T-1 | C-1 | T-2 | C-2 | T-3 | C-3 | T-4 | C-4 | T-5 | C-5 | | | | | | Time: | T | C |
| | | | | | | PEG Extract | | | | | | | | | | | | | |
| 23115 | PEG | 0/0 | 0/0 | 0/0 | 0/0 | 0/0 | 0/0 | 0/0 | 0/0 | 0/0 | 0/0 | | | | | | 24 hr. | 0/0 | 0/0 |
| | | 0/0 | 0/0 | 0/0 | 0/0 | 0/0 | 0/0 | 0/0 | 0/0 | 0/0 | 0/0 | | | | | | 48 hr. | 0/0 | 0/0 |
| | | 0/0 | 0/0 | 0/0 | 0/0 | 0/0 | 0/0 | 0/0 | 0/0 | 0/0 | 0/0 | | | | | | 72 hr. | 0/0 | 0/0 |
| | Total | 0/0 | 0/0 | 0/0 | 0/0 | 0/0 | 0/0 | 0/0 | 0/0 | 0/0 | 0/0 | | | | | | | 0/0 | 0/0 |
| 23115 | PEG | 0/0 | 0/0 | 0/0 | 0/0 | 0/0 | 0/0 | 0/0 | 0/0 | 0/0 | 0/0 | | | | | | 24 hr. | 0/0 | 0/0 |
| | | 0/0 | 0/0 | 0/0 | 0/0 | 0/0 | 0/0 | 0/0 | 0/0 | 0/0 | 0/0 | | | | | | 48 hr. | 0/0 | 0/0 |
| | | 0/0 | 0/0 | 0/0 | 0/0 | 0/0 | 0/0 | 0/0 | 0/0 | 0/0 | 0/0 | | | | | | 72 hr. | 0/0 | 0/0 |
| | Total | 0/0 | 0/0 | 0/0 | 0/0 | 0/0 | 0/0 | 0/0 | 0/0 | 0/0 | 0/0 | | | | | | | 0/0 | 0/0 |

10.2.4. Systemic Test

All of the mice treated with the p-GlcNac extract or the control article increased in weight. See Table VII for data. In addition, there were no overt signs of toxicity observed in any p-GlcNac or control animal. See Table VI for results. It is concluded, therefore, that none of the p-GlcNac test animals showed a significantly greater biological reactivity than the animals treated with the control article.

TABLE VII

ANIMAL WEIGHTS AND CLINICAL OBSERVATIONS

| Group | Sex | Dose (ml) | Animal # | Body Weight (g) | | Weight Change | Signs of Toxicity* |
|---|---|---|---|---|---|---|---|
| | | | | Day 0 | Day 3 | | |
| NaCl | Female | 1.03 | I. | 20.6 | 22.8 | 2.2 | None |
| EtOH | Female | 1.06 | II. | 21.1 | 23.4 | 2.3 | None |
| Test | Female | 1.02 | III. | 20.4 | 22.6 | 2.2 | None |
| 50 | Female | 1.11 | IV. | 22.2 | 24.5 | 2.3 | None |
| ml/kg | Female | 1.05 | V. | 21.0 | 23.2 | 2.2 | None |
| | | | Mean | 21.1 | 23.3 | | |
| | | | SD± | 0.7 | 0.7 | | |
| NaCl: | Female | 1.04 | VI. | 20.7 | 23.2 | 2.5 | None |
| EtOH | Female | 1.04 | VII. | 20.8 | 23.5 | 2.7 | None |
| Control | Female | 1.02 | VIII. | 20.3 | 22.3 | 2.0 | None |
| 50 | Female | 0.91 | IX. | 18.2 | 20.6 | 2.4 | None |
| ml/kg | Female | 0.94 | X. | 1.9 | 20.9 | 2.2 | None |
| | | | Mean | 19.7 | 22.1 | | |
| | | | SD± | 1.2 | 1.3 | | |
| PEG | Female | 1.02 | XI. | 20.3 | 22.7 | 2.4 | None |
| Test | Female | 0.96 | XII. | 19.2 | 21.4 | 2.2 | None |
| 10 | Female | 0.95 | XIII. | 18.9 | 21.6 | 2.7 | None |
| ml/kg | Female | 1.05 | XIV. | 20.9 | 22.7 | 1.8 | None |
| | Female | 0.94 | XV. | 18.7 | 21.2 | 2.5 | None |
| | | | Mean | 19.6 | 21.9 | | |
| | | | SD± | 1.0 | 0.7 | | |
| PEG | Female | 1.01 | XVI. | 20.1 | 22.3 | 2.2 | None |
| Control | Female | 0.99 | XVII. | 19.8 | 22.0 | 2.3 | None |
| 10 | Female | 1.10 | XVIII. | 22.0 | 24.3 | 2.3 | None |
| g/kg | Female | 1.07 | XIX. | 21.4 | 23.6 | 2.2 | None |
| | Female | 1.03 | XX. | 20.6 | 22.4 | 1.8 | None |
| | | | Mean | 20.8 | 22.9 | | |
| | | | SD± | 0.9 | 1.0 | | |

*Summary of observations 0, 4, 24, 48, and 72 h after injection

11. EXAMPLE p-GlcNac Reformulation

In the Working Example presented in this Section, a p-GlcNac membrane (16.2 mg) was dissolved in 1 ml of a dimethylacetamide solution containing 5% LiCl. The p-GlcNac-containing solution was placed in a syringe and extruded into 50 ml of pure water to precipitate a fiber. The resulting fiber was studied with scanning electron microscopy, as shown in FIGS. 10A–B.

12. EXAMPLE p-GlcNac/Collagen Hybrids

Presented in this Working Example is the formation and characterization of a p-GlcNac/collagen hybrid material.

12.1. Materials and Methods

Materials: Bovine Type I collagen was used in preparation of the hybrids described in this study. p-GlcNac was prepared according to the mechanical force method described, above, in Section 5.3.2.

Hybrid preparation: Collagen (10 milligrams/ml) and p-GlcNac (0.25 milligrams/ml) aqueous suspensions were mixed, in different ratios, frozen in liquid $N_2$ (−80° C.), held at −9° C. for 4 hours, and lyophilized. Material was dehydrothermally cross-linked under vacuum (approximately 0.030 Torr) at 60° C. for 3 days.

Cell Culture: Mouse 3T3 fibroblast cells were grown on the collagen/p-GlcNac hybrids produced. Standard culturing procedures were followed, and SEM micrographs were taken after 8 days in culture.

12.2. Results

Collagen and p-GlcNac aqueous suspensions were mixed in differing ratios (namely, 3:1, 1:1, 2:2, and 1:3 collagen: p-GlcNac suspension ratios), frozen, lyophilized, and crosslinked. Such a procedure yielded collagen/p-GlcNac slabs. SEM micrographs of the resulting materials revealed the porous structure of the hybrid material, which provides an efficient three-dimensional structure for the attachment and growth of cells.

13. EXAMPLE

NMR Characterization of Pure Preparations of p-GlcNac

Presented in this Example is an NMR (nuclear magnetic resonance) analysis of a pure p-GlcNac preparation.

13.1. Materials and Methods p-GlcNac preparations: The p-GlcNac used in the NMR studies described here was prepared using the chemical purification method described, above, in Section 5.3.2, with hydrofluoric acid utilized as the chemical reagent.

NMR techniques: Solid state NMR data was obtained using a Bruker 500 MHz NMR spectrometer. Computer image analysis was used to transform the raw NMR spectrum data so as to eliminate background and to normalize baselines. An example of such transformed data are shown in FIG. 14. Transformed NMR curves such as that in FIG. 14 were used to obtain areas for every carbon atom type, and then to calculate the ratios of $CH_3$(area) to C-atom(area). Such values, obtained as described, are provided in FIG. 16.

13.2. Results

Solid state NMR data was obtained by measuring the $^{13}$C-NMR spectrum of a 500 mg sample of p-GlcNac. A typical NMR spectrum is shown in FIG. 15. The individual peaks represent the contribution to the spectrum of each unique carbon atom in the molecule. The relative percentage of each type of carbon atom in the molecule was determined dividing the area of the peak generated by that carbon species by the total sum of the areas under all of the NMR peaks obtained in the spectrum. Thus, it was possible to calculate the ratio of each of the atoms of the molecule measured by a reference atom. All p-GlcNac molecules consist of N-acetylated glucosamine residues having C1, C2, C3, C4, C5 and C6 atoms, by definition. The ratio, then, of the area of the N-acetyl $CH_3$ carbon atom peak to the areas of any of the glucosamine residue carbon atom peaks, above, should be 1.0 if all of the glucosamine residues in the polymer are N-acetylated. Data such as those in FIG. 14 were used to obtain values for the $CH_3$(area) ratios.

The calculated ratios in FIG. 16 are in many cases equal to or nearly equal to 1.0, within experimental error, e.g. $CH_3/C2=1.097$, $CH_3/C6=0.984$, $CH_3/C5=1.007$, $CH_3/C1=0.886$. These results are consistent with the conclusion that the p-GlcNac starting material is free of contaminants and is fully acetylated (i.e. that essentially 100% of the glucosamine residues are N-acetylated).

14. EXAMPLE

Synthesis and Biological Characterization of Controlled Pore Size Three-dimensional p-GlcNac Matrices Described below, are methods for the production of three-dimensional p-GlcNac based porous matrices having controlled average pore sizes. Such matrices have a variety of important applications, including for example, as means for the encapsulation of cells. Such cell encapsulation compositions are useful as transplantable cell-based therapeutics, and in other cell and tissue engineering applications such as in cartilage regeneration. The capability to manipulate the morphology and dimensionality of p-GlcNac materials, as demonstrated here, provides a powerful tool for reformulating p-GlcNac polymers into a variety of shapes, including without limitation, microbeads and microspheres, which may be formulated as emulsions, suspensions and/or solutions in a pharmaceutically acceptable carrier, vehicle, and/or solvent.

14.1. Materials and Methods p-GlcNac starting material: p-GlcNac was prepared using the chemical purification method described, above, in Section 5.3.2, with hydrofluoric acid utilized as the chemical reagent. Matrix formation: Suspensions (5 mls) containing 20 mg p-GlcNac samples were made in the solvents listed below in Section 14.2, prior to lyophilization. Samples were then poured into wells of tissue culture dishes and frozen at −20° C. The frozen samples were then lyophilized to dryness, and the resulting three-dimensional matrices were removed.

Scanning electron microscopy techniques: The procedures utilized here were performed as described, above, in Section 12.1. The images shown in FIGS. 17A–G. are 200× magnifications of the matrix material, and a scale marking of 200 microns is indicated on each of these figures.

14.2. Results p-GlcNac suspensions were obtained with each of the following solvents, as described, above, in Section 14.1:

| | |
|---|---|
| A. | Distilled water |
| B. | 10% methanol in distilled water |
| C. | 25% methanol in distilled water |
| D. | Distilled water only |
| E. | 10% ethanol in distilled water |
| F. | 25% ethanol in distilled water |
| G. | 40% ethanol in distilled water |

Samples of matrix formed using each of the solvents were subjected to scanning electron microscopic (SEM) analysis, as shown in FIGS. 17A–G. These figures reveal that the average matrix pore size decreases as the percentage of either methanol or ethanol increases in each suspension.

Specifically, pore diameter in the two water suspensions (FIGS. 17A and 17D) approach 200 microns on average. Pore size in the samples depicted in FIGS. 17C and 17F (25% methanol and ethanol, respectively) are between 30 and 50 microns on average.

The results shown here suggest that while both ethanol and methanol may be successfully used to control p-GlcNac pore size, ethanol may be more efficient than methanol.

15. EXAMPLE

Biodegradability of p-GlcNac Materials

The Example presented in this Section demonstrates that p-GlcNac starting materials may be prepared which exhibit controllable in vitro and in vivo biodegradability and rates of resorption.

15.1. Materials and Methods p-GlcNac materials: Prototype I was made by the method described, above, in Section 5.3.2, via the chemical method, with hydrofluoric acid being utilized as the chemical reagent. Prototype I represented 100% acetylated p-GlcNac.

The p-GlcNac starting material of prototype 3A was made by the method described, above, in Section 5.3.2, via the chemical method, with hydrofluoric acid being utilized as the chemical reagent. The p-GlcNac material was then deacetylated by the method described, above, in Section 5.4. Specifically, the p-GlcNac material was treated with a 40% NaOH solution at 60° C. for 30 minutes. The resulting prototype 3A was determined to be 30% deacetylated.

The p-GlcNac starting material of prototype 4 was made by the method described, above, in Section 5.3.2, via the chemical method, with hydrofluoric acid being utilized as the chemical reagent. The p-GlcNac material was then deacetylated by treatment with a 40% NaOH solution at 60° C. for 30 minutes. Next, the fibers were suspended in distilled water frozen at −20° C. and lyophilized to dryness Prototype 4 was also determined to be 30% deacetylated.

Abdominal implantation model: Sprague Dawley albino rats were utilized for the abdominal implantation model studies. Animals were anesthetized and prepared for surgery, and an incision was made in the skin and abdominal muscles. The cecum was located and lifted out. A 1 cm×1 cm membrane of p-GlcNac material was placed onto the cecum, and the incision was closed with nylon. Control animals were those in which no material was placed onto the cecum.

Animals were opened at 14 and 21 days post implantation. Photographs were taken during the implant and explant procedures (FIGS. 23A–E). Samples of cecum were prepared for histopathology after the explant procedure.

p-GlcNac in vitro degradation lysozyme-chitinase assay: The assay is a colorimetric assay for N-acetyl glucosamine, and was performed as follows: 150 µl of a reaction sample was pipetted into 13×100 mm glass disposable test tubes, in duplicate 25 µl of 0.25M potassium phosphate buffer (pH 7.1) was added to each test tube, followed by the addition of 35 µl of 0.8M potassium borate solution (pH 9.8). Tubes were immediately immersed into an ice-bath for a minimum of 2 minutes. Samples were then removed from the ice-bath, 1 ml of freshly prepared DMAB reagent was added, and the samples were vortexed. DMAB (Dimethyl aminobenzaldehyde) reagent was made by adding 70 mls of glacial acetic acid and 10 ml of 11.6N (concentrated) HCl to 8 grams of p-dimethyl aminobenzaldehyde. Samples were then incubated at 37° C. for 20 minutes.

To prepare a standard curve, the following procedure was utilized. A GlcNac stock solution was diluted to 0.1 mg/ml with 0.010M sodium acetate buffer (pH 4.5), and 0 µl, 20 µl, 30 µl, 90 µl or 120 µl of the diluted GlcNac solution was added to a set of test tubes. This was followed by the addition of 150 µl, 130 µl, 60 µl or 30 µl, respectively, of 0.010M sodium acetate buffer (pH 4.5) to the test tubes. Next, 25 µl of 0.25M potassium phosphate buffer (pH 7.1) and 35 µl of 0.8M potassium borate buffer (pH 9.8) were added to each test tube. A duplicate set of test tubes is prepared by the same procedure.

The test tubes are capped and boiled at 100° C. for exactly 3 minutes. The tubes are then immersed in an ice bath. The tubes are removed from the ice bath and 1 ml of DMAB reagent, freshly prepared according to the method described above, is added to each tube. The tubes are incubated at 37° C. for 20 minutes. The absorbance of the contents of each tube is read at 585 nM. Absorbance should be read as quickly as possible. The standard curve is plotted on graph paper and used to determine the concentration of N-acetyl glucosamine in the reaction samples. A typical standard curve is shown in FIG. 18.

15.2. Results

The in-vitro biodegradability of p-GlcNac materials was studied in experiments which assayed the relative susceptibility of p-GlcNac membrane materials to degradation by lysozyme. p-GlcNac membranes were exposed to an excess of lysozyme in a 10 mM acetate buffer, and the subsequent release of N-acetyl glucosamine was determined using the assay described, above, in Section 15.1.

The results of these experiments indicated that partially deacetylated membranes are more susceptible to digestion by lysozyme (see FIG. 19) and, further, that the rate of lysozyme degradation is directly related to the extent of deacetylation (see FIG. 20, which compares the degradation rates of a 50% to a 25% deacetylated p-GlcNac membrane).

p-GlcNac in vivo Degradation

Experiments were performed which addressed the in-vivo biodegradability of p-GlcNac materials. Such experiments utilized an abdominal implantation model. Three p-GlcNac materials, as listed below, were tested.

p-GlcNac Materials Tested:
1) p-GlcNac, fully acetylated (designated prototype 1);
2) partially deacetylated p-GlcNac membrane (designated prototype 3A); and
3) lyophilized and partially deacetylated p-GlcNac membrane(designated prototype 4).

Results

The fully acetylated p-GlcNac (prototype 1) was resorbed within 21 days, as shown in FIGS. 21A–21C. The partially deacetylated p-GlcNac membrane (prototype 3A) was completely resorbed within 14 days, as shown in FIGS. 21D–21E. The lyophilized and partially deacetylated p-GlcNac membrane (prototype 4) had not yet been completely resorbed after 21 days post-implantation.

Histopathology analyses showed that once the p-GlcNac material has been resorbed there were no histological differences detectable between tissue samples obtained from the treated and from the control animals.

16. EXAMPLE p-GlcNac Stimulation of Endothelin-1 Secretion and Induction of Arterial Vasoconstriction This example demonstrates that p-GlcNac of the present invention can be used to stimulate endothelin-1 release and to induce arterial vasoconstriction in vivo.

16.1. Treatment and Analysis of Aortic Incisions; Materials and Methods

ANIMALS. This study was conducted in immature female Yorkshire White swine weighing between 25 and 30 kg (average 27.5 kg). The following protocol was used in every case.

Protocol

1. After standard premedication, anesthetize animal by inhalation with 100% $O_2$ and 1–2% Halothane.
2. Draw control blood sample for CBC and platelet count.
3. Expose abdominal aorta.
4. With ties in place, make 1 cm vertical wound in aorta.
5. Release ties while applying test article.
6. Compress for one minute
7. Remove compression, observe for bleeding.
8. If bleeding, repeat steps 4 and 5.
9. Test article fails if 15 one minute compressions fail to stop bleeding.
10. Collect tissues for pathology 16.2 Treatment and Analysis of Splenic Incisions; Materials and Methods ANIMALS. This study was conducted in four immature female Yorkshire White wine weighing between 34 and 37 kg. The following protocol was used in every case.

Protocol
1. After standard premedication, anesthetize animal by inhalation with 100% $O_2$ and 1–2% Halothane. Draw control blood sample for CBC and platelet count.
2. Deliver spleen through midline abdominal incision using electrocautery to maintain absolute hemostasis.
3. Isolate spleen with sponges.
4. Create a 2 cm×2 cm area of capsular stripping on the surface of the spleen to a depth of 3 mm.
5. Allow wound to bleed freely for 10 seconds.
6. Remove accumulated blood with Surgical sponge.
7. Apply test agent.
8. Apply gentle pressure for 1 minute.
9. Remove pressure, observe for bleeding for 2 minutes.
10. If wound bleeds, repeat 5 and 6.
11. Record the number of compressions needed to control bleeding and the time to hemostasis.
12. Document if complete cessation of bleeding was achieved. (Defined as no rebleeding for two minutes after cessation of bleeding.)
13. Collect the tissues for pathology 16.3 Spleen Immunostaining Protocol Immunostaining was performed using the ET-1 Staining Kit from Peninsula Laboratories, Inc. (Cat. # HIS-6901) with minor modifications.

Slide Preparation and Staining Procedure

1. Spleen tissue is sampled and preserved by embedding the samples in paraffin, on slides, using standard methods. Paraffin is subsequently removed from the by incubating them for 10 minutes in 100% xylene. Rehydrate the slides in a graded series of 100% Ethanol, 95% Ethanol, and then in tap water by dipping them 5 times in each solution. Circumscribe tissue samples with an Imm Edge waterproof pen (Vector Laboratories Cat. # H-4000). Store slides in PBS pH 7.4 solution in a coplin jar.
2. Dilute Antigen Unmasking solution (Vector Laboratories Cat. # H-3300) 100× and heat for 30–45 seconds in another coplin jar. Transfer the slides to this solution and incubate for 20 minutes. Make sure there is enough solution to cover the tissue samples to prevent drying out. Rinse slides well with PBS pH 7.4 solution for 2 minutes; repeat twice. Drain or blot the slides to remove excess solution.
3. Add 2 drops or 100 µL of Normal Goat Serum Blocking Solution to each slide. Incubate for 20 minutes at room temperature. Drain or blot excess solution from the slides. Do not rinse.
4. Reconstitute the lyophilized primary antibody with 32 µL of PBS pH 7.4 solution. From this stock solution, dilute the primary antibody by a dilution factor of 400. Add 2 drops or 100 µL of diluted primary antibody to each slide. Place slides horizontally on wooden sticks in a moisture chamber and incubate overnight at 4° C. Rinse well with PBS pH 7.4 solution for 2 minutes; repeat twice.
5. Add 2 drops or 100 µL of Biotinylated secondary antibody to each slide. Incubate for 30 minutes at room temperature. Rinse well with PBS pH 7.4 solution for 2 minutes; repeat twice.
6. Quench the slides in 3% Certified Hydrogen Peroxide (Fisher Cat. # H 312–500) for 30 minutes at room temperature in a coplin jar. Rinse well with PBS pH 7.4 for 2 minutes; repeat twice.
7. Add 2 drops or 100 µL of Streptavadin-HRP conjugate to each slide and incubate for 30 minutes at room temperature. Rinse well with PBS pH 7.4 solution for 2 minutes; repeat twice.
8. Make DAB Chromagen-Solution (Vector Laboratories Cat. # sk-41067) by adding 5.0 mL of distilled water to a glass scintillation vial. Add 2 drops of Buffer Stock Solution and mix well. Then, add 4 drops of DAB stock solution and mix well. Finally, add 2 drops of Hydrogen Peroxide solution and mix well. Add 200 µL of DAB Chromagen-Solution to each slide. Incubate for 3 minutes at room temperature. Rinse well with distilled water and blot.
9. Counterstain the slides with a stock solution of 0.2% Working Light Green Solution (Sigma Cat. # L 5382) with a dilution factor of 6. Dip the slides 3 times in Working Light Green solution and then dip the slides 5 times each in a dehydrating series of distilled water, then 95% Ethanol, then 100% Ethanol, and finally in 100% xylene. Drain or blot the slides to remove excess xylene.
10. Add 2 drops of Cytoseal XYL mounting solution (Stephens Scientific Cat. # 8312–4) and mount the slide.

16.4 Artery Immunostaining Protocol

Immunostaining of arterial tissues was performed using an ET-1 Staining Kit from Peninsula Laboratories, Inc. (Cat. # HIS-6901) with some modifications.

Slide Preparation

1. Pulmonary arteries are excised from deer obtained commercially.
2. Place the arteries in 100 mL of RPMI media and place on ice.
3. Make an incision in the artery with a scalpel.
4. Place a 1 cm×1 cm square membrane consisting of fully acetylated p-GlcNac fibers, over the incision for 15 minutes.
5. Make cross section slices of the artery at the membrane application site, for histology.
6. Place the sections in 9% Formaldehyde. Prepare the slides with Paraffin.

Staining Procedure

1. Deparaffinize the slides by incubating them for 10 minutes in 100% xylene. Rehydrate the slides in a graded series of 100% Ethanol, 95% Ethanol, and then in tap water by dipping them 5 times in each solution. Circumscribe tissue samples with an Imm Edge waterproof pen (Vector Laboratories Cat. # H-4000). Store slides in PBS pH 7.4 solution in a coplin jar.
2. Dilute Antigen Unmasking solution (Vector Laboratories Cat. # H-3300) 100-fold and heat for 30–45 seconds in another coplin jar. Transfer the slides to this solution and incubate for 20 minutes. Make sure there is enough solution to cover the tissue samples to prevent drying out. Rinse slides well with PBS pH 7.4 solution for 2 minutes; repeat twice. Drain or blot the slides to remove excess solution.
3. Add 2 drops or 100 µL of Normal Goat Serum Blocking Solution to each slide. Incubate for 20 minutes at room temperature. Drain or blot excess solution from the slides. Do not rinse.
4. Reconstitute the lyophilized primary antibody with 32 µL of PBS pH 7.4 solution. From this stock solution, dilute the primary antibody by a dilution factor of 100. Add 2 drops or 100 µL of diluted primary antibody to each slide. Place slides horizontally on wooden sticks in a moisture chamber and incubate overnight at 4° C. Rinse well with PBS pH 7.4 solution for 2 minutes; repeat twice.
5. Add 2 drops or 100 µL of Biotinylated secondary antibody to each slide. Incubate for 30 minutes at room temperature. Rinse well with PBS pH 7.4 solution for 2 minutes; repeat twice.
6. Quench the slides in 3% Certified Hydrogen Peroxide (Fisher Cat. # H 312–500) for 30 minutes at room temperature in a coplin jar. Rinse well with PBS pH 7.4 for 2 minutes; repeat twice.

7. Add 2 drops or 100 μL of Streptavadin-HRP conjugate to each slide and incubate for 30 minutes at room temperature. Rinse well with PBS pH 7.4 solution for 2 minutes; repeat twice.

8. Make DAB Chromagen-Solution (Vector Laboratories Cat. # sk-41067) by adding 5.0 mL of distilled water to a glass scintillation vial. Add 2 drops of Buffer Stock Solution and mix well. Then, add 4 drops of DAB stock solution and mix well. Finally, add 2 drops of Hydrogen Peroxide solution and mix well. Add 200 μL of DAB Chromagen-Solution to each slide. Incubate for 3 minutes at room temperature. Rinse well with distilled water and blot.

9. Counterstain the slides with a stock solution of 0.2% Working Light Green Solution (Sigma Cat. # L 5382) with a dilution factor of 6. Dip the slides 3 times in Working Light Green solution and then dip the slides 5 times each in a dehydrating series of distilled water, then 95% Ethanol, then 100% Ethanol, and finally in 100% xylene. Drain or blot the slides to remove excess xylene.

10. Add 2 drops of Cytoseal XYL mounting solution (Stephens Scientific Cat. # 8312–4) and mount the slide.

Results

Histological and immunological examination of the arterial tissue treated with a membrane consisting of fully acetylated p-GlcNac fibers stimulated immediate vasoconstriction at the contact site of injured artery tissue and the p-GlcNac polymer. The vasoconstriction induced by application of the p-GlcNac membrane was more easily seen, histologically, with the larger the experimental animals. Constriction of arterial tissue is more pronounced on the side of the artery to which the p-GlcNac membrane was applied. The results of these analyses are depicted in FIG. 23 and FIG. 24. Sixty minutes after application of a gauze dressing to porcine artery (FIG. 23 (A), and FIG. 24, sample A), comparable values for arterial wall thickness were obtaind, whether the wall was measured at the point of contact with the gauze, (1), or at a point on the side opposite from the point where the gauze dressing was applied. In contrast, application of a membrane formulated with semi-crystalline p-GlcNac to porcine artery (FIG. 23 (B), FIG. 24, sample B), induced a marked thickening of the wall at the area of contact (1), which was apparent 15 minutes after application of the membrane. After 60 minutes of contact, the thickness of the arterial wall, as measured at the area of contact with the p-GlcNac membrane (1), had returned to a level comparable to that measured at point on the opposite side of the artery (2).

Immunostaining experiments with antibodies to endothelin-1 showed secretion of endothelin-1 in the site of contact between the p-GlcNac membrane and living tissue. The in vitro experiment with deer pulmonary artery showed presence of endothelin-1 only on the contact surface of the artery with the p-GlcNac membrane. In vivo experiments showed substantially greater endothelin-1 release, not only on the contact surface between the treated tissue and the p-GlcNac membrane, but also in deeper layers of tissue. Within the first 15 minutes after application of the p-GlcNac membrane, more endothelin-1 secreted was detected than in the comparable analysis performed only after 60 minutes of contact between the treated tissue and the p-GlcNac membrane. Nevertheless, the constriction effect was stronger than other samples examined.

The same endothlelin-1 immunostaining was observed on slides with other samples, but it was much lower than with the p-GlcNac membrane. Histological and immunological analysis of spleen tissue contacted with the p-GlcNac membrane revealed a similar enhancement of endothelin-1 release. Again, within the first 15 minutes after application of the experimental membranes, endothelin-1 was observed only in those samples to which the p-GlcNac membrane had been applied. After 60 minutes of contact between the experimental membranes and the treated tissues, all samples revealed comparable levels of endothelin-1.

17. EXAMPLE p-GlcNac Induction of Vasoconstriction and Endothelin Release in the Absence of Blood Products This example demonstrates that the fully acetylated, semi-crystalline p-GlcNac of the present invention induces arterial vasoconstriction, in the absence of blood. More specifically, this example demonstrates that fully acetylated p-GlcNac significantly contracts isolated rat aortic rings via an endothelium-dependent mechanism, partly by endothelin-1 release from endothelial cells, in the absence of any of the components of the clotting cascade.

17.1 Materials and Methods

Aortic rings were obtained from Male Sprague-Dawley rats weighing 275–300 g. The rats were anesthetized with pentobarbital sodium (60 mg/kg) injected intraperitoneally. The aorta and the SMA were rapidly removed from rats and suspended in a warmed Krebs-Henseleit (KH) buffer consisting of (in mmol/l): 118 NaCl, 4.75 KCl, 2.54 $CaCl_2.2H_2O$, 1.19 $KH_2PO_4$, 1.19$MgSO_4.7H_2O$, 12.5 $NaHCO_3$, and 10.0 glucose. Isolated vessels were carefully freed of connective tissue and cut into rings 2–3 mm in length. The rings were then mounted on stainless steel hooks, suspended in a 10-ml tissue bath, and connected to FT-03 force displacement transducers (Grass Instrument, Quincy, Mass.) to record changes in force on a Grass model 7 oscillographic recorder. The baths were filled with KH buffer and aerated at 37° C. with 95% $O_2$+5% $CO_2$. A resting force of 0.5 g was applied to the SMA rings, and then the rings were equilibrated for 90 minutes. During this period, the buffer in the tissue bath was replaced every 15–20 minutes, and the resting force of the vascular rings was adjusted until 0.5 g of pre-load was maintained. After 90 to 120 minutes of equilibration, the rings were exposed to 100 nM U-46619 (9,11-dideoxy-9α-11α-methaneepoxy-prostagalandin $F_{2\alpha}$, Biomol Research Laboratories, Plymouth Meeting, Pa.), a thromboxane $A_2$ mimetic, to generate 1.0 g of developed force. Once a stable contraction was obtained, acetylcholine, a typical endothelium-dependent vasodilator, was added to the bath in cumulative concentrations of 0.1, 1, 10, and 100 nM to assess the integrity of endothelium. After the cumulative response was stabilized, the rings were washed and again allowed to equilibrate to baseline.

The procedure was repeated with U-46619 followed by p-GlcNAc. p-GlcNAc produced a concentration-dependent vasocontraction from 14 to 140 g/ml, as indicated in FIG. 23. At a developed concentration of 140 g/ml, p-GlcNAc significantly contracted aortic rings by 218±21 mg of developed force (p<0.01). De-endothelialized (i. e. endothelium was removed by gently rolling the aortic rings over a twisted stainless steel wire covered with cotton) aortic rings were contracted by only 33±12 mg of developed force. Pretreatment with an endothelin EtA receptor antagonist, JKC-301 (Cyclo[$_D$-Asp-Pro-$_D$-Ile-Leu-$_D$-Trp]), Sigma Biochemicals and Reagents, St. Louis, Mo.) (0.5 and 1 M), significantly diminished p-GlcNac-induced vasoconstriction by 57 to 61% ($p<0.01$).

The procedure was repeated with U-46619 followed by p-GlcNAc. p-GlcNAc produced a concentration-dependent vasocontraction from 14 to 140 µg/ml, as indicated in FIG. 22. At a developed concentration of 140 µg/ml, p-GlcNAc significantly contracted aortic rings by 218±21 mg of developed force ($p<0.01$). De-endothelialized (i.e. endothelium was removed by gently rolling the aortic rings over a twisted stainless steel wire covered with cotton) aortic rings were contracted by only 33±12 mg of developed force. Pretreatment with an endothelin EtA receptor antagonist, JKC-301 (Cyclo[$_D$-Asp-Pro-$_D$-Ile-Leu-$_D$-Trp]), Sigma Biochemicals and Reagents, St. Louis, Mo.) (0.5 and 1 M), significantly diminished p-GlcNac-induced vasoconstriction by 57 to 61% ($p<0.01$).

It is apparent that many modifications and variations of this invention as set forth here may be made without departing from the spirit and scope thereof. The specific embodiments described above are given by way of example only, and the invention is limited only by the terms of the appended claims.

Various publications are cite herein, the disclosures of which are incorporated by reference in their entireties.

What is claimed is:

1. A method for achieving at least a transient, localized, physiological response, comprising:
   topically administering to a patient in need of said modulation, a sufficient amount of a non-barrier forming material comprising poly-$\beta$-1→4 N-acetylglucosamine polymers, wherein the poly-$\beta$-1→4 N-acetylglucosamine polymer comprises about 50 to about 150,000 N-acetylglucosamine monosaccharides covalently attached in a $\beta$-1→4 conformation, wherein the non-barrier forming material is in the form of a solution, a suspension, an emulsion, a spray, or a foam, so that the patient experiences at least a transient, localized physiological response selected from the group consisting of stimulation of endothelin-1 release, vasoconstriction, and reduction in blood flow out of a breached vessel.

2. The method of claim 1, wherein the method achieves at least a transient, localized physiological response comprising stimulation of endothelin-1 release.

3. The method of claim 2, wherein the endothelin-1 is released from vascular endothelial cells.

4. The method of claim 1, wherein the method achieves at least a transient, localized physiological response comprising vasoconstriction.

5. The method of claim 1, wherein the method achieves at least a transient, localized physiological response comprising reduction in blood flow out of a breached vessel.

6. The method of claim 5, wherein the patient experiences cessation of blood flow out of the breached vessel.

7. The method of claim 1, wherein the poly-$\beta$-1→4 N-acetylglucosamine polymer comprises about 50 to about 50,000 N-acetylglucosamine monosaccharides covalently attached in a $\beta$-1→4 conformation.

8. The method of claim 7, wherein the poly-$\beta$-1→4 N-acetylglucosamine polymer comprises about 50 to about 10,000 N-acetylglucosamine monosaccharides covalently attached in a $\beta$-1→4 conformation.

9. The method of claim 8, wherein the poly-$\beta$-1→4 N-acetylglucosamine polymer comprises about 50 to about 4,000 N-acetylglucosamine monosaccharides covalently attached in a $\beta$-1→4 conformation.

10. The method of claim 1, wherein the poly-$\beta$-1→4 N-acetylglucosamine polymer comprises at least one non-acetylated glucosamine monosaccharide unit, and wherein at least 40% of the glucosamine monsaccharide units are N-acetylated.

11. The method of claim 1, wherein the patient is a human.

12. The method of claim 1, wherein the non-barrier forming material is applied directly to a blood vessel.

13. The method of claim 1, wherein the the physiological response affects a blood vessel selected from the group consisting of capillary, vein, and artery.

14. The method of claim 13, wherein the blood vessel is a breached blood vessel.

15. The method of claim 14, whereby the patient experiences cessation of bleeding.

16. The method of claim 1, wherein the extent of the transient, localized physiological response is substantially proportional to the amount of poly-$\beta$-1→4 N-acetylglucosamine administered.

17. The method of claim 1, wherein said polymers are substantially free of protein.

18. The method of claim 1, wherein said polymers are substantially free of organic contaminants.

19. The method of claim 1, wherein said polymers are substantially free of inorganic contaminants.

20. A method for treating a patient having a vascular disorder, comprising:
    topically administering to a patient in need of such treatment, a sufficient amount of a non-barrier forming material comprising poly-$\beta$-1→4 N-acetylglucosamine polymers, wherein the poly-$\beta$-1→4 N-acetylglucosamine polymer comprises about 50 to about 150,000 N-acetylglucosamine monosaccharides covalently attached in a $\beta$-1→4 conformation, wherein the non-barrier forming material is in the form of a solution, a suspension, an emulsion, a spray, or a foam, whereby said administering ameliorates said vascular disorder.

21. The method of claim 20, wherein the vascular disorder is selected from the group consisting of menorrhagia, cerebral aneurysm, abdominal aneurysm, uterine fibroid lesion, and blood vessel puncture.

22. The method of claim 20, wherein said polymers are substantially free of protein.

23. The method of claim 20, wherein said polymers are substantially free of organic contaminants.

24. The method of claim 20, wherein said polymers are substantially free of inorganic contaminants.

25. The method of claim 20, wherein the method achieves at least a transient, localized physiological response comprising stimulation of endothelin-1 release.

26. The method of claim 20, wherein the method achieves at least a transient, localized physiological response comprising vasoconstriction.

27. The method of claim 20, wherein the method achieves at least a transient, localized physiological response comprising reduction in blood flow out of a breached vessel.

* * * * *